(12) United States Patent
Cockerill et al.

(10) Patent No.: US 7,265,123 B2
(45) Date of Patent: Sep. 4, 2007

(54) HETEROCYCLIC COMPOUNDS

(75) Inventors: George Stuart Cockerill, Maulden (GB); Karen Elizabeth Lackey, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 11/562,047

(22) Filed: Nov. 21, 2006

(65) Prior Publication Data

US 2007/0093512 A1  Apr. 26, 2007

Related U.S. Application Data

(62) Division of application No. 11/400,284, filed on Apr. 7, 2006, now Pat. No. 7,189,734, which is a division of application No. 11/061,578, filed on Feb. 18, 2005, now Pat. No. 7,084,147, which is a division of application No. 10/030,527, filed on Jan. 9, 2002, now Pat. No. 6,933,299.

(30) Foreign Application Priority Data

| Jul. 9, 1999 | (GB) | ................................... 9916213.3 |
| Jul. 9, 1999 | (GB) | ................................... 9916218.2 |

(51) Int. Cl.
*C07D 521/00* (2006.01)
*A61K 31/519* (2006.01)
(52) U.S. Cl. .................................. 514/258.1; 544/279
(58) Field of Classification Search ............... 544/279; 514/258.1
See application file for complete search history.

(56) References Cited

U.S. PATENT DOCUMENTS

| 4,074,057 A | 2/1978 | Kawamatsu et al. |
| 4,166,735 A | 9/1979 | Pilgram et al. |
| 5,457,105 A | 10/1995 | Barker |
| 5,480,883 A | 1/1996 | Spada et al. |
| 5,616,582 A | 4/1997 | Barker |
| 5,646,153 A | 7/1997 | Spada et al. |
| 5,654,307 A | 8/1997 | Bridges et al. |
| 5,710,158 A | 1/1998 | Meyers et al. |
| 5,773,476 A | 6/1998 | Chen et al. |
| 5,789,427 A | 8/1998 | Chen et al. |
| 5,821,246 A | 10/1998 | Brown et al. |

FOREIGN PATENT DOCUMENTS

| DE | 43 08 014 | 9/1994 |
| EP | 0 370 704 B1 | 5/1990 |
| EP | 0 414 386 | 2/1991 |
| EP | 0 452 002 A2 | 10/1991 |
| EP | 0534 341 A1 | 3/1993 |
| EP | 0 566 226 | 10/1993 |
| WO | 86/06718 | 11/1986 |
| WO | 93/13097 | 6/1993 |
| WO | 93/17682 | 9/1993 |
| WO | 93/18035 | 9/1993 |
| WO | 94/04526 | 3/1994 |
| WO | 95/00511 | 1/1995 |
| WO | 95/15758 | 6/1995 |
| WO | 95/19774 | 7/1995 |
| WO | 95/24190 | 9/1995 |
| WO | 96/09294 | 3/1996 |
| WO | 96/15118 | 5/1996 |
| WO | 96/16960 | 6/1996 |
| WO | 96/30347 | 10/1996 |
| WO | 96/40142 | 12/1996 |
| WO | 97/03069 | 1/1997 |
| WO | 97/13771 | 4/1997 |
| WO | 97/18212 | 5/1997 |
| WO | 97/30034 | 8/1997 |
| WO | 97/30035 | 8/1997 |
| WO | 97/38983 | 10/1997 |
| WO | 98/02434 | 1/1998 |
| WO | 98/02437 | 1/1998 |
| WO | 98/02438 | 1/1998 |
| WO | 98/13354 | 4/1998 |
| WO | 98/14451 | 4/1998 |
| WO | 99/00636 | 2/1999 |
| WO | 99/35132 | 7/1999 |
| WO | 99/35146 | 7/1999 |

OTHER PUBLICATIONS

Zydowsky et al., "Synthesis and In Vitro Evaluation of Fused Ring Heterocycle-Containing Angiotensin II Antagonists", 1994, Bioorganic & Medicinal Chemistry Letters, vol. 4, No. 1, pp. 173-176.
Robba et al., "Thienopyrimidines—II Etude De La Thieno [3,2-d] Pyrimidine et de Quelques Derives", 1971, Tetrahedron vol. 27, pp. 487-499.
Hunter, "A Thousand and One Protein Kinases", Cell, vol. 50, pp. 823-829, Sep. 11, 1987.
Modjtahedi et al., "EGFR blockade by tyrosine kinase inhibitor or monoclonal antibody inhibits growth, directs terminal differentiation and induces apoptosis in the human squamous cell carcinoma HN", May 14, 1998, International Journal of Oncology, vol. 13, pp. 335-342.
Hung et al., "Basic Science of HER-2/neu: A Review", Aug. 1999, Seminars in Oncology, vol. 26, No. 4, Suppl. 12, pp. 51-59.
J.R. Woodburn, "The Epidermal Growth Factor Receptor and Its Inhibition in Cancer Therapy", 1999, Pharmacol Ther., vol. 82, Nos. 2-3, pp. 241-250.
Ullrich et al., "Signal Transduction by Receptors with Tyrosine Kinase Activity", Apr. 20, 1990, Cell, vol. 61, pp. 203-212.

(Continued)

*Primary Examiner*—Bruck Kifle
(74) *Attorney, Agent, or Firm*—John L. Lemanowicz; Kathryn L. Coulter

(57) ABSTRACT

Heteroaromatic compounds are described, methods for their preparation, pharmaceutical compositions containing them, methods of use, and their use in medicines. In particular, the invention relates to quinazoline and pyridopyrimidine derivatives which exhibit protein tyrosine kinase inhibition.

29 Claims, No Drawings

OTHER PUBLICATIONS

Bridges et al, "Tyrosine Kinase Inhibitors", J Med. Chem., vol. 39, No. 1, Jan. 5, 1996, pp. 267-276.
Rewcastle et al., "Tyrosine Kinase Inhibitors", J. Med. Chem., vol. 38, No. 18, 1995, pp. 3482-3487.
G.W. Rewcastle et al., "Tyrosine Kinase Inhibitors. 10. Isomeric 4-[(3-bromophenyl)amino]pyrido[d]pyrimidines are potent ATP binding sit inhibitors of the tyrosine kinase function of the epidermal growth factor receptor", Journal of Medicinal Chemistry, 1996, vol. 39, No. 9, pp. 1823-1835.
Y. Katsura et al., "Studies on antiulcer drugs. V. Synthesis and antiulcer activity of aralkybenzozoles", Chemical and Pharmaceutical Bulletin, 1992, vol. 40, No. 8, pp. 2062-2072.
T. Shoda et al., "Studies on antidiabetic agents. II. Synthesis of 5-[4-(methylcyclohexylmethoxy)benzyl]thiazolidine-2,4-dione and its derivatives", Chemical and Pharmaceutical Bulletin, 1982, vol. 30, pp. 3580-3600.
G.W. Rewcastle et al., "Synthesis of 6-substituted pyrido[3,d-d]pyrimidine-4(3H)-ones via directed lithiation of 2-substituted 5-aminopyridine derivatives", Journal of the Chemical Society, Perkins Transactions1., 1996, pp. 2221-2226.
A.F. Wilks, Progress in Growth Factor Research, 1990, 2, pp. 97-111.
S.A. Courtneidge, Dev. Suppl. 1, 1993, pp. 57-64.
J.A. Cooper, Semin. Cell Biol., 1994, 5(6), pp. 377-387.
R.F. Paulson, Semin. Immunol., 1995, 7(4) , pp. 267-277.
A.C. Chan, Curr. Opin. Immunol., 1996, 8(3), pp. 394-401.
Dvir et al., J. Cell. Biol. 1991, 113, pp. 857-865.
Buchdunger et al., Proc. Natl. Acad. Sci. USA; 1991, 92, pp. 2558-2562.
Klausner and Samelson, Cell; 1991, 64, pp. 875-878.
Berkois, Blood; 1992, 79(9), pp. 2446-2454.
Salari et al., FEBS; 1990, 263(1), pp. 104-108.
Ohmichi et al., Biochemistry, 1992, 31, pp. 4034-4039.
L.K. Shawyer, DDT, 1997, 2(2), pp. 50-63.
Pharmaceutical Research, 1986, 3(6), p. 318.
C.E. Housecroft et al., Inorg. Chem., 1991, 30(1), pp. 125-130.
H. Sato et al., Bioorganic and Medicinal Chemistry Letters, 1995, 5(3), pp. 233-236.
J. Org. Chem., 1990, 55, pp. 1379-1390.
Helv. Chim. Acta., 1983, 66(4), p. 1046.
T.R. Kelly and F. Lang, Tetrahedron Lett., 36, 9293, 1995.
J. Chem. Soc., Chem. Commun., 1988, p. 560.
V.P. Semenov and A.N. Studenikov, "Synthesis of 7-iodo-4aminoquinoline derivatives", Khim Geterotsikl. Soedin., 1980, Issue 7, pp. 972-975.
R. Dempsy and E. Skito, Biochemistry, 30, 1991, p. 8480.
J. Org. Chem., 1992, 57(11), pp. 3126-3131.
A. Lee and W-C Dai, Tetrahedron, 1997, 53(3), pp. 859-868.

HETEROCYCLIC COMPOUNDS

This application is a divisional of U.S. Ser. No. 11/400,284 filed Apr. 7, 2006, now U.S. Pat. No. 7,189,734 which is a divisional of U.S. Ser. No. 11/061,578 filed on Feb. 18, 2005, now U.S. Pat. No. 7,084,147, which is a divisional of U.S. Ser. No. 10/030,527 filed on Jan. 9, 2002, now U.S. Pat. No. 6,933,299, which was filed pursuant to 35 U.S.C. § 371 as a United States National Phase Application of International Application No. of PCT/US00/18128, filed Jun. 30, 2000, which claims priority from GB9916213.3 and GB9916218.2 tiled Jul. 9, 1999, each of which is herein incorporated by reference in its entirety.

The present invention relates to a series of substituted heteroaromatic compounds, methods for their preparation, pharmaceutical compositions containing them and their use in medicine. In particular, the invention relates to quinazoline and pyridopyrimidine derivatives which exhibit protein tyrosine kinase inhibition.

Protein tyrosine kinases catalyse the phosphorylation of specific tyrosyl residues in various proteins involved in the regulation of cell growth and differentiation (A. F. Wilks, Progress in Growth Factor Research, 1990, 2, 97-111; S. A. Courtneidge, Dev. Supp.1, 1993, 57-64; J. A. Cooper, Semin. Cell Biol., 1994, 5(6), 377-387; R. F. Paulson, Semin. Immunol., 1995, 7(4), 267-277; A. C. Chan, Curr. Opin. Immunol., 1996, 8(3), 394-401). Protein tyrosine kinases can be broadly classified as receptor (e.g. EGFr, c-erbB-2, c-met, tie-2, PDGFr, FGFr) or non-receptor (e.g. c-src, lck, zap70) kinases. Inappropriate or uncontrolled activation of many of these kinase, i.e. aberrant protein tyrosine kinase activity, for example by over-expression or mutation, has been shown to result in uncontrolled cell growth.

Protein kinases play a critical role in the control of cell growth and differentiation and are key mediators of cellular signals leading to the production of growth factors and cytokines. See, for example, Schlessinger and Ullrich, *Neuron* 1992, 9, 383. A partial, non-limiting, list of such kinases includes abl, ARaf, ATK, ATM, bcr-abl, Blk, BRaf, Brk, Btk, CDK1, CDK2, CDK3, CDK4, CDK5, CDK6, CDK7, CDK8, CDK9, cfms, c-fms, c-kit, c-met, cRaf1, CSF1R, CSK, c-src, EGFR, ErbB2, ErbB3, ErbB4, ERK, ERK1, ERK2, Fak, fes, FGFR1, FGFR2, FGFR3, FGFR4, FGFR5, Fgr, FLK-4, Fps, Frk, Fyn, GSK, gsk3a, gsk3b, Hck, IGF-1R, IKK, IKK1, IKK2, IKK3, INS-R, Integrin-linked kinase, Jak, JAK1, JAK2, JAK3, JNK, JNK, Lck, Lyn, MEK, MEK1, MEK2, p38, PDGFR, PIK, PKB1, PKB2, PKB3, PKC, PKCa, PKCb, PKCd, PKCe, PKCg, PKCl, PKCm, PKCz, PLK1, Polo-like kinase, PYK2, $tie_1$, $tie_2$, TrkA, TrkB, TrkC, UL13, UL97, VEGF-R1, VEGF-R2, Yes and Zap70. Protein kinases have been implicated as targets in central nervous system disorders such as Alzheimer's (Mandelkow, E. M. et al. *FEBS Lett.* 1992, 314, 315; Sengupta, A. et al. *Mol. Cell. Biochem.* 1997, 167,99), pain sensation (Yashpal, K. *J. Neurosci.* 1995, 15, 3263-72), inflammatory disorders such as arthritis (Badger, *J. Pharm. Exp. Ther.* 1996, 279, 1453), psoriasis (Dvir, et al, *J. Cell Biol.* 1991, 113, 857), bone diseases such as osteoporosis (Tanaka et al, *Nature,* 1996, 383, 528), cancer (Hunter and Pines, *Cell* 1994, 79, 573), atherosclerosis (Hajjar and Pomerantz, *FASEB J.* 1992, 6, 2933), thrombosis (Salari, *FEBS* 1990, 263, 104), metabolic disorders such as diabetes (Borthwick, A. C. et al. *Biochem. Biophys. Res. Commun.* 1995, 210, 738), blood vessel proliferative disorders such as angiogenesis (Strawn et al *Cancer Res.* 1996, 56, 3540; Jackson et al *J. Pharm. Exp. Ther.* 1998, 284, 687), restenosis (Buchdunger et al, *Proc, Nat. Acad. Sci USA* 1991, 92, 2258), autoimmune diseases and transplant rejection (Bolen and Brugge, *Ann. Rev. Immunol.* 1997, 15, 371) and infectious diseases such as viral (Littler, E. *Nature* 1992, 358, 160), and fungal infections (Lum, R. T. PCT Int. Appl., WO 9805335 A1 980212).

Aberrant activity of protein tyrosine kinases, such as c-erbB-2, c-src, c-met, EGFr and PDGFr have been implicated in human malignancies. Elevated EGFr activity has, for example, been implicated in non-small cell lung, bladder and head and neck cancers, and increased c-erbB-2 activity in breast, ovarian, gastric and pancreatic cancers. Inhibition of protein tyrosine kinases should therefore provide a treatment for tumours such as those outlined above.

Aberrant protein tyrosine kinase activity has also been implicated in a variety of other disorders: psoriasis, (Dvir et al, J. Cell. Biol; 1991, 113, 857-865), fibrosis, atherosclerosis, restenosis, (Buchdunger et al, Proc. Natl. Acad. Sci. USA; 1991, 92, 2258-2262), auto-immune disease, allergy, asthma, transplantation rejection (Klausner and Samelson, Cell; 1991, 64, 875-878), inflammation (Berkois, Blood; 1992, 79(9), 2446-2454), thrombosis (Salari et al, FEBS; 1990, 263(1), 104-108), bronchitis (Takeyama, K. et al. Proc. Natl. Acad. Sci. USA; 1999, 96(6):3081-3086), and nervous system diseases (Ohmichi et al, Biochemistry, 1992, 31, 4034-4039). Inhibitors of the specific protein tyrosine kinases involved in these diseases eg PDGF-R in restenosis and EGF-R in psoriasis, should lead to novel therapies for such disorders. P56lck and zap 70 are indicated in disease conditions in which T cells are hyperactive e.g. rheumatoid arthritis, autoimmune disease, allergy, asthma and graft rejection. The process of angiogenesis has been associated with a number of disease states (e.g. tumourogenesis, psoriasis, rheumatoid arthritis) and this has been shown to be controlled through the action of a number of receptor tyrosine kinases (L. K. Shawver, DDT, 1997, 2(2), 50-63).

It is therefore a general object of the present invention to provide compounds suitable for the treatment of disorders mediated by protein tyrosine kinase activity, and in particular treatment of the above mentioned disorders.

In addition to the treatment of tumours, the present invention envisages that other disorders mediated by protein tyrosine kinase activity may be treated effectively by inhibition, including preferential inhibition, of the appropriate protein tyrosine kinase activity.

Broad spectrum inhibition of protein tyrosine kinase may not always provide optimal treatment of, for example tumours, and could in certain cases even be detrimental to subjects since protein tyrosine kinases provide an essential role in the normal regulation of cell growth.

It is another object of the present invention to provide compounds which preferentially inhibit protein tyrosine kinases, such as EGFr, c-erbB-2, c-erbB-4, c-met, tie-2, PDGFr, c-src, lck, Zap70, and fyn. There is also perceived to be a benefit in the preferential inhibition involving small groups of protein tyrosine kinases, for example groups including two or more of c-erbB-2, c-erbB-4, EGF-R, lck and zap70.

A further object of the present invention is to provide compounds useful in the treatment of protein tyrosine kinase related diseases which minimise undesirable side-effects in the recipient.

The present invention relates to heterocyclic compounds which may be used to treat disorders mediated by protein tyrosine kinases and in particular have anti-cancer properties. More particularly, the compounds of the present invention are potent inhibitors of protein tyrosine kinases such as such as EGFr, c-erbB-2, c-erbB-4, c-met, tie-2, PDGFr, c-src, lck, Zap70, and fyn, thereby allowing clinical management of particular diseased tissues. In one embodiment, compounds of the present invention are potent inhibitors of c-erbB-2 and EGFr. Consequently, compounds of the present invention may be used to treat disorders mediated by aberrant protein tyrosine kinase activity wherein both c-erbB-2 and EGFr exhibit aberrant activity.

The present invention envisages, in particular, the treatment of human malignancies, for example breast, non-small cell lung, ovary, stomach, and pancreatic tumours, especially those driven by EGF-R or erbB-2, using the compounds of the present invention. For example, the invention includes compounds which are highly active against the c-erbB-2 protein tyrosine kinase often in preference to the EGF receptor kinase hence allowing treatment of c-erbB-2 driven tumours. However, the invention also includes compounds which are highly active against both c-erbB-2 and EGF-R receptor kinases hence allowing treatment of a broader range of tumours.

More particularly, the present invention envisages that disorders mediated by protein tyrosine kinase activity may be treated effectively by inhibition of the appropriate protein tyrosine kinase activity in a relatively selective manner, thereby minimising potential side effects.

Accordingly, the present invention provides a compound of formula (I)

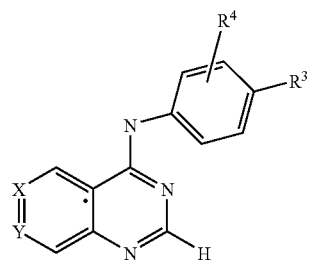

(I)

or a salt or solvate thereof, or a physiologically functional derivative thereof;

wherein

X is $CR^1$ and Y is N;
or X is N and Y is $CR^1$;
or X is $CR^1$ and Y is $CR^2$;
or X is $CR^2$ and Y is $CR^1$;
$R^1$ represents a group $R^5SO_2CH_2CH_2Z\text{-}(CH_2)_p\text{—Ar—}$, wherein Ar is selected from phenyl, furan, thiophene, pyrrole and thiazole, each of which may optionally be substituted by one or two halo, $C_{1-4}$ alkyl or $C_{1-4}$ alkoxy groups; Z represents O, S, NH or $NR^6$; p is 1, 2, 3 or 4;
$R^5$ is $C_{1-6}$ alkyl optionally substituted by one or more $R^8$ groups;
or $R^5$ is $C_{1-6}$ alkyl substituted by a 5 to 10-membered heterocyclic group or a 3 to 10-membered carbocyclic group, each of which may be optionally substituted by one or more $R^8$ groups;
or $R^5$ is selected from the group consisting of a 5 to 10-membered heterocyclic group or a 3 to 10-membered carbocyclic group, each of which may be optionally substituted by one or more $R^8$ groups;
each $R^8$ is independently selected from halo, hydroxy, $C_{1-4}$ alkoxy, nitrile, $NH_2$ or $NR^6R^7$;
$R^6$ is $C_{1-4}$ alkyl, $C_{1-4}$ alkoxy-$C_{1-4}$alkyl, hydroxy$C_{1-4}$alkyl, $CF_3C(O)$ or $CH_3C(O)$;

$R^7$ is hydrogen or $R^6$;
$R^2$ is selected from hydrogen, halo, hydroxy, $C_{1-4}$ alkyl or $C_{1-4}$ alkoxy;
$R^3$ is selected from pyridylmethoxy, benzyloxy, halo-, dihalo- or trihalobenzyloxy;
$R^4$ is selected from hydrogen, halogen, $C_{1-4}$ alkyl, $C_{2-4}$ alkynyl or cyano;
with the proviso that when p is 1 and Z is NH, $R^5$ cannot represent $CH_3$.

In a preferred embodiment, $R^4$ is located on the phenyl ring as indicated in formula (I').

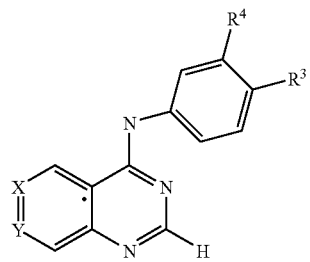

(I')

In one embodiment, the group $R^5$ is an alkylene group linked to a heterocyclic or carbocyclic group, the alkylene group is preferably $C_{1-4}$ alkylene, more preferably $C_{1-3}$ alkylene, most preferably methylene or ethylene.

The definitions for X and Y thus give rise to a number of possible basic ring systems for the compounds of formula (I). In particular the compounds may be contain the following basic ring systems:

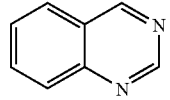

(1)

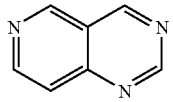

(2)

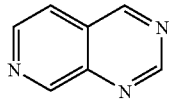

(3)

Ring systems (1) and (3) are preferred.

Alkyl groups containing three or more carbon atoms may be straight, branched or cyclised; preferably they are straight or branched. References to a specific alkyl group such as "butyl" is intended to refer to the straight chain (n-) isomer only. References to other generic terms such as alkoxy, alkylamino etc. are to be interpreted analogously.

Suitable values for the various groups listed above within the definitions for $R^1$, $R^2$, $R^3$, $R^4$, $R^5$, $R^6$, $R^7$, and $R^8$ are as follows:

halo is, for example, fluoro, chloro, bromo or iodo; preferably it is fluoro, chloro or bromo, more preferably fluoro or chloro;

$C_{1-4}$ alkyl is, for example, methyl, ethyl, propyl, isopropyl, butyl, isobutyl, sec-butyl or tert-butyl; preferably it is methyl, ethyl, propyl, isopropyl or butyl, more preferably methyl;

$C_{1-6}$ alkyl is, for example, methyl, ethyl, propyl, isopropyl, butyl, isobutyl, sec-butyl, tert-butyl, pentyl, iso-pentyl, sec-pentyl, hexyl, iso-hexyl, sec-hexyl; preferably it is methyl, ethyl, propyl, isopropyl, butyl, pentyl, or hexyl, more preferably ethyl, propyl and isopropyl;

$C_{2-4}$ alkenyl is, for example, ethenyl, prop-1-enyl or prop-2-enyl; preferably it is ethenyl;

$C_{2-4}$ alkynyl is, for example, ethynyl, prop-1-ynyl or prop-2-ynyl; preferably it is ethynyl;

$C_{1-4}$ alkoxy is, for example, methoxy, ethoxy, n-propoxy, isopropoxy, n-butoxy, isobutoxy, sec-butoxy or tert-butoxy; preferably it is methoxy, ethoxy, propoxy, isopropoxy or butoxy; more preferably it is methoxy;

Heterocyclic groups comprise one or more rings which may be saturated, unsaturated, or aromatic and which may independently contain one or more nitrogen, oxygen, or sulfur heteroatoms, where N-oxides and sulfur monoxides and sulfur dioxides are permissible heteroaromatic substitutions in each ring.

Examples of suitable heterocyclic groups include acridine, benzimidazole, benzofuran, benzothiophene, benzoxazole, benzthiazole, carbazole, cinnoline, dioxin, dioxane, dioxalane, dithiane, dithiazine, dithiazole, dithiolane, furan, imidazole, imidazoline, imidazolidine, indole, indoline, indolizine, indazole, isoindole, isoquinoline, isoxazole, isothiazole, morpholine, napthyridine, oxazole, oxadiazole, oxathiazole, oxathiazolidine, oxazine, oxadiazine, phenazine, phenothiazine, phenoxazine, phthalazine, piperazine, piperidine, pteridine, purine, pyran, pyrazine, pyrazole, pyrazoline, pyrazolidine, pyridazine, pyridine, pyrimidine, pyrrole, pyrrolidine, pyrroline, quinoline, quinoxaline, quinazoline, quinolizine, tetrahydrofuran, tetrazine, tetrazole, thiophene, thiadiazine, thiadiazole, thiatriazole, thiazine, thiazole, thiomorpholine, thianaphthalene, thiopyran, triazine, triazole, or trithiane.

Preferred heterocyclic groups are aromatic groups selected from furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole.

More preferred heterocyclic groups are aromatic groups selected from furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine.

Most preferred heterocyclic groups are aromatic groups selected from pyridine and imidazole, especially pyrid-2-yl and imidazol-2-yl.

Carbocyclic groups comprise one or more rings which may be independently saturated, unsaturated, or aromatic and which contain only carbon and hydrogen.

Preferred carbocyclic groups include aromatic groups selected from phenyl, biphenyl, naphthyl (including 1-naphthyl and 2-naphthyl) and indenyl.

Further suitable carbocyclic groups include cyclopropyl, cyclobutyl, cyclopentyl, cyclohexyl, cycloheptyl, cyclooctyl, tetralin, decalin, cyclopentenyl and cyclohexenyl.

A more preferred carbocyclic group is phenyl.

In an embodiment, heterocyclic groups and carbocyclic groups included within the group $R^5$ are unsubstituted.

In an especially preferred embodiment X is $CR^1$ and Y is $CR^2$ (ring system (1) above).

In a further especially preferred embodiment X is $CR^1$ and Y is N (ring system (3) above).

In a preferred embodiment $R^2$ represents hydrogen, halogen or $C_{1-4}$ alkoxy. In a more preferred embodiment $R^2$ represents hydrogen, fluoro or methoxy. In a most preferred embodiment $R^2$ represents hydrogen or fluoro.

In a preferred embodiment Z represents NH, $NR^6$ or O. In a more preferred embodiment Z presents NH or O. In a most preferred embodiment Z represents NH.

In a preferred embodiment p is 1, 2 or 3.

In a further preferred embodiment the group Ar does not carry any optional substituents.

In a further preferred embodiment Ar represents furan or thiazole.

In a preferred embodiment $R^5$ represents an aromatic heterocyclic or carbocyclic group optionally substituted by a $C_{1-4}$ alkyl group (especially a methyl group).

In a more preferred embodiment $R^5$ represents pyridyl (especially pyrid-2-yl), phenyl, imidazolyl or N-methylimidazolyl (especially imidazol-2-yl).

In a preferred embodiment, $R^5$ represents $C_{1-6}$ alkyl optionally substituted by one or more groups selected from halo, hydroxy, $C_{1-4}$ alkoxy, nitrile, $NH_2$ or $NR^6R^7$, wherein $R^7$ represents H or $R^6$, wherein $R^6$ is as defined above.

In a more preferred embodiment, $R^5$ represents $C_{1-6}$ alkyl optionally substituted by one or more groups selected from hydroxy, $C_{1-4}$ alkoxy, $NH_2$ or $NR^6R^7$, wherein $R^7$ represents H or $R^6$; and $R^6$ represents $C_{1-4}$ alkyl.

In a most preferred embodiment, $R^5$ represents unsubstituted $C_{1-6}$ alkyl; especially unsubstituted $C_{1-4}$ alkyl.

The side chain $R^5SO_2CH_2CH_2Z\text{-}(CH_2)_p$ may be linked to any suitable position of the group Ar. Similarly, the group $R^1$ may be linked to the carbon atom carrying it from any suitable position of the group Ar.

In a more preferred embodiment, when Ar represents furan the side chain $R^5SO_2CH_2CH_2Z\text{-}(CH_2)_p$ is in the 5-position of the furan ring and the link to the carbon atom carrying the group $R^1$ is from the 2-position of the furan ring.

In a further more preferred embodiment, when Ar represents thiazole the side chain $R^5SO_2CH_2CH_2Z\text{-}(CH_2)_p$ is in the 2-position of the thiazole ring and the link to the carbon atom carrying the group $R^1$ is from the 4-position of the thiazole ring.

In a preferred embodiment $R^3$ represents benzyloxy or fluorobenzyloxy (especially 3-fluorobenzyloxy).

In an especially preferred embodiment $R^4$ represents chloro, bromo, or hydrogen.

In a most especially preferred embodiment $R^3$ is represents benzyloxy or 3- fluorobenzyloxy and $R^4$ chloro or bromo.

In a more preferred embodiment there is provided a compound of formula (I) or a salt, solvate or physiologically functional derivative thereof wherein Y is $CR^2$, wherein $R^2$ is hydrogen, fluoro or methoxy; X is $CR^1$ wherein $R^1$ is as defined above in which Ar is unsubstituted furan or thiazole; $R^3$ is benzyloxy or fluorobenzyloxy; and $R^4$ is hydrogen, or is chloro or bromo.

In a further more preferred embodiment there is provided a compound of formula (I) or a salt, solvate or physiologically functional derivative thereof wherein X is $CR^2$, wherein $R^2$ is hydrogen, fluoro or methoxy; Y is $CR^1$ wherein $R^1$ is as defined above in which Ar is unsubstituted furan or thiazole; $R^3$ is benzyloxy or fluorobenzyloxy; and $R^4$ is hydrogen, or is chloro or bromo.

In a further more preferred embodiment there is provided a compound of formula (I) or a salt or solvate thereof wherein Y is N; X is $CR^1$ wherein $R^1$ is as defined above in which Ar is unsubstituted furan or thiazole; $R^3$ is benzyloxy or fluorobenzyloxy; and $R^4$ is hydrogen, or is chloro or bromo.

In a most preferred embodiment there is provided a compound of formula (I) or a salt or solvate thereof wherein Y is $CR^2$, wherein $R^2$ is hydrogen, fluoro or methoxy; X is $CR^1$ wherein $R^1$ is as defined above in which Ar is unsubstituted furan or thiazole; $R^3$ is fluorobenzyloxy; and $R^4$ is chloro or bromo.

In a further most preferred embodiment there is provided a compound of formula (I) or a salt or solvate thereof wherein Y is N; X is $CR^1$ wherein $R^1$ is as defined above in which Ar is unsubstituted furan or thiazole; $R^3$ is fluorobenzyloxy; and $R^4$ is chloro or bromo.

In a more preferred embodiment there is provided a compound of formula (I) or a salt or solvate thereof wherein Y is $CR^2$, wherein $R^2$ is hydrogen, fluoro or methoxy; X is $CR^1$ wherein $R^1$ is as defined above in which Ar is unsubstituted furan or thiazole; $R^3$ is benzyloxy or fluorobenzyloxy; $R^4$ is hydrogen, or is chloro or bromo; and $R^5$ is unsubstituted $C_{1-6}$ alkyl.

In a further more preferred embodiment there is provided a compound of formula (I) or a salt, solvate or physiologically functional derivative thereof wherein X is $CR^2$, wherein $R^2$ is hydrogen, fluoro or methoxy; Y is $CR^1$ wherein $R^1$ is as defined above in which Ar is unsubstituted furanor thiazole; $R^3$ is benzyloxy or fluorobenzyloxy; $R^4$ is hydrogen, or is chloro or bromo; and $R^5$ is unsubstituted $C_{1-6}$ alkyl.

In a further more preferred embodiment there is provided a compound of formula (I) or a salt, solvate or physiologically functional derivative thereof wherein Y is N; X is $CR^1$ wherein $R^1$ is as defined above in which Ar is unsubstituted furan or thiazole; $R^3$ is benzyloxy or fluorobenzyloxy; $R^4$ is hydrogen, or is chloro or bromo; and $R^5$ is unsubstituted $C_{1-6}$ alkyl.

In a most preferred embodiment there is provided a compound of formula (I) or a salt or solvate thereof wherein Y is $CR^2$, wherein $R^2$ is hydrogen, fluoro or methoxy; X is $CR^1$ wherein $R^1$ is as defined above in which Ar is unsubstituted furan or thiazole; $R^3$ is fluorobenzyloxy; $R^4$ is chloro or bromo; and $R^5$ is unsubstituted $C_{1-6}$ alkyl.

In a further most preferred embodiment there is provided a compound of formula (I) or a salt or solvate thereof wherein Y is N; X is $CR^1$ wherein $R^1$ is as defined above in which Ar is unsubstituted furan or thiazole; $R^3$ is fluorobenzyloxy; $R^4$ is chloro or bromo; and $R^5$ is unsubstituted $C_{1-6}$ alkyl.

In a more preferred embodiment there is provided a compound of formula (I) or a salt or solvate thereof wherein Y is $CR^2$, wherein $R^2$ is hydrogen, fluoro or methoxy; X is $CR^1$ wherein $R^1$ is as defined above in which Ar is unsubstituted furan or thiazole; $R^3$ is benzyloxy or fluorobenzyloxy; $R^4$ is hydrogen, or is chloro or bromo; and $R^5$ is pyridine, imidazole, or phenyl.

In a further more preferred embodiment there is provided a compound of formula (I) or a salt, solvate or physiologically functional derivative thereof wherein X is $CR^2$, wherein $R^2$ is hydrogen, fluoro or methoxy; Y is $CR^1$ wherein $R^1$ is as defined above in which Ar is unsubstituted furan or thiazole; $R^3$ is benzyloxy or fluorobenzyloxy; $R^4$ is hydrogen, or is chloro or bromo; and $R^5$ is pyridine, imidazole, or phenyl.

In a further more preferred embodiment there is provided a compound of formula (I) or a salt, solvate or physiologically functional derivative thereof wherein Y is N; X is $CR^1$ wherein $R^1$ is as defined above in which Ar is unsubstituted furan or thiazole; $R^3$ is benzyloxy or fluorobenzyloxy; $R^4$ is hydrogen, or is chloro or bromo; and $R^5$ is pyridine, imidazole, or phenyl.

In a most preferred embodiment there is provided a compound of formula (I) or a salt or solvate thereof wherein Y is $CR^2$, wherein $R^2$ is hydrogen, fluoro or methoxy; X is $CR^1$ wherein $R^1$ is as defined above in which Ar is unsubstituted furan or thiazole; $R^3$ is fluorobenzyloxy; $R^4$ is chloro or bromo; and $R^5$ is pyridine, imidazole, or phenyl.

In a further most preferred embodiment there is provided a compound of formula (I) or a salt or solvate thereof wherein Y is N; X is $CR^1$ wherein $R^1$ is as defined above in which Ar is unsubstituted furan or thiazole; $R^3$ is fluorobenzyloxy; $R^4$ is chloro or bromo; and $R^5$ is pyridine, imidazole, or phenyl.

Preferred compounds of the present invention include:
(4-(3-Fluorobenzyloxy)-3-chlorophenyl)-(6-(2-((2-phenyl-sulphonyl-ethylamino)-propyl)-furan-2-yl)-quinazolin-4-yl)-amine;
(4-(3-Fluorobenzyloxy)-3-chlorophenyl)-(6-(2-((2-(2-N-methylimidazolyl)-sulphonyl-ethylamino)-methyl)-furan-2-yl)-quinazolin-4-yl)-amine;
(4-(3-Fluorobenzyloxy)-phenyl)-(6-(2-((2-propanesulphonyl-ethylamino)methyl)-furan-2-yl)-pyrido[3,4-d]pyrimidin-4-yl)-amine;
(4-(3-Fluorobenzyloxy)-3-chlorophenyl)-(6-(2-((2-propane-sulphonyl-ethylamino)-methyl)-furan-2-yl)-quinazolin-4-yl)-amine;
(4-Benzyloxy-3-chlorophenyl)-(6-(2-((2-methanesulphonyl-ethylamino)propyl)-furan-2-yl)-quinazolin-4-yl)-amine;
(4-(3-Fluorobenzyloxy)-3-chlorophenyl)-(6-(2-((2-iso-propyl-sulphonyl-ethylamino)-propyl)-furan-2-yl)-quinazolin-4-yl)-amine;
(4-(3-Fluorobenzyloxy)-3-chlorophenyl)-(6-(2-((2-propane-sulphonyl-ethylamino)-propyl)-furan-2-yl)-quinazolin-4-yl)-amine;
(4-(3-Fluorobenzyloxy)-3-chlorophenyl)-(6-(2-((2-methanesulphonyl-ethylamino)ethyl)-thiazol-4-yl)-quinazolin-4-yl)-amine;
4-(3-Fluorobenzyloxy)-3-chlorophenyl)-(6-(2-((2-methanesulphonyl-ethylamino)ethyl)-furan-2-yl)-quinazolin-4-yl)-amine.

and salts or solvates thereof, particularly pharmaceutically acceptable salts or solvates thereof; and physiologically functional derivatives thereof.

Additional preferred compounds of the present invention include:
N-{3-chloro-4-[(3-fluorobenzyl)oxy]phenyl}-6-(5-{[2-(phenylsulfonyl)ethoxy]methyl}-2-furyl)-4-quinazolinamine;
(4-(3-Fluorobenzyloxy)-3-chlorophenyl)-(6-(2-((2-phenyl-sulphonyl-ethylamino)-methyl)-furan-2-yl)-quinazolin-4-yl)-amine;
(4-(3-Fluorobenzyloxy)-3-chlorophenyl)-(6-(2-((2-(2-pyridyl)-sulphonyl-ethylamino)-methyl)-furan-2-yl)-quinazolin-4-yl)-amine;
N-{3-chloro-4-[(3-fluorobenzyl)oxy]phenyl}-6-(5-{[2-(methylsulfonyl)ethoxy]methyl}-2-furyl)-4-quinazolinamine;
N-{3-chloro-4-[(3-fluorobenzyl)oxy]phenyl}-6-(5-{[2-(vinylsulfonyl)ethoxy]methyl}-2-furyl)-4-quinazolinamine;
2-{{[5-(4-{3-chloro-4-[(3-fluorobenzyl)oxy]ahilino}-6-quinazolinyl)-2-furyl]methyl}[2-(methylsulfonyl)ethyl]amino}acetonitrile;
6-[5-({benzyl[2-(methylsulfonyl)ethyl]amino}methyl)-2-furyl]-N-{3-chloro-4-[(3-fluorobenzyl)oxy]phenyl}-4-quinazolinamine;

N-{3-chloro-4-[(3-fluorobenzyl)oxy]phenyl}-6-[5-({ethyl [2-methylsulfonyl)ethyl]amino}methyl)-2-furyl]-4-quinazolinamine;

N-{3-chloro-4-[(3-fluorobenzyl)oxy]phenyl}-6-(5-{[[2-(methylsulfonyl)ethyl](propyl)amino]methyl}-2-furyl)-4-quinazolinamine;

(4-(3-Fluorobenzyloxy)-3-chlorophenyl)-(6-(2-((2-iso-propyl-sulphonyl-ethylamino)-methyl)-furan-2-yl)-quinazolin-4-yl)-amine;

and salts or solvates thereof, particularly pharmaceutically acceptable salts or solvates thereof; and physiologically functional derivatives thereof.

Other preferred compounds of the present invention include the following (in groups denoted hereafter as Lists 1 to 134):

List 1

(4-(3-Fluorobenzyloxy)-3-chlorophenyl)-(6-(2-((2-phenyl-sulphonyl-ethylamino)-methyl)-furan-2-yl)-pyrido[3,4-d]pyrimidin-4-yl)-amine;

(4-(3-Fluorobenzyloxy)-3-bromophenyl)-(6-(2-((2-phenyl-sulphonyl-ethylamino)-methyl)-furan-2-yl)-pyrido[3,4-d]pyrimidin-4-yl)-amine;

(4-(3-Fluorobenzyloxy)-3-chlorophenyl)-(6-(2-((2-phenyl-sulphonyl-ethylamino)-ethyl)-furan-2-yl)-pyrido[3,4-d]pyrimidin-4-yl)-amine;

(4-(3-Fluorobenzyloxy)-3-bromophenyl)-(6-(2-((2-phenyl-sulphonyl-ethylamino)-ethyl)-furan-2-yl)-pyrido[3,4-d]pyrimidin-4-yl)-amine;

(4-(3-Fluorobenzyloxy)-3-chlorophenyl)-(6-(2-((2-phenyl-sulphonyl-ethylamino)-propyl)-furan-2-yl)-pyrido[3,4-d]pyrimidin-4-yl)-amine;

(4-(3-Fluorobenzyloxy)-3-bromophenyl)-(6-(2-((2-phenyl-sulphonyl-ethylamino)-propyl)-furan-2-yl)-pyrido[3,4-d]pyrimidin-4-yl)-amine;

List 2

(4-(3-Fluorobenzyloxy)-3-chlorophenyl)-(6-(2-((2-phenyl-sulphonyl-ethylamino)methyl)-thiazol-4-yl)-pyrido[3,4-d]pyrimidin-4-yl)-amine;

(4-Benzyloxy-3-bromophenyl)-(6-(2-((2-phenylsulphonyl-ethylamino)methyl)-thiazol-4-yl)-pyrido[3,4-d]pyrimidin-4-yl)-amine;

(4-(3-Fluorobenzyloxy)-3-bromophenyl)-(6-(2-((2-phenyl-sulphonyl-ethylamino)methyl)-thiazol-4-yl)-pyrido[3,4-d]pyrimidin-4-yl)-amine;

(4-Benzyloxy-3-chlorophenyl)-(6-(2-((2-phenylsulphonyl-ethylamino)ethyl)-thiazol-4-yl)-pyrido[3,4-d]pyrimidin-4-yl)-amine;

(4-(3-Fluorobenzyloxy)-3-chlorophenyl)-(6-(2-((2-phenyl-sulphonyl-ethylamino)ethyl)-thiazol-4-yl)-pyrido[3,4-d]pyrimidin-4-yl)-amine;

(4-(3-Fluorobenzyloxy)-3-bromophenyl)-(6-(2-((2-phenyl-sulphonyl-ethylamino)ethyl)-thiazol-4-yl)-pyrido[3,4-d]pyrimidin-4-yl)-amine;

(4-(3-Fluorobenzyloxy)-3-chlorophenyl)-(6-(2-((2-phenyl-sulphonyl-ethylamino)propyl)-thiazol-4-yl)-pyrido[3,4-d]pyrimidin-4-yl)-amine;

(4-(3-Fluorobenzyloxy)-3-bromophenyl)-(6-(2-((2-phenyl-sulphonyl-ethylamino)propyl)-thiazol-4-yl)-pyrido[3,4-d]pyrimidin-4-yl)-amine;

List 3

(4-(3-Fluorobenzyloxy)-3-chlorophenyl)-(6-(2-((2-(2-py-ridyl)-sulphonyl-ethylamino)-methyl)-furan-2-yl)-pyrido[3,4-d]pyrimidin-4-yl)-amine;

(4-(3-Fluorobenzyloxy)-3-bromophenyl)-(6-(2-((2-(2-py-ridyl)-sulphonyl-ethylamino)-methyl)-furan-2-yl)-pyrido[3,4-d]pyrimidin-4-yl)-amine;

(4-(3-Fluorobenzyloxy)-3-chlorophenyl)-(6-(2-((2-(2-py-ridyl)-sulphonyl-ethylamino)-ethyl)-furan-2-yl)-pyrido[3,4-d]pyrimidin-4-yl)-amine;

(4-(3-Fluorobenzyloxy)-3-bromophenyl)-(6-(2-((2-(2-py-ridyl)-sulphonyl-ethylamino)-ethyl)-furan-2-yl)-pyrido[3,4-d]pyrimidin-4-yl)-amine;

(4-(3-Fluorobenzyloxy)-3-chlorophenyl)-(6-(2-((2-(2-py-ridyl)-sulphonyl-ethylamino)-propyl)-furan-2-yl)-pyrido[3,4-d]pyrimidin-4-yl)-amine;

(4-(3-Fluorobenzyloxy)-3-bromophenyl)-(6-(2-((2-(2-py-ridyl)-sulphonyl-ethylamino)-propyl)-furan-2-yl)-pyrido[3,4-d]pyrimidin-4-yl)-amine;

List 4

(4-(3-Fluorobenzyloxy)-3-chlorophenyl)-(6-(2-((2-(2-py-ridyl)-sulphonyl-ethylamino)methyl)-thiazol-4-yl)-py-rido[3,4-d]pyrimidin-4-yl)-amine;

(4-(3-Fluorobenzyloxy)-3-bromophenyl)-(6-(2-((2-(2-py-ridyl)-sulphonyl-ethylamino)methyl)-thiazol-4-yl)-py-rido[3,4-d]pyrimidin-4-yl)-amine;

(4-(3-Fluorobenzyloxy)-3-chlorophenyl)-(6-(2-((2-(2-py-ridyl)-sulphonyl-ethylamino)ethyl)-thiazol-4-yl)-pyrido[3,4-d]pyrimidin-4-yl)-amine;

(4-(3-Fluorobenzyloxy)-3-bromophenyl)-(6-(2-((2-(2-py-ridyl)-sulphonyl-ethylamino)ethyl)-thiazol-4-yl)-pyrido[3,4-d]pyrimidin-4-yl)-amine;

(4-(3-Fluorobenzyloxy)-3-chlorophenyl)-(6-(2-((2-(2-py-ridyl)-sulphonyl-ethylamino)propyl)-thiazol-4-yl)-pyrido[3,4-d]pyrimidin-4-yl)-amine;

(4-(3-Fluorobenzyloxy)-3-bromophenyl)-(6-(2-((2-(2-py-ridyl)-sulphonyl-ethylamino)propyl)-thiazol-4-yl)-pyrido[3,4-d]pyrimidin-4-yl)-amine;

List 5

(4-(3-Fluorobenzyloxy)-3-chlorophenyl)-(6-(2-((2-phenyl-sulphonyl-ethylamino)-methyl)-furan-2-yl)-pyrido[3,4-d]pyrimidin-4-yl)-amine;

(4-(3-Fluorobenzyloxy)-3-bromophenyl)-(6-(2-((2-phenyl-sulphonyl-ethoxy)-methyl)-furan-2-yl)-pyrido[3,4-d]py-rimidin-4-yl)-amine;

(4-(3-Fluorobenzyloxy)-3-chlorophenyl)-(6-(2-((2-phenyl-sulphonyl-ethylamino)-ethyl)-furan-2-yl)-pyrido[3,4-d]pyrimidin-4-yl)-amine;

(4-(3-Fluorobenzyloxy)-3-bromophenyl)-(6-(2-((2-phenyl-sulphonyl-ethoxy)-ethyl)-furan-2-yl)-pyrido[3,4-d]pyri-midin-4-yl)-amine;

(4-(3-Fluorobenzyloxy)-3-chlorophenyl)-(6-(2-((2-phenyl-sulphonyl-ethylamino)-propyl)-furan-2-yl)-pyrido[3,4-d]pyrimidin-4-yl)-amine;

(4-(3-Fluorobenzyloxy)-3-bromophenyl)-(6-(2-((2-phenyl-sulphonyl-ethoxy)-propyl)-furan-2-yl)-pyrido[3,4-d]pyri-midin-4-yl)-amine;

List 6

(4-(3-Fluorobenzyloxy)-3-chlorophenyl)-(6-(2-((2-phenyl-sulphonyl-ethoxy)methyl)-thiazol-4-yl)-pyrido[3,4-d]py-rimidin-4-yl)-amine;

(4-(3-Fluorobenzyloxy)-3-bromophenyl)-(6-(2-((2-phenyl-sulphonyl-ethoxy)methyl)-thiazol-4-yl)-pyrido[3,4-d]py-rimidin-4-yl)-amine;

(4-(3-Fluorobenzyloxy)-3-chlorophenyl)-(6-(2-((2-phenyl-sulphonyl-ethoxy)ethyl)-thiazol-4-yl)-pyrido[3,4-d]pyri-midin-4-yl)-amine;

(4-(3-Fluorobenzyloxy)-3-bromophenyl)-(6-(2-((2-phenyl-sulphonyl-ethoxy)ethyl)-thiazol-4-yl)-pyrido[3,4-d]pyrimidin-4-yl)-amine;
(4-(3-Fluorobenzyloxy)-3-chlorophenyl)-(6-(2-((2-phenyl-sulphonyl-ethoxy)propyl)-thiazol-4-yl)-pyrido[3,4-d]pyrimidin-4-yl)-amine;
(4-(3-Fluorobenzyloxy)-3-bromophenyl)-(6-(2-((2-phenyl-sulphonyl-ethoxy)propyl)-thiazol-4-yl)-pyrido[3,4-d]pyrimidin-4-yl)-amine;

List 7
(4-(3-Fluorobenzyloxy)-3-chlorophenyl)-(6-(2-((2-(2-pyridyl)-sulphonyl-ethylamino)-methyl)-furan-2-yl)-pyrido[3,4-d]pyrimidin-4-yl)-amine;
(4-(3-Fluorobenzyloxy)-3-bromophenyl)-(6-(2-((2-(2-pyridyl)-sulphonyl-ethoxy)-methyl)-furan-2-yl)-pyrido[3,4-d]pyrimidin-4-yl)-amine;
(4-(3-Fluorobenzyloxy)-3-chlorophenyl)-(6-(2-((2-(2-pyridyl)-sulphonyl-ethylamino)-ethyl)-furan-2-yl)-pyrido[3,4-d]pyrimidin-4-yl)-amine;
(4-(3-Fluorobenzyloxy)-3-bromophenyl)-(6-(2-((2-(2-pyridyl)-sulphonyl-ethoxy)-ethyl)-furan-2-yl)-pyrido[3,4-d]pyrimidin-4-yl)-amine;
(4-(3-Fluorobenzyloxy)-3-chlorophenyl)-(6-(2-((2-(2-pyridyl)-sulphonyl-ethylamino)-propyl)-furan-2-yl)-pyrido[3,4-d]pyrimidin-4-yl)-amine;
(4-(3-Fluorobenzyloxy)-3-bromophenyl)-(6-(2-((2-(2-pyridyl)-sulphonyl-ethoxy)-propyl)-furan-2-yl)-pyrido[3,4-d]pyrimidin-4-yl)-amine;

List 8
(4-(3-Fluorobenzyloxy)-3-chlorophenyl)-(6-(2-((2-(2-pyridyl)-sulphonyl-ethoxy)methyl)-thiazol-4-yl)-pyrido[3,4-d]pyrimidin-4-yl)-amine;
(4-(3-Fluorobenzyloxy)-3-bromophenyl)-(6-(2-((2-(2-pyridyl)-sulphonyl-ethoxy)methyl)-thiazol-4-yl)-pyrido[3,4-d]pyrimidin-4-yl)-amine;
(4-(3-Fluorobenzyloxy)-3-chlorophenyl)-(6-(2-((2-(2-pyridyl)-sulphonyl-ethoxy)ethyl)-thiazol-4-yl)-pyrido[3,4-d]pyrimidin-4-yl)-amine;
(4-(3-Fluorobenzyloxy)-3-bromophenyl)-(6-(2-((2-(2-pyridyl)-sulphonyl-ethoxy)ethyl)-thiazol-4-yl)-pyrido[3,4-d]pyrimidin-4-yl)-amine;
(4-(3-Fluorobenzyloxy)-3-chlorophenyl)-(6-(2-((2-(2-pyridyl)-sulphonyl-ethoxy)propyl)-thiazol-4-yl)-pyrido[3,4-d]pyrimidin-4-yl)-amine;
(4-(3-Fluorobenzyloxy)-3-bromophenyl)-(6-(2-((2-(2-pyridyl)-sulphonyl-ethoxy)propyl)-thiazol-4-yl)-pyrido[3,4-d]pyrimidin-4-yl)-amine;

List 9
(4-(3-Fluorobenzyloxy)-3-chlorophenyl)-(6-(2-((2-phenyl-sulphonyl-ethyl-N-methylamino)-methyl)-furan-2-yl)-pyrido[3,4-d]pyrimidin-4-yl)-amine;
(4-(3-Fluorobenzyloxy)-3-bromophenyl)-(6-(2-((2-phenyl-sulphonyl-ethyl-N-methylamino)-methyl)-furan-2-yl)-pyrido[3,4-d]pyrimidin-4-yl)-amine;
(4-(3-Fluorobenzyloxy)-3-chlorophenyl)-(6-(2-((2-phenyl-sulphonyl-ethyl-N-methylamino)-ethyl)-furan-2-yl)-pyrido[3,4-d]pyrimidin-4-yl)-amine;
(4-(3-Fluorobenzyloxy)-3-bromophenyl)-(6-(2-((2-phenyl-sulphonyl-ethyl-N-methylamino)-ethyl)-furan-2-yl)-pyrido[3,4-d]pyrimidin-4-yl)-amine;
(4-(3-Fluorobenzyloxy)-3-chlorophenyl)-(6-(2-((2-phenyl-sulphonyl-ethyl-N-methylamino)-propyl)-furan-2-yl)-pyrido[3,4-d]pyrimidin-4-yl)-amine;
(4-(3-Fluorobenzyloxy)-3-bromophenyl)-(6-(2-((2-phenyl-sulphonyl-ethyl-N-methylamino)-propyl)-furan-2-yl)-pyrido[3,4-d]pyrimidin-4-yl)-amine;

List 10
(4-(3-Fluorobenzyloxy)-3-chlorophenyl)-(6-(2-((2-phenyl-sulphonyl-ethyl-N-methylamino)-methyl)-thiazol-4-yl)-pyrido[3,4-d]pyrimidin-4-yl)-amine;
(4-(3-Fluorobenzyloxy)-3-bromophenyl)-(6-(2-((2-phenyl-sulphonyl-ethyl-N-methylamino)methyl)-thiazol-4-yl)-pyrido[3,4-d]pyrimidin-4-yl)-amine;
(4-(3-Fluorobenzyloxy)-3-chlorophenyl)-(6-(2-((2-phenyl-sulphonyl-ethyl-N-methylamino)-ethyl)-thiazol-4-yl)-pyrido[3,4-d]pyrimidin-4-yl)-amine;
(4-(3-Fluorobenzyloxy)-3-bromophenyl)-(6-(2-((2-phenyl-sulphonyl-ethyl-N-methylamino)ethyl)-thiazol-4-yl)-pyrido[3,4-d]pyrimidin-4-yl)-amine;
(4-(3-Fluorobenzyloxy)-3-chlorophenyl)-(6-(2-((2-phenyl-sulphonyl-ethyl-N-methylamino)-propyl)-thiazol-4-yl)-pyrido[3,4-d]pyrimidin-4-yl)-amine;
(4-(3-Fluorobenzyloxy)-3-bromophenyl)-(6-(2-((2-phenyl-sulphonyl-ethyl-N-methylamino)propyl)-thiazol-4-yl)-pyrido[3,4-d]pyrimidin-4-yl)-amine;

List 11
(4-(3-Fluorobenzyloxy)-3-chlorophenyl)-(6-(2-((2-(2-pyridyl)-sulphonyl-ethyl-N-methylamino)-methyl)-furan-2-yl)-pyrido[3,4-d]pyrimidin-4-yl)-amine;
(4-(3-Fluorobenzyloxy)-3-bromophenyl)-(6-(2-((2-(2-pyridyl)-sulphonyl-ethyl-N-methylamino)-methyl)-furan-2-yl)-pyrido[3,4-d]pyrimidin-4-yl)-amine;
(4-(3-Fluorobenzyloxy)-3-chlorophenyl)-(6-(2-((2-(2-pyridyl)-sulphonyl-ethyl-N-methylamino)-ethyl)-furan-2-yl)-pyrido[3,4-d]pyrimidin-4-yl)-amine;
(4-(3-Fluorobenzyloxy)-3-bromophenyl)-(6-(2-((2-(2-pyridyl)-sulphonyl-ethyl-N-methylamino)-ethyl)-furan-2-yl)-pyrido[3,4-d]pyrimidin-4-yl)-amine;
(4-(3-Fluorobenzyloxy)-3-chlorophenyl)-(6-(2-((2-(2-pyridyl)-sulphonyl-ethyl-N-methylamino)-propyl)-furan-2-yl)-pyrido[3,4-d]pyrimidin-4-yl)-amine;
(4-(3-Fluorobenzyloxy)-3-bromophenyl)-(6-(2-((2-(2-pyridyl)-sulphonyl-ethyl-N-methylamino)-propyl)-furan-2-yl)-pyrido[3,4-d]pyrimidin-4-yl)-amine;

List 12
(4-(3-Fluorobenzyloxy)-3-chlorophenyl)-(6-(2-((2-(2-pyridyl)-sulphonyl-ethyl-N-methylamino)-methyl)-thiazol-4-yl)-pyrido[3,4-d]pyrimidin-4-yl)-amine;
(4-(3-Fluorobenzyloxy)-3-bromophenyl)-(6-(2-((2-(2-pyridyl)-sulphonyl-ethyl-N-methylamino)methyl)-thiazol-4-yl)-pyrido[3,4-d]pyrimidin-4-yl)-amine;
(4-(3-Fluorobenzyloxy)-3-chlorophenyl)-(6-(2-((2-(2-pyridyl)-sulphonyl-ethyl-N-methylamino)-ethyl)-thiazol-4-yl)-pyrido[3,4-d]pyrimidin-4-yl)-amine;
(4-(3-Fluorobenzyloxy)-3-bromophenyl)-(6-(2-((2-(2-pyridyl)-sulphonyl-ethyl-N-methylamino)ethyl)-thiazol-4-yl)-pyrido[3,4-d]pyrimidin-4-yl)-amine;
(4-(3-Fluorobenzyloxy)-3-chlorophenyl)-(6-(2-((2-(2-pyridyl)-sulphonyl-ethyl-N-methylamino)-propyl)-thiazol-4-yl)-pyrido[3,4-d]pyrimidin-4-yl)-amine;
(4-(3-Fluorobenzyloxy)-3-bromophenyl)-(6-(2-((2-(2-pyridyl)-sulphonyl-ethyl-N-methylamino)propyl)-thiazol-4-yl)-pyrido[3,4-d]pyrimidin-4-yl)-amine;

List 13
(4-(3-Fluorobenzyloxy)-3-bromophenyl)-(6-(2-((2-phenyl-sulphonyl-ethylamino)-methyl)-furan-2-yl)-quinazolin-4-yl)-amine;

(4-(3-Fluorobenzyloxy)-3-chlorophenyl)-(6-(2-((2-phenyl-sulphonyl-ethylamino)-ethyl)-furan-2-yl)-quinazolin-4-yl)-amine;
(4-(3-Fluorobenzyloxy)-3-bromophenyl)-(6-(2-((2-phenyl-sulphonyl-ethylamino)-ethyl)-furan-2-yl)-quinazolin-4-yl)-amine;
(4-(3-Fluorobenzyloxy)-3-bromophenyl)-(6-(2-((2-phenyl-sulphonyl-ethylamino)-propyl)-furan-2-yl)-quinazolin-4-yl)-amine;

List 14
(4-(3-Fluorobenzyloxy)-3-chlorophenyl)-(6-(2-((2-phenyl-sulphonyl-ethylamino)methyl)-thiazol-4-yl)-quinazolin-4-yl)-amine;
(4-(3-Fluorobenzyloxy)-3-bromophenyl)-(6-(2-((2-phenyl-sulphonyl-ethylamino)methyl)-thiazol-4-yl)-quinazolin-4-yl)-amine;
(4-(3-Fluorobenzyloxy)-3-chlorophenyl)-(6-(2-((2-phenyl-sulphonyl-ethylamino)ethyl)-thiazol-4-yl)-quinazolin-4-yl)-amine;
(4-(3-Fluorobenzyloxy)-3-bromophenyl)-(6-(2-((2-phenyl-sulphonyl-ethylamino)ethyl)-thiazol-4-yl)-quinazolin-4-yl)-amine;
(4-(3-Fluorobenzyloxy)-3-chlorophenyl)-(6-(2-((2-phenyl-sulphonyl-ethylamino)propyl)-thiazol-4-yl)-quinazolin-4-yl)-amine;
(4-(3-Fluorobenzyloxy)-3-bromophenyl)-(6-(2-((2-phenyl-sulphonyl-ethylamino)propyl)-thiazol-4-yl)-quinazolin-4-yl)-amine;

List 15
(4-(3-Fluorobenzyloxy)-3-bromophenyl)-(6-(2-((2-(2-pyridyl)-sulphonyl-ethylamino)-methyl)-furan-2-yl)-quinazolin-4-yl)-amine;
(4-(3-Fluorobenzyloxy)-3-chlorophenyl)-(6-(2-((2-(2-pyridyl)-sulphonyl-ethylamino)-ethyl)-furan-2-yl)-quinazolin-4-yl)-amine;
(4-(3-Fluorobenzyloxy)-3-bromophenyl)-(6-(2-((2-(2-pyridyl)-sulphonyl-ethylamino)-ethyl)-furan-2-yl)-quinazolin-4-yl)-amine;
(4-(3-Fluorobenzyloxy)-3-chlorophenyl)-(6-(2-((2-(2-pyridyl)-sulphonyl-ethylamino)-propyl)-furan-2-yl)-quinazolin-4-yl)-amine;
(4-(3-Fluorobenzyloxy)-3-bromophenyl)-(6-(2-((2-(2-pyridyl)-sulphonyl-ethylamino)-propyl)-furan-2-yl)-quinazolin-4-yl)-amine;

List 16
(4-(3-Fluorobenzyloxy)-3-chlorophenyl)-(6-(2-((2-(2-pyridyl)-sulphonyl-ethylamino)methyl)-thiazol-4-yl)-quinazolin-4-yl)-amine;
(4-(3-Fluorobenzyloxy)-3-bromophenyl)-(6-(2-((2-(2-pyridyl)-sulphonyl-ethylamino)methyl)-thiazol-4-yl)-quinazolin-4-yl)-amine;
(4-(3-Fluorobenzyloxy)-3-chlorophenyl)-(6-(2-((2-(2-pyridyl)-sulphonyl-ethylamino)ethyl)-thiazol-4-yl)-quinazolin-4-yl)-amine;
(4-(3-Fluorobenzyloxy)-3-bromophenyl)-(6-(2-((2-(2-pyridyl)-sulphonyl-ethylamino)ethyl)-thiazol-4-yl)-quinazolin-4-yl)-amine;
(4-(3-Fluorobenzyloxy)-3-chlorophenyl)-(6-(2-((2-(2-pyridyl)-sulphonyl-ethylamino)propyl)-thiazol-4-yl)-quinazolin-4-yl)-amine;
(4-(3-Fluorobenzyloxy)-3-bromophenyl)-(6-(2-((2-(2-pyridyl)-sulphonyl-ethylamino)propyl)-thiazol-4-yl)-quinazolin-4-yl)-amine;

List 17
(4-(3-Fluorobenzyloxy)-3-chlorophenyl)-(6-(2-((2-phenyl-sulphonyl-ethylamino)-methyl)-furan-2-yl)-quinazolin-4-yl)-amine;
(4-(3-Fluorobenzyloxy)-3-bromophenyl)-(6-(2-((2-phenyl-sulphonyl-ethoxy)-methyl)-furan-2-yl)-quinazolin-4-yl)-amine;
(4-(3-Fluorobenzyloxy)-3-chlorophenyl)-(6-(2-((2-phenyl-sulphonyl-ethylamino)-ethyl)-furan-2-yl)-quinazolin-4-yl)-amine;
(4-(3-Fluorobenzyloxy)-3-bromophenyl)-(6-(2-((2-phenyl-sulphonyl-ethoxy)-ethyl)-furan-2-yl)-quinazolin-4-yl)-amine;
(4-(3-Fluorobenzyloxy)-3-bromophenyl)-(6-(2-((2-phenyl-sulphonyl-ethoxy)-propyl)-furan-2-yl)-quinazolin-4-yl)-amine;

List 18
(4-(3-Fluorobenzyloxy)-3-chlorophenyl)-(6-(2-((2-phenyl-sulphonyl-ethoxy)methyl)-thiazol-4-yl)-quinazolin-4-yl)-amine;
(4-(3-Fluorobenzyloxy)-3-bromophenyl)-(6-(2-((2-phenyl-sulphonyl-ethoxy)methyl)-thiazol-4-yl)-quinazolin-4-yl)-amine;
(4-(3-Fluorobenzyloxy)-3-chlorophenyl)-(6-(2-((2-phenyl-sulphonyl-ethoxy)ethyl)-thiazol-4-yl)-quinazolin-4-yl)-amine;
(4-(3-Fluorobenzyloxy)-3-bromophenyl)-(6-(2-((2-phenyl-sulphonyl-ethoxy)ethyl)-thiazol-4-yl)-quinazolin-4-yl)-amine;
(4-(3-Fluorobenzyloxy)-3-chlorophenyl)-(6-(2-((2-phenyl-sulphonyl-ethoxy)propyl)-thiazol-4-yl)-quinazolin-4-yl)-amine;
(4-(3-Fluorobenzyloxy)-3-bromophenyl)-(6-(2-((2-phenyl-sulphonyl-ethoxy)propyl)-thiazol-4-yl)-quinazolin-4-yl)-amine;

List 19
(4-(3-Fluorobenzyloxy)-3-chlorophenyl)-(6-(2-((2-(2-pyridyl)-sulphonyl-ethylamino)-methyl)-furan-2-yl)-quinazolin-4-yl)-amine;
(4-(3-Fluorobenzyloxy)-3-bromophenyl)-(6-(2-((2-(2-pyridyl)-sulphonyl-ethoxy)-methyl)-furan-2-yl)-quinazolin-4-yl)-amine;
(4-(3-Fluorobenzyloxy)-3-chlorophenyl)-(6-(2-((2-(2-pyridyl)-sulphonyl-ethylamino)-ethyl)-furan-2-yl)-quinazolin-4-yl)-amine;
(4-(3-Fluorobenzyloxy)-3-bromophenyl)-(6-(2-((2-(2-pyridyl)-sulphonyl-ethoxy)-ethyl)-furan-2-yl)-quinazolin-4-yl)-amine;
(4-(3-Fluorobenzyloxy)-3-chlorophenyl)-(6-(2-((2-(2-pyridyl)-sulphonyl-ethylamino)-propyl)-furan-2-yl)-quinazolin-4-yl)-amine;
(4-(3-Fluorobenzyloxy)-3-bromophenyl)-(6-(2-((2-(2-pyridyl)-sulphonyl-ethoxy)-propyl)-furan-2-yl)-quinazolin-4-yl)-amine;

List 20
(4-(3-Fluorobenzyloxy)-3-chlorophenyl)-(6-(2-((2-(2-pyridyl)-sulphonyl-ethoxy)methyl)-thiazol-4-yl)-quinazolin-4-yl)-amine;
(4-(3-Fluorobenzyloxy)-3-bromophenyl)-(6-(2-((2-(2-pyridyl)-sulphonyl-ethoxy)methyl)-thiazol-4-yl)-quinazolin-4-yl)-amine;
(4-(3-Fluorobenzyloxy)-3-chlorophenyl)-(6-(2-((2-(2-pyridyl)-sulphonyl-ethoxy)ethyl)-thiazol-4-yl)-quinazolin-4-yl)-amine;

(4-(3-Fluorobenzyloxy)-3-bromophenyl)-(6-(2-((2-(2-pyridyl)-sulphonyl-ethoxy)ethyl)-thiazol-4-yl)-quinazolin-4-yl)-amine;

(4-(3-Fluorobenzyloxy)-3-chlorophenyl)-(6-(2-((2-(2-pyridyl)-sulphonyl-ethoxy)propyl)-thiazol-4-yl)-quinazolin-4-yl)-amine;

(4-(3-Fluorobenzyloxy)-3-bromophenyl)-(6-(2-((2-(2-pyridyl)-sulphonyl-ethoxy)propyl)-thiazol-4-yl)-quinazolin-4-yl)-amine;

List 21

(4-(3-Fluorobenzyloxy)-3-chlorophenyl)-(6-(2-((2-phenyl-sulphonyl-ethyl-N-methylamino)-methyl)-furan-2-yl)-quinazolin-4-yl)-amine;

(4-(3-Fluorobenzyloxy)-3-bromophenyl)-(6-(2-((2-phenyl-sulphonyl-ethyl-N-methylamino)-methyl)-furan-2-yl)-quinazolin-4-yl)-amine;

(4-(3-Fluorobenzyloxy)-3-chlorophenyl)-(6-(2-((2-phenyl-sulphonyl-ethyl-N-methylamino)-ethyl)-furan-2-yl)-quinazolin-4-yl)-amine;

(4-(3-Fluorobenzyloxy)-3-bromophenyl)-(6-(2-((2-phenyl-sulphonyl-ethyl-N-methylamino)-ethyl)-furan-2-yl)-quinazolin-4-yl)-amine;

(4-(3-Fluorobenzyloxy)-3-chlorophenyl)-(6-(2-((2-phenyl-sulphonyl-ethyl-N-methylamino)-propyl)-furan-2-yl)-quinazolin-4-yl)-amine;

(4-(3-Fluorobenzyloxy)-3-bromophenyl)-(6-(2-((2-phenyl-sulphonyl-ethyl-N-methylamino)-propyl)-furan-2-yl)-quinazolin-4-yl)-amine;

List 22

(4-(3-Fluorobenzyloxy)-3-chlorophenyl)-(6-(2-((2-phenyl-sulphonyl-ethyl-N-methylamino)-methyl)-thiazol-4-yl)-quinazolin-4-yl)-amine;

(4-(3-Fluorobenzyloxy)-3-bromophenyl)-(6-(2-((2-phenyl-sulphonyl-ethyl-N-methylamino)methyl)-thiazol-4-yl)-quinazolin-4-yl)-amine;

(4-(3-Fluorobenzyloxy)-3-chlorophenyl)-(6-(2-((2-phenyl-sulphonyl-ethyl-N-methylamino)-ethyl)-thiazol-4-yl)-quinazolin-4-yl)-amine;

(4-(3-Fluorobenzyloxy)-3-bromophenyl)-(6-(2-((2-phenyl-sulphonyl-ethyl-N-methylamino)ethyl)-thiazol-4-yl)-quinazolin-4-yl)-amine;

(4-(3-Fluorobenzyloxy)-3-chlorophenyl)-(6-(2-((2-phenyl-sulphonyl-ethyl-N-methylamino)-propyl)-thiazol-4-yl)-quinazolin-4-yl)-amine;

(4-(3-Fluorobenzyloxy)-3-bromophenyl)-(6-(2-((2-phenyl-sulphonyl-ethyl-N-methylamino)propyl)-thiazol-4-yl)-quinazolin-4-yl)-amine;

List 23

(4-(3-Fluorobenzyloxy)-3-chlorophenyl)-(6-(2-((2-pyridyl)-sulphonyl-ethyl-N-methylamino)-methyl)-furan-2-yl)-quinazolin-4-yl)-amine;

(4-(3-Fluorobenzyloxy)-3-bromophenyl)-(6-(2-((2-pyridyl)-sulphonyl-ethyl-N-methylamino)-methyl)-furan-2-yl)-quinazolin-4-yl)-amine;

(4-(3-Fluorobenzyloxy)-3-chlorophenyl)-(6-(2-((2-pyridyl)-sulphonyl-ethyl-N-methylamino)-ethyl)-furan-2-yl)-quinazolin-4-yl)-amine;

(4-(3-Fluorobenzyloxy)-3-bromophenyl)-(6-(2-((2-pyridyl)-sulphonyl-ethyl-N-methylamino)-ethyl)-furan-2-yl)-quinazolin-4-yl)-amine;

(4-(3-Fluorobenzyloxy)-3-chlorophenyl)-(6-(2-((2-pyridyl)-sulphonyl-ethyl-N-methylamino)-propyl)-furan-2-yl)-quinazolin-4-yl)-amine;

(4-(3-Fluorobenzyloxy)-3-bromophenyl)-(6-(2-((2-pyridyl)-sulphonyl-ethyl-N-methylamino)-propyl)-furan-2-yl)-quinazolin-4-yl)-amine;

List 24

(4-(3-Fluorobenzyloxy)-3-chlorophenyl)-(6-(2-((2-pyridyl)-sulphonyl-ethyl-N-methylamino)-methyl)-thiazol-4-yl)-quinazolin-4-yl)-amine;

(4-(3-Fluorobenzyloxy)-3-bromophenyl)-(6-(2-((2-pyridyl)-sulphonyl-ethyl-N-methylamino)methyl)-thiazol-4-yl)-quinazolin-4-yl)-amine;

(4-(3-Fluorobenzyloxy)-3-chlorophenyl)-(6-(2-((2-pyridyl)-sulphonyl-ethyl-N-methylamino)-ethyl)-thiazol-4-yl)-quinazolin-4-yl)-amine;

(4-(3-Fluorobenzyloxy)-3-bromophenyl)-(6-(2-((2-pyridyl)-sulphonyl-ethyl-N-methylamino)ethyl)-thiazol-4-yl)-quinazolin-4-yl)-amine;

(4-(3-Fluorobenzyloxy)-3-chlorophenyl)-(6-(2-((2-pyridyl)-sulphonyl-ethyl-N-methylamino)-propyl)-thiazol-4-yl)-quinazolin-4-yl)-amine;

(4-(3-Fluorobenzyloxy)-3-bromophenyl)-(6-(2-((2-pyridyl)-sulphonyl-ethyl-N-methylamino)propyl)-thiazol-4-yl)-quinazolin-4-yl)-amine;

List 25

(4-(3-Fluorobenzyloxy)-3-chlorophenyl)-(6-(2-((2-phenyl-sulphonyl-ethylamino)-methyl)-furan-2-yl)-7-methoxy-quinazolin-4-yl)-amine;

(4-(3-Fluorobenzyloxy)-3-bromophenyl)-(6-(2-((2-phenyl-sulphonyl-ethylamino)-methyl)-furan-2-yl)-7-methoxy-quinazolin-4-yl)-amine;

(4-(3-Fluorobenzyloxy)-3-chlorophenyl)-(6-(2-((2-phenyl-sulphonyl-ethylamino)-ethyl)-furan-2-yl)-7-methoxy-quinazolin-4-yl)-amine;

(4-(3-Fluorobenzyloxy)-3-bromophenyl)-(6-(2-((2-phenyl-sulphonyl-ethylamino)-ethyl)-furan-2-yl)-7-methoxy-quinazolin-4-yl)-amine;

(4-(3-Fluorobenzyloxy)-3-chlorophenyl)-(6-(2-((2-phenyl-sulphonyl-ethylamino)-propyl)-furan-2-yl)-7-methoxy-quinazolin-4-yl)-amine;

(4-(3-Fluorobenzyloxy)-3-bromophenyl)-(6-(2-((2-phenyl-sulphonyl-ethylamino)-propyl)-furan-2-yl)-7-methoxy-quinazolin-4-yl)-amine;

List 26

(4-(3-Fluorobenzyloxy)-3-chlorophenyl)-(6-(2-((2-phenyl-sulphonyl-ethylaminomethyl)-thiazol-4-yl)-7-methoxy-quinazolin-4-yl)-amine;

(4-(3-Fluorobenzyloxy)-3-bromophenyl)-(6-(2-((2-phenyl-sulphonyl-ethylamino)methyl)-thiazol-4-yl)-7-methoxy-quinazolin-4-yl)-amine;

(4-(3-Fluorobenzyloxy)-3-chlorophenyl)-(6-(2-((2-phenyl-sulphonyl-ethylamino)ethyl)-thiazol-4-yl)-7-methoxy-quinazolin-4-yl)-amine;

(4-(3-Fluorobenzyloxy)-3-bromophenyl)-(6-(2-((2-phenyl-sulphonyl-ethylamino)ethyl)-thiazol-4-yl)-7-methoxy-quinazolin-4-yl)-amine;

(4-(3-Fluorobenzyloxy)-3-chlorophenyl)-(6-(2-((2-phenyl-sulphonyl-ethylamino)propyl)-thiazol-4-yl)-7-methoxy-quinazolin-4-yl)-amine;

(4-(3-Fluorobenzyloxy)-3-bromophenyl)-(6-(2-((2-phenyl-sulphonyl-ethylamino)propyl)-thiazol-4-yl)-7-methoxy-quinazolin-4-yl)-amine;

List 27

(4-(3-Fluorobenzyloxy)-3-chlorophenyl)-(6-(2-((2-(2-pyridyl)-sulphonyl-ethylamino)-methyl)-furan-2-yl)-7-methoxy-quinazolin-4-yl)-amine;

(4-(3-Fluorobenzyloxy)-3-bromophenyl)-(6-(2-((2-(2-pyridyl)-sulphonyl-ethylamino)-methyl)-furan-2-yl)-7-methoxy-quinazolin-4-yl)-amine;
(4-(3-Fluorobenzyloxy)-3-chlorophenyl)-(6-(2-((2-(2-pyridyl)-sulphonyl-ethylamino)-ethyl)-furan-2-yl)-7-methoxy-quinazolin-4-yl)-amine;
(4-(3-Fluorobenzyloxy)-3-bromophenyl)-(6-(2-((2-(2-pyridyl)-sulphonyl-ethylamino)-ethyl)-furan-2-yl)-7-methoxy-quinazolin-4-yl)-amine;
(4-(3-Fluorobenzyloxy)-3-chlorophenyl)-(6-(2-((2-(2-pyridyl)-sulphonyl-ethylamino)-propyl)-furan-2-yl)-7-methoxy-quinazolin-4-yl)-amine;
(4-(3-Fluorobenzyloxy)-3-bromophenyl)-(6-(2-((2-(2-pyridyl)-sulphonyl-ethylamino)-propyl)-furan-2-yl)-7-methoxy-quinazolin-4-yl)-amine;

List 28
(4-(3-Fluorobenzyloxy)-3-chlorophenyl)-(6-(2-((2-(2-pyridyl)-sulphonyl-ethylamino)methyl)-thiazol-4-yl)-7-methoxy-quinazolin-4-yl)-amine;
(4-(3-Fluorobenzyloxy)-3-bromophenyl)-(6-(2-((2-(2-pyridyl)-sulphonyl-ethylamino)methyl)-thiazol-4-yl)-7-methoxy-quinazolin-4-yl)-amine;
(4-(3-Fluorobenzyloxy)-3-chlorophenyl)-(6-(2-((2-(2-pyridyl)-sulphonyl-ethylamino)ethyl)-thiazol-4-yl)-7-methoxy-quinazolin-4-yl)-amine;
(4-(3-Fluorobenzyloxy)-3-bromophenyl)-(6-(2-((2-(2-pyridyl)-sulphonyl-ethylamino)ethyl)-thiazol-4-yl)-7-methoxy-quinazolin-4-yl)-amine;
(4-(3-Fluorobenzyloxy)-3-chlorophenyl)-(6-(2-((2-(2-pyridyl)-sulphonyl-ethylamino)propyl)-thiazol-4-yl)-7-methoxy-quinazolin-4-yl)-amine;
(4-(3-Fluorobenzyloxy)-3-bromophenyl)-(6-(2-((2-(2-pyridyl)-sulphonyl-ethylamino)propyl)-thiazol-4-yl)-7-methoxy-quinazolin-4-yl)-amine;

List 29
(4-(3-Fluorobenzyloxy)-3-chlorophenyl)-(6-(2-((2-phenyl-sulphonyl-ethylamino)-methyl)-furan-2-yl)-7-methoxy-quinazolin-4-yl)-amine;
(4-(3-Fluorobenzyloxy)-3-bromophenyl)-(6-(2-((2-phenyl-sulphonyl-ethoxy)-methyl)-furan-2-yl)-7-methoxy-quinazolin-4-yl)-amine;
(4-(3-Fluorobenzyloxy)-3-chlorophenyl)-(6-(2-((2-phenyl-sulphonyl-ethylamino)-ethyl)-furan-2-yl)-7-methoxy-quinazolin-4-yl)-amine;
(4-(3-Fluorobenzyloxy)-3-bromophenyl)-(6-(2-((2-phenyl-sulphonyl-ethoxy)-ethyl)-furan-2-yl)-7-methoxy-quinazolin-4-yl)-amine;
(4-(3-Fluorobenzyloxy)-3-chlorophenyl)-(6-(2-((2-phenyl-sulphonyl-ethylamino)-propyl)-furan-2-yl)-7-methoxy-quinazolin-4-yl)-amine;
(4-(3-Fluorobenzyloxy)-3-bromophenyl)-(6-(2-((2-phenyl-sulphonyl-ethoxy)-propyl)-furan-2-yl)-7-methoxy-quinazolin-4-yl)-amine;

List 30
(4-(3-Fluorobenzyloxy)-3-chlorophenyl)-(6-(2-((2-phenyl-sulphonyl-ethoxy)methyl)-thiazol-4-yl)-7-methoxy-quinazolin-4-yl)-amine;
(4-(3-Fluorobenzyloxy)-3-bromophenyl)-(6-(2-((2-phenyl-sulphonyl-ethoxy)methyl)-thiazol-4-yl)-7-methoxy-quinazolin-4-yl)-amine;
(4-(3-Fluorobenzyloxy)-3-chlorophenyl)-(6-(2-((2-phenyl-sulphonyl-ethoxy)ethyl)-thiazol-4-yl)-7-methoxy-quinazolin-4-yl)-amine;
(4-(3-Fluorobenzyloxy)-3-bromophenyl)-(6-(2-((2-phenyl-sulphonyl-ethoxy)ethyl)-thiazol-4-yl)-7-methoxy-quinazolin-4-yl)-amine;
(4-(3-Fluorobenzyloxy)-3-chlorophenyl)-(6-(2-((2-phenyl-sulphonyl-ethoxy)propyl)-thiazol-4-yl)-7-methoxy-quinazolin-4-yl)-amine;
(4-(3-Fluorobenzyloxy)-3-bromophenyl)-(6-(2-((2-phenyl-sulphonyl-ethoxy)propyl)-thiazol-4-yl)-7-methoxy-quinazolin-4-yl)-amine;

List 31
(4-(3-Fluorobenzyloxy)-3-chlorophenyl)-(6-(2-((2-(2-pyridyl)-sulphonyl-ethylamino)-methyl)-furan-2-yl)-7-methoxy-quinazolin-4-yl)-amine;
(4-(3-Fluorobenzyloxy)-3-bromophenyl)-(6-(2-((2-(2-pyridyl)-sulphonyl-ethoxy)-methyl)-furan-2-yl)-7-methoxy-quinazolin-4-yl)-amine;
(4-(3-Fluorobenzyloxy)-3-chlorophenyl)-(6-(2-((2-(2-pyridyl)-sulphonyl-ethylamino)-ethyl)-furan-2-yl)-7-methoxy-quinazolin-4-yl)-amine;
(4-(3-Fluorobenzyloxy)-3-bromophenyl)-(6-(2-((2-(2-pyridyl)-sulphonyl-ethoxy)-ethyl)-furan-2-yl)-7-methoxy-quinazolin-4-yl)-amine;
(4-(3-Fluorobenzyloxy)-3-chlorophenyl)-(6-(2-((2-(2-pyridyl)-sulphonyl-ethylamino)-propyl)-furan-2-yl)-7-methoxy-quinazolin-4-yl)-amine;
(4-(3-Fluorobenzyloxy)-3-bromophenyl)-(6-(2-((2-(2-pyridyl)-sulphonyl-ethoxy)-propyl)-furan-2-yl)-7-methoxy-quinazolin-4-yl)-amine;

List 32
(4-(3-Fluorobenzyloxy)-3-chlorophenyl)-(6-(2-((2-(2-pyridyl)-sulphonyl-ethoxy)methyl)-thiazol-4-yl)-7-methoxy-quinazolin-4-yl)-amine;
(4-(3-Fluorobenzyloxy)-3-bromophenyl)-(6-(2-((2-(2-pyridyl)-sulphonyl-ethoxy)methyl)-thiazol-4-yl)-7-methoxy-quinazolin-4-yl)-amine;
(4-(3-Fluorobenzyloxy)-3-chlorophenyl)-(6-(2-((2-(2-pyridyl)-sulphonyl-ethoxy)ethyl)-thiazol-4-yl)-7-methoxy-quinazolin-4-yl)-amine;
(4-(3-Fluorobenzyloxy)-3-chlorophenyl)-(6-(2-((2-(2-pyridyl)-sulphonyl-ethoxy)propyl)-thiazol-4-yl)-7-methoxy-quinazolin-4-yl)-amine;
(4-(3-Fluorobenzyloxy)-3-bromophenyl)-(6-(2-((2-(2-pyridyl)-sulphonyl-ethoxy)propyl)-thiazol-4-yl)-7-methoxy-quinazolin-4-yl)-amine;

List 33
(4-(3-Fluorobenzyloxy)-3-chlorophenyl)-(6-(2-((2-phenyl-sulphonyl-ethyl-N-methylamino)-methyl)-furan-2-yl)-7-methoxy-quinazolin-4-yl)-amine;
(4-(3-Fluorobenzyloxy)-3-bromophenyl)-(6-(2-((2-phenyl-sulphonyl-ethyl-N-methylamino)-methyl)-furan-2-yl)-7-methoxy-quinazolin-4-yl)-amine;
(4-(3-Fluorobenzyloxy)-3-chlorophenyl)-(6-(2-((2-phenyl-sulphonyl-ethyl-N-methylamino)-ethyl)-furan-2-yl)-7-methoxy-quinazolin-4-yl)-amine;
(4-(3-Fluorobenzyloxy)-3-chlorophenyl)-(6-(2-((2-phenyl-sulphonyl-ethyl-N-methylamino)-propyl)-furan-2-yl)-7-methoxy-quinazolin-4-yl)-amine;
(4-(3-Fluorobenzyloxy)-3-bromophenyl)-(6-(2-((2-phenyl-sulphonyl-ethyl-N-methylamino)-propyl)-furan-2-yl)-7-methoxy-quinazolin-4-yl)-amine;

List 34
(4-(3-Fluorobenzyloxy)-3-chlorophenyl)-(6-(2-((2-phenyl-sulphonyl-ethyl-N-methylamino)-methyl)-thiazol-4-yl)-7-methoxy-quinazolin-4-yl)-amine;

(4-(3-Fluorobenzyloxy)-3-bromophenyl)-(6-(2-((2-phenyl-sulphonyl-ethyl-N-methylamino)methyl)-thiazol-4-yl)-7-methoxy-quinazolin-4-yl)-amine;
(4-(3-Fluorobenzyloxy)-3-chlorophenyl)-(6-(2-((2-phenyl-sulphonyl-ethyl-N-methylamino)-ethyl)-thiazol-4-yl)-7-methoxy-quinazolin-4-yl)-amine;
(4-(3-Fluorobenzyloxy)-3-bromophenyl)-(6-(2-((2-phenyl-sulphonyl-ethyl-N-methylamino)ethyl)-thiazol-4-yl)-7-methoxy-quinazolin-4-yl)-amine;
(4-(3-Fluorobenzyloxy)-3-chlorophenyl)-(6-(2-((2-phenyl-sulphonyl-ethyl-N-methylamino)-propyl)-thiazol-4-yl)-7-methoxy-quinazolin-4-yl)-amine;
(4-(3-Fluorobenzyloxy)-3-bromophenyl)-(6-(2-((2-phenyl-sulphonyl-ethyl-N-methylamino)propyl)-thiazol-4-yl)-7-methoxy-quinazolin-4-yl)-amine;

List 35
(4-(3-Fluorobenzyloxy)-3-chlorophenyl)-(6-(2-((2-(2-pyridyl)-sulphonyl-ethyl-N-methylamino)-methyl)-furan-2-yl)-7-methoxy-quinazolin-4-yl)-amine;
(4-(3-Fluorobenzyloxy)-3-bromophenyl)-(6-(2-((2-(2-pyridyl)-sulphonyl-ethyl-N-methylamino)-methyl)-furan-2-yl)-7-methoxy-quinazolin-4-yl)-amine;
(4-(3-Fluorobenzyloxy)-3-chlorophenyl)-(6-(2-((2-(2-pyridyl)-sulphonyl-ethyl-N-methylamino)-ethyl)-furan-2-yl)-7-methoxy-quinazolin-4-yl)-amine;
(4-(3-Fluorobenzyloxy)-3-bromophenyl)-(6-(2-((2-(2-pyridyl)-sulphonyl-ethyl-N-methylamino)-ethyl)-furan-2-yl)-7-methoxy-quinazolin-4-yl)-amine;
(4-(3-Fluorobenzyloxy)-3-chlorophenyl)-(6-(2-((2-(2-pyridyl)-sulphonyl-ethyl-N-methylamino)-propyl)-furan-2-yl)-7-methoxy-quinazolin-4-yl)-amine;
(4-(3-Fluorobenzyloxy)-3-bromophenyl)-(6-(2-((2-(2-pyridyl)-sulphonyl-ethyl-N-methylamino)-propyl)-furan-2-yl)-7-methoxy-quinazolin-4-yl)-amine;

List 36
(4-(3-Fluorobenzyloxy)-3-chlorophenyl)-(6-(2-((2-(2-pyridyl)-sulphonyl-ethyl-N-methylamino)-methyl)-thiazol-4-yl)-7-methoxy-quinazolin-4-yl)-amine;
(4-(3-Fluorobenzyloxy)-3-bromophenyl)-(6-(2-((2-(2-pyridyl)-sulphonyl-ethyl-N-methylamino)methyl)-thiazol-4-yl)-7-methoxy-quinazolin-4-yl)-amine;
(4-(3-Fluorobenzyloxy)-3-chlorophenyl)-(6-(2-((2-(2-pyridyl)-sulphonyl-ethyl-N-methylamino)-ethyl)-thiazol-4-yl)-7-methoxy-quinazolin-4-yl)-amine;
(4-(3-Fluorobenzyloxy)-3-bromophenyl)-(6-(2-((2-(2-pyridyl)-sulphonyl-ethyl-N-methylamino)ethyl)-thiazol-4-yl)-7-methoxy-quinazolin-4-yl)-amine;
(4-(3-Fluorobenzyloxy)-3-chlorophenyl)-(6-(2-((2-(2-pyridyl)-sulphonyl-ethyl-N-methylamino)-propyl)-thiazol-4-yl)-7-methoxy-quinazolin-4-yl)-amine;
(4-(3-Fluorobenzyloxy)-3-bromophenyl)-(6-(2-((2-(2-pyridyl)-sulphonyl-ethyl-N-methylamino)propyl)-thiazol-4-yl)-7-methoxy-quinazolin-4-yl)-amine;

List 37
(4-(3-Fluorobenzyloxy)-3-chlorophenyl)-(6-(2-((2-phenyl-sulphonyl-ethylamino)-methyl)-furan-2-yl)-7-fluoro-quinazolin-4-yl)-amine;
(4-(3-Fluorobenzyloxy)-3-bromophenyl)-(6-(2-((2-phenyl-sulphonyl-ethylamino)-methyl)-furan-2-yl)-7-fluoro-quinazolin-4-yl)-amine;
(4-(3-Fluorobenzyloxy)-3-chlorophenyl)-(6-(2-((2-phenyl-sulphonyl-ethylamino)-ethyl)-furan-2-yl)-7-fluoro-quinazolin-4-yl)-amine;
(4-(3-Fluorobenzyloxy)-3-bromophenyl)-(6-(2-((2-phenyl-sulphonyl-ethylamino)-ethyl)-furan-2-yl)-7-fluoro-quinazolin-4-yl)-amine;
(4-(3-Fluorobenzyloxy)-3-chlorophenyl)-(6-(2-((2-phenyl-sulphonyl-ethylamino)-propyl)-furan-2-yl)-7-fluoro-quinazolin-4-yl)-amine;
(4-(3-Fluorobenzyloxy)-3-bromophenyl)-(6-(2-((2-phenyl-sulphonyl-ethylamino)-propyl)-furan-2-yl)-7-fluoro-quinazolin-4-yl)-amine;

List 38
(4-(3-Fluorobenzyloxy)-3-chlorophenyl)-(6-(2-((2-phenyl-sulphonyl-ethylamino)methyl)-thiazol-4-yl)-7-fluoro-quinazolin-4-yl)-amine;
(4-(3-Fluorobenzyloxy)-3-bromophenyl)-(6-(2-((2-phenyl-sulphonyl-ethylamino)methyl)-thiazol-4-yl)-7-fluoro-quinazolin-4-yl)-amine;
(4-(3-Fluorobenzyloxy)-3-chlorophenyl)-(6-(2-((2-phenyl-sulphonyl-ethylamino)ethyl)-thiazol-4-yl)-7-fluoro-quinazolin-4-yl)-amine;
(4-(3-Fluorobenzyloxy)-3-bromophenyl)-(6-(2-((2-phenyl-sulphonyl-ethylamino)ethyl)-thiazol-4-yl)-7-fluoro-quinazolin-4-yl)-amine;
(4-(3-Fluorobenzyloxy)-3-chlorophenyl)-(6-(2-((2-phenyl-sulphonyl-ethylamino)propyl)-thiazol-4-yl)-7-fluoro-quinazolin-4-yl)-amine;
(4-(3-Fluorobenzyloxy)-3-bromophenyl)-(6-(2-((2-phenyl-sulphonyl-ethylamino)propyl)-thiazol-4-yl)-7-fluoro-quinazolin-4-yl)-amine;

List 39
(4-(3-Fluorobenzyloxy)-3-chlorophenyl)-(6-(2-((2-(2-pyridyl)-sulphonyl-ethylamino)-methyl)-furan-2-yl)-7-fluoro-quinazolin-4-yl)-amine;
(4-(3-Fluorobenzyloxy)-3-bromophenyl)-(6-(2-((2-(2-pyridyl)-sulphonyl-ethylamino)-methyl)-furan-2-yl)-7-fluoro-quinazolin-4-yl)-amine;
(4-(3-Fluorobenzyloxy)-3-chlorophenyl)-(6-(2-((2-(2-pyridyl)-sulphonyl-ethylamino)-ethyl)-furan-2-yl)-7-fluoro-quinazolin-4-yl)-amine;
(4-(3-Fluorobenzyloxy)-3-bromophenyl)-(6-(2-((2-(2-pyridyl)-sulphonyl-ethylamino)-ethyl)-furan-2-yl)-7-fluoro-quinazolin-4-yl)-amine;
(4-(3-Fluorobenzyloxy)-3-chlorophenyl)-(6-(2-((2-(2-pyridyl)-sulphonyl-ethylamino)-propyl)-furan-2-yl)-7-fluoro-quinazolin-4-yl)-amine;
(4-(3-Fluorobenzyloxy)-3-bromophenyl)-(6-(2-((2-(2-pyridyl)-sulphonyl-ethylamino)-propyl)-furan-2-yl)-7-fluoro-quinazolin-4-yl)-amine;

List 40
(4-(3-Fluorobenzyloxy)-3-chlorophenyl)-(6-(2-((2-(2-pyridyl)-sulphonyl-ethylamino)methyl)-thiazol-4-yl)-7-fluoro-quinazolin-4-yl)-amine;
(4-(3-Fluorobenzyloxy)-3-bromophenyl)-(6-(2-((2-(2-pyridyl)-sulphonyl-ethylamino)methyl)-thiazol-4-yl)-7-fluoro-quinazolin-4-yl)-amine;
(4-(3-Fluorobenzyloxy)-3-chlorophenyl)-(6-(2-((2-(2-pyridyl)-sulphonyl-ethylamino)ethyl)-thiazol-4-yl)-7-fluoro-quinazolin-4-yl)-amine;
(4-(3-Fluorobenzyloxy)-3-bromophenyl)-(6-(2-((2-(2-pyridyl)-sulphonyl-ethylamino)ethyl)-thiazol-4-yl)-7-fluoro-quinazolin-4-yl)-amine;
(4-(3-Fluorobenzyloxy)-3-chlorophenyl)-(6-(2-((2-(2-pyridyl)-sulphonyl-ethylamino)propyl)-thiazol-4-yl)-7-fluoro-quinazolin-4-yl)-amine;

(4-(3-Fluorobenzyloxy)-3-bromophenyl)-(6-(2-((2-(2-pyridyl)-sulphonyl-ethylamino)propyl)-thiazol-4-yl)-7-fluoro-quinazolin-4-yl)-amine;

List 41
(4-(3-Fluorobenzyloxy)-3-chlorophenyl)-(6-(2-((2-phenyl-sulphonyl-ethylamino)-methyl)-furan-2-yl)-7-fluoro-quinazolin-4-yl)-amine;
(4-(3-Fluorobenzyloxy)-3-bromophenyl)-(6-(2-((2-phenyl-sulphonyl-ethoxy)-methyl)-furan-2-yl)-7-fluoro-quinazolin-4-yl)-amine;
(4-(3-Fluorobenzyloxy)-3-chlorophenyl)-(6-(2-((2-phenyl-sulphonyl-ethylamino)-ethyl)-furan-2-yl)-7-fluoro-quinazolin-4-yl)-amine;
(4-(3-Fluorobenzyloxy)-3-bromophenyl)-(6-(2-((2-phenyl-sulphonyl-ethoxy)-ethyl)-furan-2-yl)-7-fluoro-quinazolin-4-yl)-amine;
(4-(3-Fluorobenzyloxy)-3-chlorophenyl)-(6-(2-((2-phenyl-sulphonyl-ethylamino)-propyl)-furan-2-yl)-7-fluoro-quinazolin-4-yl)-amine;
(4-(3-Fluorobenzyloxy)-3-bromophenyl)-(6-(2-((2-phenyl-sulphonyl-ethoxy)-propyl)-furan-2-yl)-7-fluoro-quinazolin-4-yl)-amine;

List 42
(4-(3-Fluorobenzyloxy)-3-chlorophenyl)-(6-(2-((2-phenyl-sulphonyl-ethoxy)methyl)-thiazol-4-yl)-7-fluoro-quinazolin-4-yl)-amine;
(4-(3-Fluorobenzyloxy)-3-bromophenyl)-(6-(2-((2-phenyl-sulphonyl-ethoxy)methyl)-thiazol-4-yl)-7-fluoro-quinazolin-4-yl)-amine;
(4-(3-Fluorobenzyloxy)-3-chlorophenyl)-(6-(2-((2-phenyl-sulphonyl-ethoxy)ethyl)-thiazol-4-yl)-7-fluoro-quinazolin-4-yl)-amine;
(4-(3-Fluorobenzyloxy)-3-bromophenyl)-(6-(2-((2-phenyl-sulphonyl-ethoxy)ethyl)-thiazol-4-yl)-7-fluoro-quinazolin-4-yl)-amine;
(4-(3-Fluorobenzyloxy)-3-chlorophenyl)-(6-(2-((2-phenyl-sulphonyl-ethoxy)propyl)-thiazol-4-yl)-7-fluoro-quinazolin-4-yl)-amine;
(4-(3-Fluorobenzyloxy)-3-bromophenyl)-(6-(2-((2-phenyl-sulphonyl-ethoxy)propyl)-thiazol-4-yl)-7-fluoro-quinazolin-4-yl)-amine;

List 43
(4-(3-Fluorobenzyloxy)-3-chlorophenyl)-(6-(2-((2-(2-pyridyl)-sulphonyl-ethylamino)-methyl)-furan-2-yl)-7-fluoro-quinazolin-4-yl)-amine;
(4-(3-Fluorobenzyloxy)-3-bromophenyl)-(6-(2-((2-(2-pyridyl)-sulphonyl-ethoxy)-methyl)-furan-2-yl)-7-fluoro-quinazolin-4-yl)-amine;
(4-(3-Fluorobenzyloxy)-3-chlorophenyl)-(6-(2-((2-(2-pyridyl)-sulphonyl-ethylamino)-ethyl)-furan-2-yl)-7-fluoro-quinazolin-4-yl)-amine;
(4-(3-Fluorobenzyloxy)-3-bromophenyl)-(6-(2-((2-(2-pyridyl)-sulphonyl-ethoxy)-ethyl)-furan-2-yl)-7-fluoro-quinazolin-4-yl)-amine;
(4-(3-Fluorobenzyloxy)-3-chlorophenyl)-(6-(2-((2-(2-pyridyl)-sulphonyl-ethylamino)-propyl)-furan-2-yl)-7-fluoro-quinazolin-4-yl)-amine;
(4-(3-Fluorobenzyloxy)-3-bromophenyl)-(6-(2-((2-(2-pyridyl)-sulphonyl-ethoxy)-propyl)-furan-2-yl)-7-fluoro-quinazolin-4-yl)-amine;

List 44
(4-(3-Fluorobenzyloxy)-3-chlorophenyl)-(6-(2-((2-(2-pyridyl)-sulphonyl-ethoxy)methyl)-thiazol-4-yl)-7-fluoro-quinazolin-4-yl)-amine;
(4-(3-Fluorobenzyloxy)-3-bromophenyl)-(6-(2-((2-(2-pyridyl)-sulphonyl-ethoxy)methyl)-thiazol-4-yl)-7-fluoro-quinazolin-4-yl)-amine;
(4-(3-Fluorobenzyloxy)-3-chlorophenyl)-(6-(2-((2-(2-pyridyl)-sulphonyl-ethoxy)ethyl)-thiazol-4-yl)-7-fluoro-quinazolin-4-yl)-amine;
(4-(3-Fluorobenzyloxy)-3-bromophenyl)-(6-(2-((2-(2-pyridyl)-sulphonyl-ethoxy)ethyl)-thiazol-4-yl)-7-fluoro-quinazolin-4-yl)-amine;
(4-(3-Fluorobenzyloxy)-3-chlorophenyl)-(6-(2-((2-(2-pyridyl)-sulphonyl-ethoxy)propyl)-thiazol-4-yl)-7-fluoro-quinazolin-4-yl)-amine;
(4-(3-Fluorobenzyloxy)-3-bromophenyl)-(6-(2-((2-(2-pyridyl)-sulphonyl-ethoxy)propyl)-thiazol-4-yl)-7-fluoro-quinazolin-4-yl)-amine;

List 45
(4-(3-Fluorobenzyloxy)-3-chlorophenyl)-(6-(2-((2-phenyl-sulphonyl-ethyl-N-methylamino)-methyl)-furan-2-yl)-7-fluoro-quinazolin-4-yl)-amine;
(4-(3-Fluorobenzyloxy)-3-bromophenyl)-(6-(2-((2-phenyl-sulphonyl-ethyl-N-methylamino)-methyl)-furan-2-yl)-7-fluoro-quinazolin-4-yl)-amine;
(4-(3-Fluorobenzyloxy)-3-chlorophenyl)-(6-(2-((2-phenyl-sulphonyl-ethyl-N-methylamino)-ethyl)-furan-2-yl)-7-fluoro-quinazolin-4-yl)-amine;
(4-(3-Fluorobenzyloxy)-3-bromophenyl)-(6-(2-((2-phenyl-sulphonyl-ethyl-N-methylamino)-ethyl)-furan-2-yl)-7-fluoro-quinazolin-4-yl)-amine;
(4-(3-Fluorobenzyloxy)-3-chlorophenyl)-(6-(2-((2-phenyl-sulphonyl-ethyl-N-methylamino)-propyl)-furan-2-yl)-7-fluoro-quinazolin-4-yl)-amine;
(4-(3-Fluorobenzyloxy)-3-bromophenyl)-(6-(2-((2-phenyl-sulphonyl-ethyl-N-methylamino)-propyl)-furan-2-yl)-7-fluoro-quinazolin-4-yl)-amine;

List 46
(4-(3-Fluorobenzyloxy)-3-chlorophenyl)-(6-(2-((2-phenyl-sulphonyl-ethyl-N-methylamino)-methyl)-thiazol -4-yl)-7-fluoro-quinazolin-4-yl)-amine;
(4-(3-Fluorobenzyloxy)-3-bromophenyl)-(6-(2-((2-phenyl-sulphonyl-ethyl-N-methylamino)methyl)-thiazol-4-yl)-7-fluoro-quinazolin-4-yl)-amine;
(4-(3-Fluorobenzyloxy)-3-chlorophenyl)-(6-(2-((2-phenyl-sulphonyl-ethyl-N-methylamino)-ethyl)-thiazol-4-yl)-7-fluoro-quinazolin-4-yl)-amine;
(4-(3-Fluorobenzyloxy)-3-bromophenyl)-(6-(2-((2-phenyl-sulphonyl-ethyl-N-methylamino)ethyl)-thiazol-4-yl)-7-fluoro-quinazolin-4-yl)-amine;
(4-(3-Fluorobenzyloxy)-3-chlorophenyl)-(6-(2-((2-phenyl-sulphonyl-ethyl-N-methylamino)-propyl)-thiazol-4-yl)-7-fluoro-quinazolin-4-yl)-amine;
(4-(3-Fluorobenzyloxy)-3-bromophenyl)-(6-(2-((2-phenyl-sulphonyl-ethyl-N-methylamino)propyl)-thiazol-4-yl)-7-fluoro-quinazolin-4-yl)-amine;

List 47
(4-(3-Fluorobenzyloxy)-3-chlorophenyl)-(6-(2-((2-(2-pyridyl)-sulphonyl-ethyl-N-methylamino)-methyl)-furan-2-yl)-7-fluoro-quinazolin-4-yl)-amine;
(4-(3-Fluorobenzyloxy)-3-bromophenyl)-(6-(2-((2-(2-pyridyl)-sulphonyl-ethyl-N-methylamino)-methyl)-furan-2-yl)-7-fluoro-quinazolin-4-yl)-amine;
(4-(3-Fluorobenzyloxy)-3-chlorophenyl)-(6-(2-((2-(2-pyridyl)-sulphonyl-ethyl-N-methylamino)-ethyl)-furan-2-yl)-7-fluoro-quinazolin-4-yl)-amine;

(4-(3-Fluorobenzyloxy)-3-bromophenyl)-(6-(2-((2-(2-py-
ridyl)-sulphonyl-ethyl-N-methylamino)-ethyl)-furan-2-
yl)-7-fluoro-quinazolin-4-yl)-amine;
(4-(3-Fluorobenzyloxy)-3-chlorophenyl)-(6-(2-((2-(2-py-
ridyl)-sulphonyl-ethyl-N-methylamino)-propyl)-furan-2-
yl)-7-fluoro-quinazolin-4-yl)-amine;
(4-(3-Fluorobenzyloxy)-3-bromophenyl)-(6-(2-((2-(2-py-
ridyl)-sulphonyl-ethyl-N-methylamino)-propyl)-furan-2-
yl)-7-fluoro-quinazolin-4-yl)-amine;

List 48
(4-(3-Fluorobenzyloxy)-3-chlorophenyl)-(6-(2-((2-(2-py-
ridyl)-sulphonyl-ethyl-N-methylamino)-methyl)-thiazol
-4-yl)-7-fluoro-quinazolin-4-yl)-amine;
(4-(3-Fluorobenzyloxy)-3-bromophenyl)-(6-(2-((2-(2-py-
ridyl)-sulphonyl-ethyl-N-methylamino)methyl)-thiazol-
4-yl)-7-fluoro-quinazolin-4-yl)-amine;
(4-(3-Fluorobenzyloxy)-3-chlorophenyl)-(6-(2-((2-(2-py-
ridyl)-sulphonyl-ethyl-N-methylamino)-ethyl)-thiazol-4-
yl)-7-fluoro-quinazolin-4-yl)-amine;
(4-(3-Fluorobenzyloxy)-3-bromophenyl)-(6-(2-((2-(2-py-
ridyl)-sulphonyl-ethyl-N-methylamino)ethyl)-thiazol-4-
yl)-7-fluoro-quinazolin-4-yl)-amine;
(4-(3-Fluorobenzyloxy)-3-chlorophenyl)-(6-(2-((2-(2-py-
ridyl)-sulphonyl-ethyl-N-methylamino)-propyl)-thiazol-
4-yl)-7-fluoro-quinazolin-4-yl)-amine;
(4-(3-Fluorobenzyloxy)-3-bromophenyl)-(6-(2-((2-(2-py-
ridyl)-sulphonyl-ethyl-N-methylamino)propyl)-thiazol-4-
yl)-7-fluoro-quinazolin-4-yl)-amine;

List 49
(4-(3-Fluorobenzyloxy)-3-chlorophenyl)-(6-(2-((2-(2-N-
methylimidazolyl)-sulphonyl-ethylamino)-methyl)-fu-
ran-2-yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethylamino)-methyl)-fu-
ran-2-yl)-pyrido[3,4-d]pyrimidin-4-yl)-amine;
(4-(3-Fluorobenzyloxy)-3-chlorophenyl)-(6-(2-((2-(2-N-
methylimidazolyl)-sulphonyl-ethylamino)-ethyl)-furan-
2-yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethylamino)-ethyl)-furan-
2-yl)-pyrido[3,4-d]pyrimidin-4-yl)-amine;
(4-(3-Fluorobenzyloxy)-3-chlorophenyl)-(6-(2-((2-(2-N-
methylimidazolyl)-sulphonyl-ethylamino)-propyl)-furan-
2-yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethylamino)-propyl)-furan-
2-yl)-pyrido[3,4-d]pyrimidin-4-yl)-amine;

List 50
(4-(3-Fluorobenzyloxy)-3-chlorophenyl)-(6-(2-((2-(2-N-
methylimidazolyl)-sulphonyl-ethylamino)methyl)-thia-
zol-4-yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethylamino)methyl)-thia-
zol-4-yl)-pyrido[3,4-d]pyrimidin-4-yl)-amine;
(4-(3-Fluorobenzyloxy)-3-chlorophenyl)-(6-(2-((2-(2-N-
methylimidazolyl)-sulphonyl-ethylamino)ethyl)-thiazol-
4-yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethylamino)ethyl)-thiazol-
4-yl)-pyrido[3,4-d]pyrimidin-4-yl)-amine;
(4-(3-Fluorobenzyloxy)-3-chlorophenyl)-(6-(2-((2-(2-N-
methylimidazolyl)-sulphonyl-ethylamino)propyl)-thia-
zol-4-yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethylamino)propyl)-thia-
zol-4-yl)-pyrido[3,4-d]pyrimidin-4-yl)-amine;

List 51
(4-(3-Fluorobenzyloxy)-3-chlorophenyl)-(6-(2-((2-(2-N-
methylimidazolyl)-sulphonyl-ethylamino)-methyl)-fu-
ran-2-yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethoxy)-methyl)-furan-2-
yl)-pyrido[3,4-d]pyrimidin-4-yl)-amine;
(4-(3-Fluorobenzyloxy)-3-chlorophenyl)-(6-(2-((2-(2-N-
methylimidazolyl)-sulphonyl-ethylamino)-ethyl)-furan-
2-yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethoxy)-ethyl)-furan-2-yl)-
pyrido[3,4-d]pyrimidin-4-yl)-amine;
(4-(3-Fluorobenzyloxy)-3-chlorophenyl)-(6-(2-((2-(2-N-
methylimidazolyl)-sulphonyl-ethylamino)-propyl)-furan-
2-yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethoxy)-propyl)-furan-2-
yl)-pyrido[3,4-d]pyrimidin-4-yl)-amine;

List 52
(4-(3-Fluorobenzyloxy)-3-chlorophenyl)-(6-(2-((2-(2-N-
methylimidazolyl)-sulphonyl-ethoxy)methyl)-thiazol
-4-yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethoxy)methyl)-thiazol
-4-yl)-pyrido[3,4-d]pyrimidin-4-yl)-amine;
(4-(3-Fluorobenzyloxy)-3-chlorophenyl)-(6-(2-((2-(2-N-
methylimidazolyl)-sulphonyl-ethoxy)ethyl)-thiazol-4-
yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethoxy)ethyl)-thiazol-4-
yl)-pyrido[3,4-d]pyrimidin-4-yl)-amine;
(4-(3-Fluorobenzyloxy)-3-chlorophenyl)-(6-(2-((2-(2-N-
methylimidazolyl)-sulphonyl-ethoxy)propyl)-thiazol-4-
yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethoxy)propyl)-thiazol-4-
yl)-pyrido[3,4-d]pyrimidin-4-yl)-amine;

List 53
(4-(3-Fluorobenzyloxy)-3-chlorophenyl)-(6-(2-((2-(2-N-
methylimidazolyl)-sulphonyl-ethyl-N-methylamino)-me-
thyl)-furan-2-yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethyl-N-methylamino)-me-
thyl)-furan-2-yl)-pyrido[3,4-d]pyrimidin-4-yl)-amine;
(4-(3-Fluorobenzyloxy)-3-chlorophenyl)-(6-(2-((2-(2-N-
methylimidazolyl)-sulphonyl-ethyl-N-methylamino)-
ethyl)-furan-2-yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethyl-N-methylamino)-
ethyl)-furan-2-yl)-pyrido[3,4-d]pyrimidin-4-yl)-amine;
(4-(3-Fluorobenzyloxy)-3-chlorophenyl)-(6-(2-((2-(2-N-
methylimidazolyl)-sulphonyl-ethyl-N-methylamino)-pro-
pyl)-furan-2-yl)-pyrido[3,4-d]pyrimidin-4-yl)-amine;
(4-(3-Fluorobenzyloxy)-3-bromophenyl)-(6-(2-((2-(2-N-
methylimidazolyl)-sulphonyl-ethyl-N-methylamino)-pro-
pyl)-furan-2-yl)-pyrido[3,4-d]pyrimidin-4-yl)-amine;

List 54
(4-(3-Fluorobenzyloxy)-3-chlorophenyl)-(6-(2-((2-(2-N-
methylimidazolyl)-sulphonyl-ethyl-N-methylamino)-me-
thyl)-thiazol-4-yl)-pyrido[3,4-d]pyrimidin-4-yl)-amine;

(4-(3-Fluorobenzyloxy)-3-bromophenyl)-(6-(2-((2-(2-N-methylimidazolyl)-sulphonyl-ethyl-N-methylamino)methyl)-thiazol-4-yl)-pyrido[3,4-d]pyrimidin-4-yl)-amine;
(4-(3-Fluorobenzyloxy)-3-chlorophenyl)-(6-(2-((2-(2-N-methylimidazolyl)-sulphonyl-ethyl-N-methylamino)-ethyl)-thiazol-4-yl)-pyrido[3,4-d]pyrimidin-4-yl)-amine;
(4-(3-Fluorobenzyloxy)-3-bromophenyl)-(6-(2-((2-(2-N-methylimidazolyl)-sulphonyl-ethyl-N-methylamino)ethyl)-thiazol-4-yl)-pyrido[3,4-d]pyrimidin-4-yl)-amine;
(4-(3-Fluorobenzyloxy)-3-chlorophenyl)-(6-(2-((2-(2-N-methylimidazolyl)-sulphonyl-ethyl-N-methylamino)-propyl)-thiazol-4-yl)-pyrido[3,4-d]pyrimidin-4-yl)-amine;
(4-(3-Fluorobenzyloxy)-3-bromophenyl)-(6-(2-((2-(2-N-methylimidazolyl)-sulphonyl-ethyl-N-methylamino)propyl)-thiazol-4-yl)-pyrido[3,4-d]pyrimidin-4-yl)-amine;

List 55
(4-(3-Fluorobenzyloxy)-3-chlorophenyl)-(6-(2-((2-(2-N-methylimidazolyl)-sulphonyl-ethylamino)-ethyl)-furan-2-yl)-quinazolin-4-yl)-amine;
(4-(3-Fluorobenzyloxy)-3-bromophenyl)-(6-(2-((2-(2-N-methylimidazolyl)-sulphonyl-ethylamino)-ethyl)-furan-2-yl)-quinazolin-4-yl)-amine;
(4-(3-Fluorobenzyloxy)-3-bromophenyl)-(6-(2-((2-(2-N-methylimidazolyl)-sulphonyl-ethylamino)-propyl)-furan-2-yl)-quinazolin-4-yl)-amine;

List 56
(4-(3-Fluorobenzyloxy)-3-chlorophenyl)-(6-(2-((2-(2-N-methylimidazolyl)-sulphonyl-ethylamino)methyl)-thiazol-4-yl)-quinazolin-4-yl)-amine;
(4-(3-Fluorobenzyloxy)-3-bromophenyl)-(6-(2-((2-(2-N-methylimidazolyl)-sulphonyl-ethylamino)methyl)-thiazol-4-yl)-quinazolin-4-yl)-amine;
(4-(3-Fluorobenzyloxy)-3-chlorophenyl)-(6-(2-((2-(2-N-methylimidazolyl)-sulphonyl-ethylamino)ethyl)-thiazol-4-yl)-quinazolin-4-yl)-amine;
(4-(3-Fluorobenzyloxy)-3-bromophenyl)-(6-(2-((2-(2-N-methylimidazolyl)-sulphonyl-ethylamino)ethyl)-thiazol-4-yl)-quinazolin-4-yl)-amine;
(4-(3-Fluorobenzyloxy)-3-chlorophenyl)-(6-(2-((2-(2-N-methylimidazolyl)-sulphonyl-ethylamino)propyl)-thiazol-4-yl)-quinazolin-4-yl)-amine;
(4-(3-Fluorobenzyloxy)-3-bromophenyl)-(6-(2-((2-(2-N-methylimidazolyl)-sulphonyl-ethylamino)propyl)-thiazol-4-yl)-quinazolin-4-yl)-amine;

List 57
(4-(3-Fluorobenzyloxy)-3-chlorophenyl)-(6-(2-((2-(2-N-methylimidazolyl)-sulphonyl-ethylamino)-methyl)-furan-2-yl)-quinazolin-4-yl)-amine;
(4-(3-Fluorobenzyloxy)-3-bromophenyl)-(6-(2-((2-(2-N-methylimidazolyl)-sulphonyl-ethoxy)-methyl)-furan-2-yl)-quinazolin-4-yl)-amine;
(4-(3-Fluorobenzyloxy)-3-chlorophenyl)-(6-(2-((2-(2-N-methylimidazolyl)-sulphonyl-ethylamino)-ethyl)-furan-2-yl)-quinazolin-4-yl)-amine;
(4-(3-Fluorobenzyloxy)-3-bromophenyl)-(6-(2-((2-(2-N-methylimidazolyl)-sulphonyl-ethoxy)-ethyl)-furan-2-yl)-quinazolin-4-yl)-amine;
(4-(3-Fluorobenzyloxy)-3-bromophenyl)-(6-(2-((2-(2-N-methylimidazolyl)-sulphonyl-ethoxy)-propyl)-furan-2-yl)-quinazolin-4-yl)-amine;

List 58
(4-(3-Fluorobenzyloxy)-3-chlorophenyl)-(6-(2-((2-(2-N-methylimidazolyl)-sulphonyl-ethoxy)methyl)-thiazol-4-yl)-quinazolin-4-yl)-amine;
(4-(3-Fluorobenzyloxy)-3-bromophenyl)-(6-(2-((2-(2-N-methylimidazolyl)-sulphonyl-ethoxy)methyl)-thiazol-4-yl)-quinazolin-4-yl)-amine;
(4-(3-Fluorobenzyloxy)-3-chlorophenyl)-(6-(2-((2-(2-N-methylimidazolyl)-sulphonyl-ethoxy)ethyl)-thiazol-4-yl)-quinazolin-4-yl)-amine;
(4-(3-Fluorobenzyloxy)-3-bromophenyl)-(6-(2-((2-(2-N-methylimidazolyl)-sulphonyl-ethoxy)ethyl)-thiazol-4-yl)-quinazolin-4-yl)-amine;
(4-(3-Fluorobenzyloxy)-3-chlorophenyl)-(6-(2-((2-(2-N-methylimidazolyl)-sulphonyl-ethoxy)propyl)-thiazol-4-yl)-quinazolin-4-yl)-amine;
(4-(3-Fluorobenzyloxy)-3-bromophenyl)-(6-(2-((2-(2-N-methylimidazolyl)-sulphonyl-ethoxy)propyl)-thiazol-4-yl)-quinazolin-4-yl)-amine;

List 59
(4-(3-Fluorobenzyloxy)-3-chlorophenyl)-(6-(2-((2-(2-N-methylimidazolyl)-sulphonyl-ethyl-N-methylamino)-methyl)-furan-2-yl)-quinazolin-4-yl)-amine;
(4-(3-Fluorobenzyloxy)-3-bromophenyl)-(6-(2-((2-(2-N-methylimidazolyl)-sulphonyl-ethyl-N-methylamino)-methyl)-furan-2-yl)-quinazolin-4-yl)-amine;
(4-(3-Fluorobenzyloxy)-3-chlorophenyl)-(6-(2-((2-(2-N-methylimidazolyl)-sulphonyl-ethyl-N-methylamino)-ethyl)-furan-2-yl)-quinazolin-4-yl)-amine;
(4-(3-Fluorobenzyloxy)-3-bromophenyl)-(6-(2-((2-(2-N-methylimidazolyl)-sulphonyl-ethyl-N-methylamino)-ethyl)-furan-2-yl)-quinazolin-4-yl)-amine;
(4-(3-Fluorobenzyloxy)-3-chlorophenyl)-(6-(2-((2-(2-N-methylimidazolyl)-sulphonyl-ethyl-N-methylamino)-propyl)-furan-2-yl)-quinazolin-4-yl)-amine;
(4-(3-Fluorobenzyloxy)-3-bromophenyl)-(6-(2-((2-(2-N-methylimidazolyl)-sulphonyl-ethyl-N-methylamino)-propyl)-furan-2-yl)-quinazolin-4-yl)-amine;

List 60
(4-(3-Fluorobenzyloxy)-3-chlorophenyl)-(6-(2-((2-(2-N-methylimidazolyl)-sulphonyl-ethyl-N-methylamino)-methyl)-thiazol -4-yl)-quinazolin-4-yl)-amine;
(4-(3-Fluorobenzyloxy)-3-bromophenyl)-(6-(2-((2-(2-N-methylimidazolyl)-sulphonyl-ethyl-N-methylamino)methyl)-thiazol-4-yl)-quinazolin-4-yl)-amine;
(4-(3-Fluorobenzyloxy)-3-chlorophenyl)-(6-(2-((2-(2-N-methylimidazolyl)-sulphonyl-ethyl-N-methylamino)-ethyl)-thiazol-4-yl)-quinazolin-4-yl)-amine;
(4-(3-Fluorobenzyloxy)-3-bromophenyl)-(6-(2-((2-(2-N-methylimidazolyl)-sulphonyl-ethyl-N-methylamino)ethyl)-thiazol-4-yl)-quinazolin-4-yl)-amine;
(4-(3-Fluorobenzyloxy)-3-chlorophenyl)-(6-(2-((2-(2-N-methylimidazolyl)-sulphonyl-ethyl-N-methylamino)-propyl)-thiazol-4-yl)-quinazolin-4-yl)-amine;
(4-(3-Fluorobenzyloxy)-3-bromophenyl)-(6-(2-((2-(2-N-methylimidazolyl)-sulphonyl-ethyl-N-methylamino)propyl)-thiazol-4-yl)-quinazolin-4-yl)-amine;

List 61
(4-(3-Fluorobenzyloxy)-3-chlorophenyl)-(6-(2-((2-(2-N-methylimidazolyl)-sulphonyl-ethylamino)-methyl)-furan-2-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethylamino)-methyl)-furan-2-yl)-7-methoxy-quinazolin-4-yl)-amine;
(4-(3-Fluorobenzyloxy)-3-chlorophenyl)-(6-(2-((2-(2-N-methylimidazolyl)-sulphonyl-ethylamino)-ethyl)-furan-2-yl)-7-methoxy-quinazolin-4-yl)-amine;

(4-(3-Fluorobenzyloxy)-3-bromophenyl)-(6-(2-((2-(2-N-methylimidazolyl)-sulphonyl-ethylamino)-ethyl)-furan-2-yl)-7-methoxy-quinazolin-4-yl)-amine;
(4-(3-Fluorobenzyloxy)-3-chlorophenyl)-(6-(2-((2-(2-N-methylimidazolyl)-sulphonyl-ethylamino)-propyl)-furan-2-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethylamino)-propyl)-furan-2-yl)-7-methoxy-quinazolin-4-yl)-amine;

List 62
(4-(3-Fluorobenzyloxy)-3-chlorophenyl)-(6-(2-((2-(2-N-methylimidazolyl)-sulphonyl-ethylamino)methyl)-thiazol-4-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethylamino)methyl)-thiazol-4-yl)-7-methoxy-quinazolin-4-yl)-amine;
(4-(3-Fluorobenzyloxy)-3-chlorophenyl)-(6-(2-((2-(2-N-methylimidazolyl)-sulphonyl-ethylamino)ethyl)-thiazol-4-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethylamino)ethyl)-thiazol-4-yl)-7-methoxy-quinazolin-4-yl)-amine;
(4-(3-Fluorobenzyloxy)-3-chlorophenyl)-(6-(2-((2-(2-N-methylimidazolyl)-sulphonyl-ethylamino)propyl)-thiazol-4-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethylamino)propyl)-thiazol-4-yl)-7-methoxy-quinazolin-4-yl)-amine;

List 63
(4-(3-Fluorobenzyloxy)-3-chlorophenyl)-(6-(2-((2-(2-N-methylimidazolyl)-sulphonyl-ethylamino)-methyl)-furan-2-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethoxy)-methyl)-furan-2-yl)-7-methoxy-quinazolin-4-yl)-amine;
(4-(3-Fluorobenzyloxy)-3-chlorophenyl)-(6-(2-((2-(2-N-methylimidazolyl)-sulphonyl-ethylamino)-ethyl)-furan-2-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethoxy)-ethyl)-furan-2-yl)-7-methoxy-quinazolin-4-yl)-amine;
(4-(3-Fluorobenzyloxy)-3-chlorophenyl)-(6-(2-((2-(2-N-methylimidazolyl)-sulphonyl-ethylamino)-propyl)-furan-2-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethoxy)-propyl)-furan-2-yl)-7-methoxy-quinazolin-4-yl)-amine;

List 64
(4-(3-Fluorobenzyloxy)-3-chlorophenyl)-(6-(2-((2-(2-N-methylimidazolyl)-sulphonyl-ethoxy)methyl)-thiazol-4-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethoxy)methyl)-thiazol-4-yl)-7-methoxy-quinazolin-4-yl)-amine;
(4-(3-Fluorobenzyloxy)-3-chlorophenyl)-(6-(2-((2-(2-N-methylimidazolyl)-sulphonyl-ethoxy)ethyl)-thiazol-4-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethoxy)ethyl)-thiazol-4-yl)-7-methoxy-quinazolin-4-yl)-amine;
(4-(3-Fluorobenzyloxy)-3-chlorophenyl)-(6-(2-((2-(2-N-methylimidazolyl)-sulphonyl-ethoxy)propyl)-thiazol-4-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethoxy)propyl)-thiazol-4-yl)-7-methoxy-quinazolin-4-yl)-amine;

List 65
(4-(3-Fluorobenzyloxy)-3-chlorophenyl)-(6-(2-((2-(2-N-methylimidazolyl)-sulphonyl-ethyl-N-methylamino)-methyl)-furan-2-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethyl-N-methylamino)-methyl)-furan-2-yl)-7-methoxy-quinazolin-4-yl)-amine;
(4-(3-Fluorobenzyloxy)-3-chlorophenyl)-(6-(2-((2-(2-N-methylimidazolyl)-sulphonyl-ethyl-N-methylamino)-ethyl)-furan-2-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethyl-N-methylamino)-ethyl)-furan-2-yl)-7-methoxy-quinazolin-4-yl)-amine;
(4-(3-Fluorobenzyloxy)-3-chlorophenyl)-(6-(2-((2-(2-N-methylimidazolyl)-sulphonyl-ethyl-N-methylamino)-propyl)-furan-2-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethyl-N-methylamino)-propyl)-furan-2-yl)-7-methoxy-quinazolin-4-yl)-amine;

List 66
(4-(3-Fluorobenzyloxy)-3-chlorophenyl)-(6-(2-((2-(2-N-methylimidazolyl)-sulphonyl-ethyl-N-methylamino)-methyl)-thiazol-4-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethyl-N-methylamino)methyl)-thiazol-4-yl)-7-methoxy-quinazolin-4-yl)-amine;
(4-(3-Fluorobenzyloxy)-3-chlorophenyl)-(6-(2-((2-(2-N-methylimidazolyl)-sulphonyl-ethyl-N-methylamino)-ethyl)-thiazol-4-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethyl-N-methylamino) ethyl)-thiazol-4-yl)-7-methoxy-quinazolin-4-yl)-amine;
(4-(3-Fluorobenzyloxy)-3-chlorophenyl)-(6-(2-((2-(2-N-methylimidazolyl)-sulphonyl-ethyl-N-methylamino)-propyl)-thiazol-4-yl)-7-methoxy-quinazolin-4-yl)-amine;
(4-(3-Fluorobenzyloxy)-3-bromophenyl)-(6-(2-((2-(2-N-methylimidazolyl)-sulphonyl-ethyl-N-methylamino)propyl)-thiazol-4-yl)-7-methoxy-quinazolin-4-yl)-amine;

List 67
(4-(3-Fluorobenzyloxy)-3-chlorophenyl)-(6-(2-((2-(2-N-methylimidazolyl)-sulphonyl-ethylamino)-methyl)-furan-2-yl)-7-fluoro-quinazolin-4-yl)-amine;
(4-(3-Fluorobenzyloxy)-3-bromophenyl)-(6-(2-((2-(2-N-methylimidazolyl)-sulphonyl-ethylamino)-methyl)-furan-2-yl)-7-fluoro-quinazolin-4-yl)-amine;
(4-(3-Fluorobenzyloxy)-3-chlorophenyl)-(6-(2-((2-(2-N-methylimidazolyl)-sulphonyl-ethylamino)-ethyl)-furan-2-yl)-7-fluoro-quinazolin-4-yl)-amine;
(4-(3-Fluorobenzyloxy)-3-bromophenyl)-(6-(2-((2-(2-N-methylimidazolyl)-sulphonyl-ethylamino)-ethyl)-furan-2-yl)-7-fluoro-quinazolin-4-yl)-amine;
(4-(3-Fluorobenzyloxy)-3-chlorophenyl)-(6-(2-((2-(2-N-methylimidazolyl)-sulphonyl-ethylamino)-propyl)-furan-2-yl)-7-fluoro-quinazolin-4-yl)-amine;
(4-(3-Fluorobenzyloxy)-3-bromophenyl)-(6-(2-((2-(2-N-methylimidazolyl)-sulphonyl-ethylamino)-propyl)-furan-2-yl)-7-fluoro-quinazolin-4-yl)-amine;

List 68
(4-(3-Fluorobenzyloxy)-3-chlorophenyl)-(6-(2-((2-(2-N-methylimidazolyl)-sulphonyl-ethylamino)methyl)-thiazol-4-yl)-7-fluoro-quinazolin-4-yl)-amine;

(4-(3-Fluorobenzyloxy)-3-bromophenyl)-(6-(2-((2-(2-N-methylimidazolyl)-sulphonyl-ethylamino)methyl)-thiazol-4-yl)-7-fluoro-quinazolin-4-yl)-amine;

(4-(3-Fluorobenzyloxy)-3-chlorophenyl)-(6-(2-((2-(2-N-methylimidazolyl)-sulphonyl-ethylamino)ethyl)-thiazol-4-yl)-7-fluoro-quinazolin-4-yl)-amine;

(4-(3-Fluorobenzyloxy)-3-bromophenyl)-(6-(2-((2-(2-N-methylimidazolyl)-sulphonyl-ethylamino)ethyl)-thiazol-4-yl)-7-fluoro-quinazolin-4-yl)-amine;

(4-(3-Fluorobenzyloxy)-3-chlorophenyl)-(6-(2-((2-(2-N-methylimidazolyl)-sulphonyl-ethylamino)propyl)-thiazol-4-yl)-7-fluoro-quinazolin-4-yl)-amine;

(4-(3-Fluorobenzyloxy)-3-bromophenyl)-(6-(2-((2-(2-N-methylimidazolyl)-sulphonyl-ethylamino)propyl)-thiazol-4-yl)-7-fluoro-quinazolin-4-yl)-amine;

List 69

(4-(3-Fluorobenzyloxy)-3-chlorophenyl)-(6-(2-((2-(2-N-methylimidazolyl)-sulphonyl-ethylamino)-methyl)-furan-2-yl)-7-fluoro-quinazolin-4-yl)-amine;

(4-(3-Fluorobenzyloxy)-3-bromophenyl)-(6-(2-((2-(2-N-methylimidazolyl)-sulphonyl-ethoxy)-methyl)-furan-2-yl)-7-fluoro-quinazolin-4-yl)-amine;

(4-(3-Fluorobenzyloxy)-3-chlorophenyl)-(6-(2-((2-(2-N-methylimidazolyl)-sulphonyl-ethylamino)-ethyl)-furan-2-yl)-7-fluoro-quinazolin-4-yl)-amine;

(4-(3-Fluorobenzyloxy)-3-bromophenyl)-(6-(2-((2-(2-N-methylimidazolyl)-sulphonyl-ethoxy)-ethyl)-furan-2-yl)-7-fluoro-quinazolin-4-yl)-amine;

(4-(3-Fluorobenzyloxy)-3-chlorophenyl)-(6-(2-((2-(2-N-methylimidazolyl)-sulphonyl-ethylamino)-propyl)-furan-2-yl)-7-fluoro-quinazolin-4-yl)-amine;

(4-(3-Fluorobenzyloxy)-3-bromophenyl)-(6-(2-((2-(2-N-methylimidazolyl)-sulphonyl-ethoxy)-propyl)-furan-2-yl)-7-fluoro-quinazolin-4-yl)-amine;

List 70

(4-(3-Fluorobenzyloxy)-3-chlorophenyl)-(6-(2-((2-(2-N-methylimidazolyl)-sulphonyl-ethoxy)methyl)-thiazol-4-yl)-7-fluoro-quinazolin-4-yl)-amine;

(4-(3-Fluorobenzyloxy)-3-bromophenyl)-(6-(2-((2-phenyl-sulphonyl-ethoxy)methyl)-thiazol-4-yl)-7-fluoro-quinazolin-4-yl)-amine;

(4-(3-Fluorobenzyloxy)-3-chlorophenyl)-(6-(2-((2-(2-N-methylimidazolyl)-sulphonyl-ethoxy)ethyl)-thiazol-4-yl)-7-fluoro-quinazolin-4-yl)-amine;

(4-(3-Fluorobenzyloxy)-3-bromophenyl)-(6-(2-((2-(2-N-methylimidazolyl)-sulphonyl-ethoxy)ethyl)-thiazol-4-yl)-7-fluoro-quinazolin-4-yl)-amine;

(4-(3-Fluorobenzyloxy)-3-chlorophenyl)-(6-(2-((2-(2-N-methylimidazolyl)-sulphonyl-ethoxy)propyl)-thiazol-4-yl)-7-fluoro-quinazolin-4-yl)-amine;

(4-(3-Fluorobenzyloxy)-3-bromophenyl)-(6-(2-((2-(2-N-methylimidazolyl)-sulphonyl-ethoxy)propyl)-thiazol-4-yl)-7-fluoro-quinazolin-4-yl)-amine;

List 71

(4-(3-Fluorobenzyloxy)-3-chlorophenyl)-(6-(2-((2-(2-N-methylimidazolyl)-sulphonyl-ethyl-N-methylamino)-methyl)-furan-2-yl)-7-fluoro-quinazolin-4-yl)-amine;

(4-(3-Fluorobenzyloxy)-3-bromophenyl)-(6-(2-((2-(2-N-methylimidazolyl)-sulphonyl-ethyl-N-methylamino)-methyl)-furan-2-yl)-7-fluoro-quinazolin-4-yl)-amine;

(4-(3-Fluorobenzyloxy)-3-chlorophenyl)-(6-(2-((2-(2-N-methylimidazolyl)-sulphonyl-ethyl-N-methylamino)-ethyl)-furan-2-yl)-7-fluoro-quinazolin-4-yl)-amine;

(4-(3-Fluorobenzyloxy)-3-bromophenyl)-(6-(2-((2-(2-N-methylimidazolyl)-sulphonyl-ethyl-N-methylamino)-ethyl)-furan-2-yl)-7-fluoro-quinazolin-4-yl)-amine;

(4-(3-Fluorobenzyloxy)-3-chlorophenyl)-(6-(2-((2-(2-N-methylimidazolyl)-sulphonyl-ethyl-N-methylamino)-propyl)-furan-2-yl)-7-fluoro-quinazolin-4-yl)-amine;

(4-(3-Fluorobenzyloxy)-3-bromophenyl)-(6-(2-((2-(2-N-methylimidazolyl)-sulphonyl-ethyl-N-methylamino)-propyl)-furan-2-yl)-7-fluoro-quinazolin-4-yl)-amine;

List 72

(4-(3-Fluorobenzyloxy)-3-chlorophenyl)-(6-(2-((2-(2-N-methylimidazolyl)-sulphonyl-ethyl-N-methylamino)-methyl)-thiazol-4-yl)-7-fluoro-quinazolin-4-yl)-amine;

(4-(3-Fluorobenzyloxy)-3-bromophenyl)-(6-(2-((2-(2-N-methylimidazolyl)-sulphonyl-ethyl-N-methylamino)methyl)-thiazol-4-yl)-7-fluoro-quinazolin-4-yl)-amine;

(4-(3-Fluorobenzyloxy)-3-chlorophenyl)-(6-(2-((2-(2-N-methylimidazolyl)-sulphonyl-ethyl-N-methylamino)-ethyl)-thiazol-4-yl)-7-fluoro-quinazolin-4-yl)-amine;

(4-(3-Fluorobenzyloxy)-3-bromophenyl)-(6-(2-((2-(2-N-methylimidazolyl)-sulphonyl-ethyl-N-methylamino)ethyl)-thiazol-4-yl)-7-fluoro-quinazolin-4-yl)-amine;

(4-(3-Fluorobenzyloxy)-3-chlorophenyl)-(6-(2-((2-(2-N-methylimidazolyl)-sulphonyl-ethyl-N-methylamino)-propyl)-thiazol-4-yl)-7-fluoro-quinazolin-4-yl)-amine;

(4-(3-Fluorobenzyloxy)-3-bromophenyl)-(6-(2-((2-(2-N-methylimidazolyl)-sulphonyl-ethyl-N-methylamino)propyl)-thiazol-4-yl)-7-fluoro-quinazolin-4-yl)-amine;

List 73

(4-(3-Fluorobenzyloxy)-3-chlorophenyl)-(6-(2-((2-methanesulphonyl-ethylamino)-ethyl)-furan-2-yl)-pyrido[3,4-d]pyrimidin-4-yl)-amine;

(4-(3-Fluorobenzyloxy)-3-bromophenyl)-(6-(2-((2-methanesulphonyl-ethylamino)-ethyl)-furan-2-yl)-pyrido[3,4-d]pyrimidin-4-yl)-amine;

(4-(3-Fluorobenzyloxy)-3-chlorophenyl)-(6-(2-((2-methanesulphonyl-ethylamino)-propyl)-furan-2-yl)-pyrido[3,4-d]pyrimidin-4-yl)-amine;

(4-(3-Fluorobenzyloxy)-3-bromophenyl)-(6-(2-((2-methanesulphonyl-ethylamino)-propyl)-furan-2-yl)-pyrido[3,4-d]pyrimidin-4-yl)-amine;

List 74

(4-(3-Fluorobenzyloxy)-3-chlorophenyl)-(6-(2-((2-methanesulphonyl-ethylamino)ethyl)-thiazol-4-yl)-pyrido[3,4-d]pyrimidin-4-yl)-amine;

(4-(3-Fluorobenzyloxy)-3-bromophenyl)-(6-(2-((2-methanesulphonyl-ethylamino)ethyl)-thiazol-4-yl)-pyrido[3,4-d]pyrimidin-4-yl)-amine;

(4-(3-Fluorobenzyloxy)-3-chlorophenyl)-(6-(2-((2-methanesulphonyl-ethylamino)propyl)-thiazol-4-yl)-pyrido[3,4-d]pyrimidin-4-yl)-amine;

(4-(3-Fluorobenzyloxy)-3-bromophenyl)-(6-(2-((2-methanesulphonyl-ethylamino)propyl)-thiazol-4-yl)-pyrido[3,4-d]pyrimidin-4-yl)-amine;

List 75

(4-(3-Fluorobenzyloxy)-3-chlorophenyl)-(6-(2-((2-ethanesulphonyl-ethylamino)-methyl)-furan-2-yl)-pyrido[3,4-d]pyrimidin-4-yl)-amine;

(4-(3-Fluorobenzyloxy)-3-bromophenyl)-(6-(2-((2-ethanesulphonyl-ethylamino)-methyl)-furan-2-yl)-pyrido[3,4-d]pyrimidin-4-yl)-amine;

(4-(3-Fluorobenzyloxy)-3-chlorophenyl)-(6-(2-((2-ethanesulphonyl-ethylamino)-ethyl)-furan-2-yl)-pyrido[3,4-d]pyrimidin-4-yl)-amine;

(4-(3-Fluorobenzyloxy)-3-bromophenyl)-(6-(2-((2-ethane-sulphonyl-ethylamino)-ethyl)-furan-2-yl)-pyrido[3,4-d]pyrimidin-4-yl)-amine;
(4-(3-Fluorobenzyloxy)-3-chlorophenyl)-(6-(2-((2-ethane-sulphonyl-ethylamino)-propyl)-furan-2-yl)-pyrido[3,4-d]pyrimidin-4-yl)-amine;
(4-(3-Fluorobenzyloxy)-3-bromophenyl)-(6-(2-((2-ethane-sulphonyl-ethylamino)-propyl)-furan-2-yl)-pyrido[3,4-d]pyrimidin-4-yl)-amine;

List 76
(4-(3-Fluorobenzyloxy)-3-chlorophenyl)-(6-(2-((2-ethane-sulphonyl-ethylamino)methyl)-thiazol-4-yl)-pyrido[3,4-d]pyrimidin-4-yl)-amine;
(4-(3-Fluorobenzyloxy)-3-bromophenyl)-(6-(2-((2-ethane-sulphonyl-ethylamino)methyl)-thiazol-4-yl)-pyrido[3,4-d]pyrimidin-4-yl)-amine;
(4-(3-Fluorobenzyloxy)-3-chlorophenyl)-(6-(2-((2-ethane-sulphonyl-ethylamino)ethyl)-thiazol-4-yl)-pyrido[3,4-d]pyrimidin-4-yl)-amine;
(4-(3-Fluorobenzyloxy)-3-bromophenyl)-(6-(2-((2-ethane-sulphonyl-ethylamino)ethyl)-thiazol-4-yl)-pyrido[3,4-d]pyrimidin-4-yl)-amine;
(4-(3-Fluorobenzyloxy)-3-chlorophenyl)-(6-(2-((2-ethane-sulphonyl-ethylamino)propyl)-thiazol-4-yl)-pyrido[3,4-d]pyrimidin-4-yl)-amine;
(4-(3-Fluorobenzyloxy)-3-bromophenyl)-(6-(2-((2-ethane-sulphonyl-ethylamino)propyl)-thiazol-4-yl)-pyrido[3,4-d]pyrimidin-4-yl)-amine;

List 77
(4-(3-Fluorobenzyloxy)-3-chlorophenyl)-(6-(2-((2-propane-sulphonyl-ethylamino)-methyl)-furan-2-yl)-pyrido[3,4-d]pyrimidin-4-yl)-amine;
(4-(3-Fluorobenzyloxy)-3-bromophenyl)-(6-(2-((2-propanesulphonyl-ethylamino)-methyl)-furan-2-yl)-pyrido[3,4-d]pyrimidin-4-yl)-amine;
(4-(3-Fluorobenzyloxy)-3-chlorophenyl)-(6-(2-((2-propane-sulphonyl-ethylamino)-ethyl)-furan-2-yl)-pyrido[3,4-d]pyrimidin-4-yl)-amine;
(4-(3-Fluorobenzyloxy)-3-bromophenyl)-(6-(2-((2-propanesulphonyl-ethylamino)-ethyl)-furan-2-yl)-pyrido[3,4-d]pyrimidin-4-yl)-amine;
(4-(3-Fluorobenzyloxy)-3-chlorophenyl)-(6-(2-((2-propane-sulphonyl-ethylamino)-propyl)-furan-2-yl)-pyrido[3,4-d]pyrimidin-4-yl)-amine;
(4-(3-Fluorobenzyloxy)-3-bromophenyl)-(6-(2-((2-propanesulphonyl-ethylamino)-propyl)-furan-2-yl)-pyrido[3,4-d]pyrimidin-4-yl)-amine;

List 78
(4-(3-Fluorobenzyloxy)-3-chlorophenyl)-(6-(2-((2-iso-propyl-sulphonyl-ethylamino)-methyl)-furan-2-yl)-pyrido[3,4-d]pyrimidin-4-yl)-amine;
(4-(3-Fluorobenzyloxy)-3-bromophenyl)-(6-(2-((2-iso-propyl-sulphonyl-ethylamino)-methyl)-furan-2-yl)-pyrido[3,4-d]pyrimidin-4-yl)-amine;
(4-(3-Fluorobenzyloxy)-3-chlorophenyl)-(6-(2-((2-iso-propyl-sulphonyl-ethylamino)-ethyl)-furan-2-yl)-pyrido[3,4-d]pyrimidin-4-yl)-amine;
(4-(3-Fluorobenzyloxy)-3-bromophenyl)-(6-(2-((2-iso-propyl-sulphonyl-ethylamino)-ethyl)-furan-2-yl)-pyrido[3,4-d]pyrimidin-4-yl)-amine;
(4-(3-Fluorobenzyloxy)-3-chlorophenyl)-(6-(2-((2-iso-propyl-sulphonyl-ethylamino)-propyl)-furan-2-yl)-pyrido[3,4-d]pyrimidin-4-yl)-amine;
(4-(3-Fluorobenzyloxy)-3-bromophenyl)-(6-(2-((2-iso-propyl-sulphonyl-ethylamino)-propyl)-furan-2-yl)-pyrido[3,4-d]pyrimidin-4-yl)-amine;

List 79
(4-(3-Fluorobenzyloxy)-3-chlorophenyl)-(6-(2-((2-propane-sulphonyl-ethylamino)methyl)-thiazol-4-yl)-pyrido[3,4-d]pyrimidin-4-yl)-amine;
(4-(3-Fluorobenzyloxy)-3-bromophenyl)-(6-(2-((2-propanesulphonyl-ethylamino)methyl)-thiazol-4-yl)-pyrido[3,4-d]pyrimidin-4-yl)-amine;
(4-(3-Fluorobenzyloxy)-3-chlorophenyl)-(6-(2-((2-propane-sulphonyl-ethylamino)ethyl)-thiazol-4-yl)-pyrido[3,4-d]pyrimidin-4-yl)-amine;
(4-(3-Fluorobenzyloxy)-3-bromophenyl)-(6-(2-((2-propanesulphonyl-ethylamino)ethyl)-thiazol-4-yl)-pyrido[3,4-d]pyrimidin-4-yl)-amine;
(4-(3-Fluorobenzyloxy)-3-chlorophenyl)-(6-(2-((2-propane-sulphonyl-ethylamino)propyl)-thiazol-4-yl)-pyrido[3,4-d]pyrimidin-4-yl)-amine;
(4-(3-Fluorobenzyloxy)-3-bromophenyl)-(6-(2-((2-propanesulphonyl-ethylamino)propyl)-thiazol-4-yl)-pyrido[3,4-d]pyrimidin-4-yl)-amine;

List 80
(4-(3-Fluorobenzyloxy)-3-chlorophenyl)-(6-(2-((2-iso-propyl-sulphonyl-ethylamino)methyl)-thiazol-4-yl)-pyrido[3,4-d]pyrimidin-4-yl)-amine;
(4-(3-Fluorobenzyloxy)-3-bromophenyl)-(6-(2-((2-iso-propyl-sulphonyl-ethylamino)methyl)-thiazol-4-yl)-pyrido[3,4-d]pyrimidin-4-yl)-amine;
(4-(3-Fluorobenzyloxy)-3-chlorophenyl)-(6-(2-((2-iso-propyl-sulphonyl-ethylamino)ethyl)-thiazol-4-yl)-pyrido[3,4-d]pyrimidin-4-yl)-amine;
(4-(3-Fluorobenzyloxy)-3-bromophenyl)-(6-(2-((2-iso-propyl-sulphonyl-ethylamino)ethyl)-thiazol-4-yl)-pyrido[3,4-d]pyrimidin-4-yl)-amine;
(4-(3-Fluorobenzyloxy)-3-chlorophenyl)-(6-(2-((2-iso-propyl-sulphonyl-ethylamino)propyl)-thiazol-4-yl)-pyrido[3,4-d]pyrimidin-4-yl)-amine;
(4-(3-Fluorobenzyloxy)-3-bromophenyl)-(6-(2-((2-iso-propyl-sulphonyl-ethylamino)propyl)-thiazol-4-yl)-pyrido[3,4-d]pyrimidin-4-yl)-amine;

List 81
(4-(3-Fluorobenzyloxy)-3-chlorophenyl)-(6-(2-((2-methanesulphonyl-ethoxy)methyl)-furan-2-yl)-pyrido[3,4-d]pyrimidin-4-yl)-amine;
(4-(3-Fluorobenzyloxy)-3-bromophenyl)-(6-(2-((2-methanesulphonyl-ethoxy)methyl)-furan-2-yl)-pyrido[3,4-d]pyrimidin-4-yl)-amine;
(4-(3-Fluorobenzyloxy)-3-chlorophenyl)-(6-(2-((2-methanesulphonyl-ethoxy)ethyl)-furan-2-yl)-pyrido[3,4-d]pyrimidin-4-yl)-amine;
(4-(3-Fluorobenzyloxy)-3-bromophenyl)-(6-(2-((2-methanesulphonyl-ethoxy)ethyl)-furan-2-yl)-pyrido[3,4-d]pyrimidin-4-yl)-amine;
(4-(3-Fluorobenzyloxy)-3-chlorophenyl)-(6-(2-((2-methanesulphonyl-ethoxy)propyl)-furan-2-yl)-pyrido[3,4-d]pyrimidin-4-yl)-amine;
(4-(3-Fluorobenzyloxy)-3-bromophenyl)-(6-(2-((2-methanesulphonyl-ethoxy)propyl)-furan-2-yl)-pyrido[3,4-d]pyrimidin-4-yl)-amine;

List 82
(4-(3-Fluorobenzyloxy)-3-chlorophenyl)-(6-(2-((2-methanesulphonyl-ethoxy)methyl)-thiazol-4-yl)-pyrido[3,4-d]pyrimidin-4-yl)-amine;

(4-(3-Fluorobenzyloxy)-3-bromophenyl)-(6-(2-((2-methanesulphonyl-ethoxy)methyl)-thiazol-4-yl)-pyrido[3,4-d]pyrimidin-4-yl)-amine;
(4-(3-Fluorobenzyloxy)-3-chlorophenyl)-(6-(2-((2-methanesulphonyl-ethoxy)ethyl)-thiazol-4-yl)-pyrido[3,4-d]pyrimidin-4-yl)-amine;
(4-(3-Fluorobenzyloxy)-3-bromophenyl)-(6-(2-((2-methanesulphonyl-ethoxy)ethyl)-thiazol-4-yl)-pyrido[3,4-d]pyrimidin-4-yl)-amine;
(4-(3-Fluorobenzyloxy)-3-chlorophenyl)-(6-(2-((2-methanesulphonyl-ethoxy)propyl)-thiazol-4-yl)-pyrido[3,4-d]pyrimidin-4-yl)-amine;
(4-(3-Fluorobenzyloxy)-3-bromophenyl)-(6-(2-((2-methanesulphonyl-ethoxy)propyl)-thiazol-4-yl)-pyrido[3,4-d]pyrimidin-4-yl)-amine;

List 83
(4-(3-Fluorobenzyloxy)-3-chlorophenyl)-(6-(2-((2-ethanesulphonyl-ethoxy)-methyl)-furan-2-yl)-pyrido[3,4-d]pyrimidin-4-yl)-amine;
(4-(3-Fluorobenzyloxy)-3-bromophenyl)-(6-(2-((2-ethanesulphonyl-ethoxy)-methyl)-furan-2-yl)-pyrido[3,4-d]pyrimidin-4-yl)-amine;
(4-(3-Fluorobenzyloxy)-3-chlorophenyl)-(6-(2-((2-ethanesulphonyl-ethoxy)-ethyl)-furan-2-yl)-pyrido[3,4-d]pyrimidin-4-yl)-amine;
(4-(3-Fluorobenzyloxy)-3-bromophenyl)-(6-(2-((2-ethanesulphonyl-ethoxy)-ethyl)-furan-2-yl)-pyrido[3,4-d]pyrimidin-4-yl)-amine;
(4-(3-Fluorobenzyloxy)-3-chlorophenyl)-(6-(2-((2-ethanesulphonyl-ethoxy)-propyl)-furan-2-yl)-pyrido[3,4-d]pyrimidin-4-yl)-amine;
(4-(3-Fluorobenzyloxy)-3-bromophenyl)-(6-(2-((2-ethanesulphonyl-ethoxy)-propyl)-furan-2-yl)-pyrido[3,4-d]pyrimidin-4-yl)-amine;

List 84
(4-(3-Fluorobenzyloxy)-3-chlorophenyl)-(6-(2-((2-ethanesulphonyl-ethoxy)methyl)-thiazol-4-yl)-pyrido[3,4-d]pyrimidin-4-yl)-amine;
(4-(3-Fluorobenzyloxy)-3-bromophenyl)-(6-(2-((2-ethanesulphonyl-ethoxy)methyl)-thiazol-4-yl)-pyrido[3,4-d]pyrimidin-4-yl)-amine;
(4-(3-Fluorobenzyloxy)-3-chlorophenyl)-(6-(2-((2-ethanesulphonyl-ethoxy)ethyl)-thiazol-4-yl)-pyrido[3,4-d]pyrimidin-4-yl)-amine;
(4-(3-Fluorobenzyloxy)-3-bromophenyl)-(6-(2-((2-ethanesulphonyl-ethoxy)ethyl)-thiazol-4-yl)-pyrido[3,4-d]pyrimidin-4-yl)-amine;
(4-(3-Fluorobenzyloxy)-3-chlorophenyl)-(6-(2-((2-ethanesulphonyl-ethoxy)propyl)-thiazol-4-yl)-pyrido[3,4-d]pyrimidin-4-yl)-amine;
(4-(3-Fluorobenzyloxy)-3-bromophenyl)-(6-(2-((2-ethanesulphonyl-ethoxy)propyl)-thiazol-4-yl)-pyrido[3,4-d]pyrimidin-4-yl)-amine;

List 85
(4-(3-Fluorobenzyloxy)-3-chlorophenyl)-(6-(2-((2-propanesulphonyl-ethoxy)-methyl)-furan-2-yl)-pyrido[3,4-d]pyrimidin-4-yl)-amine;
(4-(3-Fluorobenzyloxy)-3-bromophenyl)-(6-(2-((2-propanesulphonyl-ethoxy)-methyl)-furan-2-yl)-pyrido[3,4-d]pyrimidin-4-yl)-amine;
(4-(3-Fluorobenzyloxy)-3-chlorophenyl)-(6-(2-((2-propanesulphonyl-ethoxy)-ethyl)-furan-2-yl)-pyrido[3,4-d]pyrimidin-4-yl)-amine;
(4-(3-Fluorobenzyloxy)-3-bromophenyl)-(6-(2-((2-propanesulphonyl-ethoxy)-ethyl)-furan-2-yl)-pyrido[3,4-d]pyrimidin-4-yl)-amine;
(4-(3-Fluorobenzyloxy)-3-chlorophenyl)-(6-(2-((2-propanesulphonyl-ethoxy)-propyl)-furan-2-yl)-pyrido[3,4-d]pyrimidin-4-yl)-amine;
(4-(3-Fluorobenzyloxy)-3-bromophenyl)-(6-(2-((2-propanesulphonyl-ethoxy)-propyl)-furan-2-yl)-pyrido[3,4-d]pyrimidin-4-yl)-amine;

List 86
(4-(3-Fluorobenzyloxy)-3-chlorophenyl)-(6-(2-((2-iso-propyl-sulphonyl-ethoxy)-methyl)-furan-2-yl)-pyrido[3,4-d]pyrimidin-4-yl)-amine;
(4-(3-Fluorobenzyloxy)-3-bromophenyl)-(6-(2-((2-iso-propyl-sulphonyl-ethoxy)-methyl)-furan-2-yl)-pyrido[3,4-d]pyrimidin-4-yl)-amine;
(4-(3-Fluorobenzyloxy)-3-chlorophenyl)-(6-(2-((2-iso-propyl-sulphonyl-ethoxy)-ethyl)-furan-2-yl)-pyrido[3,4-d]pyrimidin-4-yl)-amine;
(4-(3-Fluorobenzyloxy)-3-bromophenyl)-(6-(2-((2-iso-propyl-sulphonyl-ethoxy)-ethyl)-furan-2-yl)-pyrido[3,4-d]pyrimidin-4-yl)-amine;
(4-(3-Fluorobenzyloxy)-3-chlorophenyl)-(6-(2-((2-iso-propyl-sulphonyl-ethoxy)-propyl)-furan-2-yl)-pyrido[3,4-d]pyrimidin-4-yl)-amine;
(4-(3-Fluorobenzyloxy)-3-bromophenyl)-(6-(2-((2-iso-propyl-sulphonyl-ethoxy)-propyl)-furan-2-yl)-pyrido[3,4-d]pyrimidin-4-yl)-amine;

List 87
(4-(3-Fluorobenzyloxy)-3-chlorophenyl)-(6-(2-((2-propanesulphonyl-ethoxy)methyl)-thiazol-4-yl)-pyrido[3,4-d]pyrimidin-4-yl)-amine;
(4-(3-Fluorobenzyloxy)-3-bromophenyl)-(6-(2-((2-propanesulphonyl-ethoxy)methyl)-thiazol-4-yl)-pyrido[3,4-d]pyrimidin-4-yl)-amine;
(4-(3-Fluorobenzyloxy)-3-chlorophenyl)-(6-(2-((2-propanesulphonyl-ethoxy)ethyl)-thiazol-4-yl)-pyrido[3,4-d]pyrimidin-4-yl)-amine;
(4-(3-Fluorobenzyloxy)-3-bromophenyl)-(6-(2-((2-propanesulphonyl-ethoxy)ethyl)-thiazol-4-yl)-pyrido[3,4-d]pyrimidin-4-yl)-amine;
(4-(3-Fluorobenzyloxy)-3-chlorophenyl)-(6-(2-((2-propanesulphonyl-ethoxy)propyl)-thiazol-4-yl)-pyrido[3,4-d]pyrimidin-4-yl)-amine;
(4-(3-Fluorobenzyloxy)-3-bromophenyl)-(6-(2-((2-propanesulphonyl-ethoxy)propyl)-thiazol-4-yl)-pyrido[3,4-d]pyrimidin-4-yl)-amine;

List 88
(4-(3-Fluorobenzyloxy)-3-chlorophenyl)-(6-(2-((2-iso-propyl-sulphonyl-ethoxy)methyl)-thiazol-4-yl)-pyrido[3,4-d]pyrimidin-4-yl)-amine;
(4-(3-Fluorobenzyloxy)-3-bromophenyl)-(6-(2-((2-iso-propyl-sulphonyl-ethoxy)methyl)-thiazol-4-yl)-pyrido[3,4-d]pyrimidin-4-yl)-amine;
(4-(3-Fluorobenzyloxy)-3-chlorophenyl)-(6-(2-((2-iso-propyl-sulphonyl-ethoxy)ethyl)-thiazol-4-yl)-pyrido[3,4-d]pyrimidin-4-yl)-amine;
(4-(3-Fluorobenzyloxy)-3-bromophenyl)-(6-(2-((2-iso-propyl-sulphonyl-ethoxy)ethyl)-thiazol-4-yl)-pyrido[3,4-d]pyrimidin-4-yl)-amine;
(4-(3-Fluorobenzyloxy)-3-chlorophenyl)-(6-(2-((2-iso-propyl-sulphonyl-ethoxy)propyl)-thiazol-4-yl)-pyrido[3,4-d]pyrimidin-4-yl)-amine;

(4-(3-Fluorobenzyloxy)-3-bromophenyl)-(6-(2-((2-iso-propyl-sulphonyl-ethoxy)propyl)-thiazol-4-yl)-pyrido[3,4-d]pyrimidin-4-yl)-amine;

List 89
(4-(3-Fluorobenzyloxy)-3-chlorophenyl)-(6-(2-((2-ethanesulphonyl-ethylamino)-methyl)-furan-2-yl)-quinazolin-4-yl)-amine;
(4-(3-Fluorobenzyloxy)-3-bromophenyl)-(6-(2-((2-ethanesulphonyl-ethylamino)-methyl)-furan-2-yl)-quinazolin-4-yl)-amine;
(4-(3-Fluorobenzyloxy)-3-chlorophenyl)-(6-(2-((2-ethanesulphonyl-ethylamino)-ethyl)-furan-2-yl)-quinazolin-4-yl)-amine;
(4-(3-Fluorobenzyloxy)-3-bromophenyl)-(6-(2-((2-ethanesulphonyl-ethylamino)-ethyl)-furan-2-yl)-quinazolin-4-yl)-amine;
(4-(3-Fluorobenzyloxy)-3-chlorophenyl)-(6-(2-((2-ethanesulphonyl-ethylamino)-propyl)-furan-2-yl)-quinazolin-4-yl)-amine;
(4-(3-Fluorobenzyloxy)-3-bromophenyl)-(6-(2-((2-ethanesulphonyl-ethylamino)-propyl)-furan-2-yl)-quinazolin-4-yl)-amine;

List 90
(4-(3-Fluorobenzyloxy)-3-chlorophenyl)-(6-(2-((2-ethanesulphonyl-ethylamino)methyl)-thiazol-4-yl)-quinazolin-4-yl)-amine;
(4-(3-Fluorobenzyloxy)-3-bromophenyl)-(6-(2-((2-ethanesulphonyl-ethylamino)methyl)-thiazol-4-yl)-quinazolin-4-yl)-amine;
(4-(3-Fluorobenzyloxy)-3-chlorophenyl)-(6-(2-((2-ethanesulphonyl-ethylamino)ethyl)-thiazol-4-yl)-quinazolin-4-yl)-amine;
(4-(3-Fluorobenzyloxy)-3-bromophenyl)-(6-(2-((2-ethanesulphonyl-ethylamino)ethyl)-thiazol-4-yl)-quinazolin-4-yl)-amine;
(4-(3-Fluorobenzyloxy)-3-chlorophenyl)-(6-(2-((2-ethanesulphonyl-ethylamino)propyl)-thiazol-4-yl)-quinazolin-4-yl)-amine;
(4-(3-Fluorobenzyloxy)-3-bromophenyl)-(6-(2-((2-ethanesulphonyl-ethylamino)propyl)-thiazol-4-yl)-quinazolin-4-yl)-amine;

List 91
(4-(3-Fluorobenzyloxy)-3-bromophenyl)-(6-(2-((2-propanesulphonyl-ethylamino)-methyl)-furan-2-yl)-quinazolin-4-yl)-amine;
(4-(3-Fluorobenzyloxy)-3-chlorophenyl)-(6-(2-((2-propanesulphonyl-ethylamino)-ethyl)-furan-2-yl)-quinazolin-4-yl)-amine;
(4-(3-Fluorobenzyloxy)-3-bromophenyl)-(6-(2-((2-propanesulphonyl-ethylamino)-ethyl)-furan-2-yl)-quinazolin-4-yl)-amine;
(4-(3-Fluorobenzyloxy)-3-bromophenyl)-(6-(2-((2-propanesulphonyl-ethylamino)-propyl)-furan-2-yl)-quinazolin-4-yl)-amine;

List 92
(4-(3-Fluorobenzyloxy)-3-bromophenyl)-(6-(2-((2-iso-propyl-sulphonyl-ethylamino)-methyl)-furan-2-yl)-quinazolin-4-yl)-amine;
(4-(3-Fluorobenzyloxy)-3-chlorophenyl)-(6-(2-((2-iso-propyl-sulphonyl-ethylamino)-ethyl)-furan-2-yl)-quinazolin-4-yl)-amine;
(4-(3-Fluorobenzyloxy)-3-bromophenyl)-(6-(2-((2-iso-propyl-sulphonyl-ethylamino)-ethyl)-furan-2-yl)-quinazolin-4-yl)-amine;
(4-(3-Fluorobenzyloxy)-3-bromophenyl)-(6-(2-((2-iso-propyl-sulphonyl-ethylamino)-propyl)-furan-2-yl)-quinazolin-4-yl)-amine;

List 93
(4-(3-Fluorobenzyloxy)-3-chlorophenyl)-(6-(2-((2-propanesulphonyl-ethylamino)methyl)-thiazol-4-yl)-quinazolin-4-yl)-amine;
(4-(3-Fluorobenzyloxy)-3-bromophenyl)-(6-(2-((2-propanesulphonyl-ethylamino)methyl)-thiazol-4-yl)-quinazolin-4-yl)-amine;
(4-(3-Fluorobenzyloxy)-3-chlorophenyl)-(6-(2-((2-propanesulphonyl-ethylamino)ethyl)-thiazol-4-yl)-quinazolin-4-yl)-amine;
(4-(3-Fluorobenzyloxy)-3-bromophenyl)-(6-(2-((2-propanesulphonyl-ethylamino)ethyl)-thiazol-4-yl)-quinazolin-4-yl)-amine;
(4-(3-Fluorobenzyloxy)-3-chlorophenyl)-(6-(2-((2-propanesulphonyl-ethylamino)propyl)-thiazol-4-yl)-quinazolin-4-yl)-amine;
(4-(3-Fluorobenzyloxy)-3-bromophenyl)-(6-(2-((2-propanesulphonyl-ethylamino)propyl)-thiazol-4-yl)-quinazolin-4-yl)-amine;

List 94
(4-(3-Fluorobenzyloxy)-3-chlorophenyl)-(6-(2-((2-iso-propyl-sulphonyl-ethylamino)methyl)-thiazol-4-yl)-quinazolin-4-yl)-amine;
(4-(3-Fluorobenzyloxy)-3-bromophenyl)-(6-(2-((2-iso-propyl-sulphonyl-ethylamino)methyl)-thiazol-4-yl)-quinazolin-4-yl)-amine;
(4-(3-Fluorobenzyloxy)-3-chlorophenyl)-(6-(2-((2-iso-propyl-sulphonyl-ethylamino)ethyl)-thiazol-4-yl)-quinazolin-4-yl)-amine;
(4-(3-Fluorobenzyloxy)-3-bromophenyl)-(6-(2-((2-iso-propyl-sulphonyl-ethylamino)ethyl)-thiazol-4-yl)-quinazolin-4-yl)-amine;
(4-(3-Fluorobenzyloxy)-3-chlorophenyl)-(6-(2-((2-iso-propyl-sulphonyl-ethylamino)propyl)-thiazol-4-yl)-quinazolin-4-yl)-amine;
(4-(3-Fluorobenzyloxy)-3-bromophenyl)-(6-(2-((2-iso-propyl-sulphonyl-ethylamino)propyl)-thiazol-4-yl)-quinazolin-4-yl)-amine;

List 95
(4-(3-Fluorobenzyloxy)-3-chlorophenyl)-(6-(2-((2-methanesulphonyl-ethoxy)methyl)-furan-2-yl)-quinazolin-4-yl)-amine;
(4-(3-Fluorobenzyloxy)-3-bromophenyl)-(6-(2-((2-methanesulphonyl-ethoxy)methyl)-furan-2-yl)-quinazolin-4-yl)-amine;
(4-(3-Fluorobenzyloxy)-3-chlorophenyl)-(6-(2-((2-methanesulphonyl-ethoxy)ethyl)-furan-2-yl)-quinazolin-4-yl)-amine;
(4-(3-Fluorobenzyloxy)-3-chlorophenyl)-(6-(2-((2-methanesulphonyl-ethoxy)propyl)-furan-2-yl)-quinazolin-4-yl)-amine;
(4-(3-Fluorobenzyloxy)-3-bromophenyl)-(6-(2-((2-methanesulphonyl-ethoxy)propyl)-furan-2-yl)-quinazolin-4-yl)-amine;

List 96
(4-(3-Fluorobenzyloxy)-3-chlorophenyl)-(6-(2-((2-methanesulphonyl-ethoxy)methyl)-thiazol-4-yl)-quinazolin-4-yl)-amine;
(4-(3-Fluorobenzyloxy)-3-bromophenyl)-(6-(2-((2-methanesulphonyl-ethoxy)methyl)-thiazol-4-yl)-quinazolin-4-yl)-amine;

(4-(3-Fluorobenzyloxy)-3-chlorophenyl)-(6-(2-((2-methanesulphonyl-ethoxy)ethyl)-thiazol-4-yl)-quinazolin-4-yl)-amine;
(4-(3-Fluorobenzyloxy)-3-bromophenyl)-(6-(2-((2-methanesulphonyl-ethoxy)ethyl)-thiazol-4-yl)-quinazolin-4-yl)-amine;
(4-(3-Fluorobenzyloxy)-3-chlorophenyl)-(6-(2-((2-methanesulphonyl-ethoxy)propyl)-thiazol-4-yl)-quinazolin-4-yl)-amine;
(4-(3-Fluorobenzyloxy)-3-bromophenyl)-(6-(2-((2-methanesulphonyl-ethoxy)propyl)-thiazol-4-yl)-quinazolin-4-yl)-amine;

List 97
(4-(3-Fluorobenzyloxy)-3-chlorophenyl)-(6-(2-((2-ethanesulphonyl-ethoxy)-methyl)-furan-2-yl)-quinazolin-4-yl)-amine;
(4-(3-Fluorobenzyloxy)-3-bromophenyl)-(6-(2-((2-ethanesulphonyl-ethoxy)-methyl)-furan-2-yl)-quinazolin-4-yl)-amine;
(4-(3-Fluorobenzyloxy)-3-chlorophenyl)-(6-(2-((2-ethanesulphonyl-ethoxy)-ethyl)-furan-2-yl)-quinazolin-4-yl)-amine;
(4-(3-Fluorobenzyloxy)-3-bromophenyl)-(6-(2-((2-ethanesulphonyl-ethoxy)-ethyl)-furan-2-yl)-quinazolin-4-yl)-amine;
(4-(3-Fluorobenzyloxy)-3-chlorophenyl)-(6-(2-((2-ethanesulphonyl-ethoxy)-propyl)-furan-2-yl)-quinazolin-4-yl)-amine;
(4-(3-Fluorobenzyloxy)-3-bromophenyl)-(6-(2-((2-ethanesulphonyl-ethoxy)-propyl)-furan-2-yl)-quinazolin-4-yl)-amine;

List 98
(4-(3-Fluorobenzyloxy)-3-chlorophenyl)-(6-(2-((2-ethanesulphonyl-ethoxy)methyl)-thiazol-4-yl)-quinazolin-4-yl)-amine;
(4-(3-Fluorobenzyloxy)-3-bromophenyl)-(6-(2-((2-ethanesulphonyl-ethoxy)methyl)-thiazol-4-yl)-quinazolin-4-yl)-amine;
(4-(3-Fluorobenzyloxy)-3-chlorophenyl)-(6-(2-((2-ethanesulphonyl-ethoxy)ethyl)-thiazol-4-yl)-quinazolin-4-yl)-amine;
(4-(3-Fluorobenzyloxy)-3-bromophenyl)-(6-(2-((2-ethanesulphonyl-ethoxy)ethyl)-thiazol-4-yl)-quinazolin-4-yl)-amine
(4-(3-Fluorobenzyloxy)-3-chlorophenyl)-(6-(2-((2-ethanesulphonyl-ethoxy)propyl)-thiazol-4-yl)-quinazolin-4-yl)-amine;
(4-(3-Fluorobenzyloxy)-3-bromophenyl)-(6-(2-((2-ethanesulphonyl-ethoxy)propyl)-thiazol-4-yl)-quinazolin-4-yl)-amine List 99
(4-(3-Fluorobenzyloxy)-3-chlorophenyl)-(6-(2-((2-propanesulphonyl-ethoxy)-methyl)-furan-2-yl)-quinazolin-4-yl)-amine;
(4-(3-Fluorobenzyloxy)-3-bromophenyl)-(6-(2-((2-propanesulphonyl-ethoxy)-methyl)-furan-2-yl)-quinazolin-4-yl)-amine;
(4-(3-Fluorobenzyloxy)-3-chlorophenyl)-(6-(2-((2-propanesulphonyl-ethoxy)-ethyl)-furan-2-yl)-quinazolin-4-yl)-amine;
(4-(3-Fluorobenzyloxy)-3-bromophenyl)-(6-(2-((2-propanesulphonyl-ethoxy)-ethyl)-furan-2-yl)-quinazolin-4-yl)-amine;
(4-(3-Fluorobenzyloxy)-3-chlorophenyl)-(6-(2-((2-propanesulphonyl-ethoxy)-propyl)-furan-2-yl)-quinazolin-4-yl)-amine;
(4-(3-Fluorobenzyloxy)-3-bromophenyl)-(6-(2-((2-propanesulphonyl-ethoxy)-propyl)-furan-2-yl)-quinazolin-4-yl)-amine;

List 100
(4-(3-Fluorobenzyloxy)-3-chlorophenyl)-(6-(2-((2-iso-propyl-sulphonyl-ethoxy)-methyl)-furan-2-yl)-quinazolin-4-yl)-amine;
(4-(3-Fluorobenzyloxy)-3-bromophenyl)-(6-(2-((2-iso-propyl-sulphonyl-ethoxy)-methyl)-furan-2-yl)-quinazolin-4-yl)-amine;
(4-(3-Fluorobenzyloxy)-3-chlorophenyl)-(6-(2-((2-iso-propyl-sulphonyl-ethoxy)-ethyl)-furan-2-yl)-quinazolin-4-yl)-amine;
(4-(3-Fluorobenzyloxy)-3-bromophenyl)-(6-(2-((2-iso-propyl-sulphonyl-ethoxy)-ethyl)-furan-2-yl)-quinazolin-4-yl)-amine;
(4-(3-Fluorobenzyloxy)-3-chlorophenyl)-(6-(2-((2-iso-propyl-sulphonyl-ethoxy)-propyl)-furan-2-yl)-quinazolin-4-yl)-amine;
(4-(3-Fluorobenzyloxy)-3-bromophenyl)-(6-(2-((2-iso-propyl-sulphonyl-ethoxy)-propyl)-furan-2-yl)-quinazolin-4-yl)-amine;

List 101
(4-(3-Fluorobenzyloxy)-3-chlorophenyl)-(6-(2-((2-propanesulphonyl-ethoxy)methyl)-thiazol-4-yl)-quinazolin-4-yl)-amine;
(4-(3-Fluorobenzyloxy)-3-bromophenyl)-(6-(2-((2-propanesulphonyl-ethoxy)methyl)-thiazol-4-yl)-quinazolin-4-yl)-amine;
(4-(3-Fluorobenzyloxy)-3-chlorophenyl)-(6-(2-((2-propanesulphonyl-ethoxy)ethyl)-thiazol-4-yl)-quinazolin-4-yl)-amine;
(4-(3-Fluorobenzyloxy)-3-bromophenyl)-(6-(2-((2-propanesulphonyl-ethoxy)ethyl)-thiazol-4-yl)-quinazolin-4-yl)-amine;
(4-(3-Fluorobenzyloxy)-3-chlorophenyl)-(6-(2-((2-propanesulphonyl-ethoxy)propyl)-thiazol-4-yl)-quinazolin-4-yl)-amine;
(4-(3-Fluorobenzyloxy)-3-bromophenyl)-(6-(2-((2-propanesulphonyl-ethoxy)propyl)-thiazol-4-yl)-quinazolin-4-yl)-amine;

List 102
(4-(3-Fluorobenzyloxy)-3-chlorophenyl)-(6-(2-((2-iso-propyl-sulphonyl-ethoxy)methyl)-thiazol-4-yl)-quinazolin-4-yl)-amine;
(4-(3-Fluorobenzyloxy)-3-bromophenyl)-(6-(2-((2-iso-propyl-sulphonyl-ethoxy)methyl)-thiazol-4-yl)-quinazolin-4-yl)-amine;
(4-(3-Fluorobenzyloxy)-3-chlorophenyl)-(6-(2-((2-iso-propyl-sulphonyl-ethoxy)ethyl)-thiazol-4-yl)-quinazolin-4-yl)-amine;
(4-(3-Fluorobenzyloxy)-3-bromophenyl)-(6-(2-((2-iso-propyl-sulphonyl-ethoxy)ethyl)-thiazol-4-yl)-quinazolin-4-yl)-amine;
(4-(3-Fluorobenzyloxy)-3-chlorophenyl)-(6-(2-((2-iso-propyl-sulphonyl-ethoxy)propyl)-thiazol-4-yl)-quinazolin-4-yl)-amine;
(4-(3-Fluorobenzyloxy)-3-bromophenyl)-(6-(2-((2-iso-propyl-sulphonyl-ethoxy)propyl)-thiazol-4-yl)-quinazolin-4-yl)-amine;

List 103
(4-(3-Fluorobenzyloxy)-3-chlorophenyl)-(6-(2-((2-methanesulphonyl-ethylamino)-ethyl)-furan-2-yl)-7-methoxy-quinazolin-4-yl)-amine;
(4-(3-Fluorobenzyloxy)-3-bromophenyl)-(6-(2-((2-methanesulphonyl-ethylamino)-ethyl)-furan-2-yl)-7-methoxy-quinazolin-4-yl)-amine;
(4-(3-Fluorobenzyloxy)-3-chlorophenyl)-(6-(2-((2-methanesulphonyl-ethylamino)-propyl)-furan-2-yl)-7-methoxy-quinazolin-4-yl)-amine;
(4-(3-Fluorobenzyloxy)-3-bromophenyl)-(6-(2-((2-methanesulphonyl-ethylamino)-propyl)-furan-2-yl)-7-methoxy-quinazolin-4-yl)-amine;

List 104
(4-(3-Fluorobenzyloxy)-3-chlorophenyl)-(6-(2-((2-methanesulphonyl-ethylamino)ethyl)-thiazol-4-yl)-7-methoxy-quinazolin-4-yl)-amine;
(4-(3-Fluorobenzyloxy)-3-bromophenyl)-(6-(2-((2-methanesulphonyl-ethylamino)ethyl)-thiazol-4-yl)-7-methoxy-quinazolin-4-yl)-amine;
(4-(3-Fluorobenzyloxy)-3-chlorophenyl)-(6-(2-((2-methanesulphonyl-ethylamino)propyl)-thiazol-4-yl)-7-methoxy-quinazolin-4-yl)-amine;
(4-(3-Fluorobenzyloxy)-3-bromophenyl)-(6-(2-((2-methanesulphonyl-ethylamino)propyl)-thiazol-4-yl)-7-methoxy-quinazolin-4-yl)-amine;

List 105
(4-(3-Fluorobenzyloxy)-3-chlorophenyl)-(6-(2-((2-ethanesulphonyl-ethylamino)-methyl)-furan-2-yl)-7-methoxy-quinazolin-4-yl)-amine;
(4-(3-Fluorobenzyloxy)-3-bromophenyl)-(6-(2-((2-ethanesulphonyl-ethylamino)-methyl)-furan-2-yl)-7-methoxy-quinazolin-4-yl)-amine;
(4-(3-Fluorobenzyloxy)-3-chlorophenyl)-(6-(2-((2-ethanesulphonyl-ethylamino)-ethyl)-furan-2-yl)-7-methoxy-quinazolin-4-yl)-amine;
(4-(3-Fluorobenzyloxy)-3-bromophenyl)-(6-(2-((2-ethanesulphonyl-ethylamino)-ethyl)-furan-2-yl)-7-methoxy-quinazolin-4-yl)-amine;
(4-(3-Fluorobenzyloxy)-3-chlorophenyl)-(6-(2-((2-ethanesulphonyl-ethylamino)-propyl)-furan-2-yl)-7-methoxy-quinazolin-4-yl)-amine;
(4-(3-Fluorobenzyloxy)-3-bromophenyl)-(6-(2-((2-ethanesulphonyl-ethylamino)-propyl)-furan-2-yl)-7-methoxy-quinazolin-4-yl)-amine;

List 106
(4-(3-Fluorobenzyloxy)-3-chlorophenyl)-(6-(2-((2-ethanesulphonyl-ethylamino)methyl)-thiazol-4-yl)-7-methoxy-quinazolin-4-yl)-amine;
(4-(3-Fluorobenzyloxy)-3-bromophenyl)-(6-(2-((2-ethanesulphonyl-ethylamino)methyl)-thiazol-4-yl)-7-methoxy-quinazolin-4-yl)-amine;
(4-(3-Fluorobenzyloxy)-3-chlorophenyl)-(6-(2-((2-ethanesulphonyl-ethylamino)ethyl)-thiazol-4-yl)-7-methoxy-quinazolin-4-yl)-amine;
(4-(3-Fluorobenzyloxy)-3-bromophenyl)-(6-(2-((2-ethanesulphonyl-ethylamino)ethyl)-thiazol-4-yl)-7-methoxy-quinazolin-4-yl)-amine;
(4-(3-Fluorobenzyloxy)-3-chlorophenyl)-(6-(2-((2-ethanesulphonyl-ethylamino)propyl)-thiazol-4-yl)-7-methoxy-quinazolin-4-yl)-amine;
(4-(3-Fluorobenzyloxy)-3-bromophenyl)-(6-(2-((2-ethanesulphonyl-ethylamino)propyl)-thiazol-4-yl)-7-methoxy-quinazolin-4-yl)-amine;

List 107
(4-(3-Fluorobenzyloxy)-3-chlorophenyl)-(6-(2-((2-propanesulphonyl-ethylamino)-methyl)-furan-2-yl)-7-methoxy-quinazolin-4-yl)-amine;
(4-(3-Fluorobenzyloxy)-3-bromophenyl)-(6-(2-((2-propanesulphonyl-ethylamino)-methyl)-furan-2-yl)-7-methoxy-quinazolin-4-yl)-amine;
(4-(3-Fluorobenzyloxy)-3-chlorophenyl)-(6-(2-((2-propanesulphonyl-ethylamino)-ethyl)-furan-2-yl)-7-methoxy-quinazolin-4-yl)-amine;
(4-(3-Fluorobenzyloxy)-3-bromophenyl)-(6-(2-((2-propanesulphonyl-ethylamino)-ethyl)-furan-2-yl)-7-methoxy-quinazolin-4-yl)-amine;
(4-(3-Fluorobenzyloxy)-3-chlorophenyl)-(6-(2-((2-propanesulphonyl-ethylamino)-propyl)-furan-2-yl)-7-methoxy-quinazolin-4-yl)-amine;
(4-(3-Fluorobenzyloxy)-3-bromophenyl)-(6-(2-((2-propanesulphonyl-ethylamino)-propyl)-furan-2-yl)-7-methoxy-quinazolin-4-yl)-amine;

List 108
(4-(3-Fluorobenzyloxy)-3-chlorophenyl)-(6-(2-((2-iso-propyl-sulphonyl-ethylamino)-methyl)-furan-2-yl)-7-methoxy-quinazolin-4-yl)-amine;
(4-(3-Fluorobenzyloxy)-3-bromophenyl)-(6-(2-((2-iso-propyl-sulphonyl-ethylamino)-methyl)-furan-2-yl)-7-methoxy-quinazolin-4-yl)-amine;
(4-(3-Fluorobenzyloxy)-3-chlorophenyl)-(6-(2-((2-iso-propyl-sulphonyl-ethylamino)-ethyl)-furan-2-yl)-7-methoxy-quinazolin-4-yl)-amine;
(4-(3-Fluorobenzyloxy)-3-bromophenyl)-(6-(2-((2-iso-propyl-sulphonyl-ethylamino)-ethyl)-furan-2-yl)-7-methoxy-quinazolin-4-yl)-amine;
(4-(3-Fluorobenzyloxy)-3-chlorophenyl)-(6-(2-((2-iso-propyl-sulphonyl-ethylamino)-propyl)-furan-2-yl)-7-methoxy-quinazolin-4-yl)-amine;
(4-(3-Fluorobenzyloxy)-3-bromophenyl)-(6-(2-((2-iso-propyl-sulphonyl-ethylamino)-propyl)-furan-2-yl)-7-methoxy-quinazolin-4-yl)-amine;

List 109
(4-(3-Fluorobenzyloxy)-3-chlorophenyl)-(6-(2-((2-propanesulphonyl-ethylamino)methyl)-thiazol-4-yl)-7-methoxy-quinazolin-4-yl)-amine;
(4-(3-Fluorobenzyloxy)-3-bromophenyl)-(6-(2-((2-propanesulphonyl-ethylamino)methyl)-thiazol-4-yl)-7-methoxy-quinazolin-4-yl)-amine;
(4-(3-Fluorobenzyloxy)-3-chlorophenyl)-(6-(2-((2-propanesulphonyl-ethylamino)ethyl)-thiazol-4-yl)-7-methoxy-quinazolin-4-yl)-amine;
(4-(3-Fluorobenzyloxy)-3-bromophenyl)-(6-(2-((2-propanesulphonyl-ethylamino)ethyl)-thiazol-4-yl)-7-methoxy-quinazolin-4-yl)-amine;
(4-(3-Fluorobenzyloxy)-3-chlorophenyl)-(6-(2-((2-propanesulphonyl-ethylamino)propyl)-thiazol-4-yl)-7-methoxy-quinazolin-4-yl)-amine;
(4-(3-Fluorobenzyloxy)-3-bromophenyl)-(6-(2-((2-propanesulphonyl-ethylamino)propyl)-thiazol-4-yl)-7-methoxy-quinazolin-4-yl)-amine;

List 110
(4-(3-Fluorobenzyloxy)-3-chlorophenyl)-(6-(2-((2-iso-propyl-sulphonyl-ethylamino)methyl)-thiazol-4-yl)-7-methoxy-quinazolin-4-yl)-amine;
(4-(3-Fluorobenzyloxy)-3-bromophenyl)-(6-(2-((2-iso-propyl-sulphonyl-ethylamino)methyl)-thiazol-4-yl)-7-methoxy-quinazolin-4-yl)-amine;

(4-(3-Fluorobenzyloxy)-3-chlorophenyl)-(6-(2-((2-iso-propyl-sulphonyl-ethylamino)ethyl)-thiazol-4-yl)-7-methoxy-quinazolin-4-yl)-amine;

(4-(3-Fluorobenzyloxy)-3-bromophenyl)-(6-(2-((2-iso-propyl-sulphonyl-ethylamino)ethyl)-thiazol-4-yl)-7-methoxy-quinazolin-4-yl)-amine;

(4-(3-Fluorobenzyloxy)-3-chlorophenyl)-(6-(2-((2-iso-propyl-sulphonyl-ethylamino)propyl)-thiazol-4-yl)-7-methoxy-quinazolin-4-yl)-amine;

(4-(3-Fluorobenzyloxy)-3-bromophenyl)-(6-(2-((2-iso-propyl-sulphonyl-ethylamino)propyl)-thiazol-4-yl)-7-methoxy-quinazolin-4-yl)-amine;

List 111

(4-(3-Fluorobenzyloxy)-3-chlorophenyl)-(6-(2-((2-methanesulphonyl-ethoxy)methyl)-furan-2-yl)-7-methoxy-quinazolin-4-yl)-amine;

(4-(3-Fluorobenzyloxy)-3-bromophenyl)-(6-(2-((2-methanesulphonyl-ethoxy)methyl)-furan-2-yl)-7-methoxy-quinazolin-4-yl)-amine;

(4-(3-Fluorobenzyloxy)-3-chlorophenyl)-(6-(2-((2-methanesulphonyl-ethoxy)ethyl)-furan-2-yl)-7-methoxy-quinazolin-4-yl)-amine;

(4-(3-Fluorobenzyloxy)-3-bromophenyl)-(6-(2-((2-methanesulphonyl-ethoxy)ethyl)-furan-2-yl)-7-methoxy-quinazolin-4-yl)-amine;

(4-(3-Fluorobenzyloxy)-3-chlorophenyl)-(6-(2-((2-methanesulphonyl-ethoxy)propyl)-furan-2-yl)-7-methoxy-quinazolin-4-yl)-amine;

(4-(3-Fluorobenzyloxy)-3-bromophenyl)-(6-(2-((2-methanesulphonyl-ethoxy)propyl)-furan-2-yl)-7-methoxy-quinazolin-4-yl)-amine;

List 112

(4-(3-Fluorobenzyloxy)-3-chlorophenyl)-(6-(2-((2-methanesulphonyl-ethoxy)methyl)-thiazol-4-yl)-7-methoxy-quinazolin-4-yl)-amine;

(4-(3-Fluorobenzyloxy)-3-bromophenyl)-(6-(2-((2-methanesulphonyl-ethoxy)methyl)-thiazol-4-yl)-7-methoxy-quinazolin-4-yl)-amine;

(4-(3-Fluorobenzyloxy)-3-chlorophenyl)-(6-(2-((2-methanesulphonyl-ethoxy)ethyl)-thiazol-4-yl)-7-methoxy-quinazolin-4-yl)-amine;

(4-(3-Fluorobenzyloxy)-3-bromophenyl)-(6-(2-((2-methanesulphonyl-ethoxy)ethyl)-thiazol-4-yl)-7-methoxy-quinazolin-4-yl)-amine;

(4-(3-Fluorobenzyloxy)-3-chlorophenyl)-(6-(2-((2-methanesulphonyl-ethoxy)propyl)-thiazol-4-yl)-7-methoxy-quinazolin-4-yl)-amine;

(4-(3-Fluorobenzyloxy)-3-bromophenyl)-(6-(2-((2-methanesulphonyl-ethoxy)propyl)-thiazol-4-yl)-7-methoxy-quinazolin-4-yl)-amine;

List 113

(4-(3-Fluorobenzyloxy)-3-chlorophenyl)-(6-(2-((2-ethanesulphonyl-ethoxy)-methyl)-furan-2-yl)-7-methoxy-quinazolin-4-yl)-amine;

(4-(3-Fluorobenzyloxy)-3-bromophenyl)-(6-(2-((2-ethanesulphonyl-ethoxy)-methyl)-furan-2-yl)-7-methoxy-quinazolin-4-yl)-amine;

(4-(3-Fluorobenzyloxy)-3-chlorophenyl)-(6-(2-((2-ethanesulphonyl-ethoxy)-ethyl)-furan-2-yl)-7-methoxy-quinazolin-4-yl)-amine;

(4-(3-Fluorobenzyloxy)-3-bromophenyl)-(6-(2-((2-ethanesulphonyl-ethoxy)-ethyl)-furan-2-yl)-7-methoxy-quinazolin-4-yl)-amine;

(4-(3-Fluorobenzyloxy)-3-chlorophenyl)-(6-(2-((2-ethanesulphonyl-ethoxy)-propyl)-furan-2-yl)-7-methoxy-quinazolin-4-yl)-amine;

(4-(3-Fluorobenzyloxy)-3-bromophenyl)-(6-(2-((2-ethanesulphonyl-ethoxy)-propyl)-furan-2-yl)-7-methoxy-quinazolin-4-yl)-amine;

List 114

(4-(3-Fluorobenzyloxy)-3-chlorophenyl)-(6-(2-((2-ethanesulphonyl-ethoxy)methyl)-thiazol-4-yl)-7-methoxy-quinazolin-4-yl)-amine;

(4-(3-Fluorobenzyloxy)-3-bromophenyl)-(6-(2-((2-ethanesulphonyl-ethoxy)methyl)-thiazol-4-yl)-7-methoxy-quinazolin-4-yl)-amine;

(4-(3-Fluorobenzyloxy)-3-chlorophenyl)-(6-(2-((2-ethanesulphonyl-ethoxy)ethyl)-thiazol-4-yl)-7-methoxy-quinazolin-4-yl)-amine;

(4-(3-Fluorobenzyloxy)-3-bromophenyl)-(6-(2-((2-ethanesulphonyl-ethoxy)ethyl)-thiazol-4-yl)-7-methoxy-quinazolin-4-yl)-amine;

(4-(3-Fluorobenzyloxy)-3-chlorophenyl)-(6-(2-((2-ethanesulphonyl-ethoxy)propyl)-thiazol-4-yl)-7-methoxy-quinazolin-4-yl)-amine;

(4-(3-Fluorobenzyloxy)-3-bromophenyl)-(6-(2-((2-ethanesulphonyl-ethoxy)propyl)-thiazol-4-yl)-7-methoxy-quinazolin-4-yl)-amine;

List 115

(4-(3-Fluorobenzyloxy)-3-chlorophenyl)-(6-(2-((2-propanesulphonyl-ethoxy)-methyl)-furan-2-yl)-7-methoxy-quinazolin-4-yl)-amine;

(4-(3-Fluorobenzyloxy)-3-bromophenyl)-(6-(2-((2-propanesulphonyl-ethoxy)-methyl)-furan-2-yl)-7-methoxy-quinazolin-4-yl)-amine;

(4-(3-Fluorobenzyloxy)-3-chlorophenyl)-(6-(2-((2-propanesulphonyl-ethoxy)-ethyl)-furan-2-yl)-7-methoxy-quinazolin-4-yl)-amine;

(4-(3-Fluorobenzyloxy)-3-bromophenyl)-(6-(2-((2-propanesulphonyl-ethoxy)-ethyl)-furan-2-yl)-7-methoxy-quinazolin-4-yl)-amine;

(4-(3-Fluorobenzyloxy)-3-chlorophenyl)-(6-(2-((2-propanesulphonyl-ethoxy)-propyl)-furan-2-yl)-7-methoxy-quinazolin-4-yl)-amine;

(4-(3-Fluorobenzyloxy)-3-bromophenyl)-(6-(2-((2-propanesulphonyl-ethoxy)-propyl)-furan-2-yl)-7-methoxy-quinazolin-4-yl)-amine;

List 116

(4-(3-Fluorobenzyloxy)-3-chlorophenyl)-(6-(2-((2-iso-propyl-sulphonyl-ethoxy)-methyl)-furan-2-yl)-7-methoxy-quinazolin-4-yl)-amine;

(4-(3-Fluorobenzyloxy)-3-bromophenyl)-(6-(2-((2-iso-propyl-sulphonyl-ethoxy)-methyl)-furan-2-yl)-7-methoxy-quinazolin-4-yl)-amine;

(4-(3-Fluorobenzyloxy)-3-chlorophenyl)-(6-(2-((2-iso-propyl-sulphonyl-ethoxy)-ethyl)-furan-2-yl)-7-methoxy-quinazolin-4-yl)-amine;

(4-(3-Fluorobenzyloxy)-3-bromophenyl)-(6-(2-((2-iso-propyl-sulphonyl-ethoxy)-ethyl)-furan-2-yl)-7-methoxy-quinazolin-4-yl)-amine;

(4-(3-Fluorobenzyloxy)-3-chlorophenyl)-(6-(2-((2-iso-propyl-sulphonyl-ethoxy)-propyl)-furan-2-yl)-7-methoxy-quinazolin-4-yl)-amine;

(4-(3-Fluorobenzyloxy)-3-bromophenyl)-(6-(2-((2-iso-propyl-sulphonyl-ethoxy)-propyl)-furan-2-yl)-7-methoxy-quinazolin-4-yl)-amine;

List 117
(4-(3-Fluorobenzyloxy)-3-chlorophenyl)-(6-(2-((2-propane-sulphonyl-ethoxy)methyl)-thiazol-4-yl)-7-methoxy-quinazolin-4-yl)-amine;
(4-(3-Fluorobenzyloxy)-3-bromophenyl)-(6-(2-((2-propanesulphonyl-ethoxy)methyl)-thiazol-4-yl)-7-methoxy-quinazolin-4-yl)-amine;
(4-(3-Fluorobenzyloxy)-3-chlorophenyl)-(6-(2-((2-propane-sulphonyl-ethoxy)ethyl)-thiazol-4-yl)-7-methoxy-quinazolin-4-yl)-amine;
(4-(3-Fluorobenzyloxy)-3-bromophenyl)-(6-(2-((2-propanesulphonyl-ethoxy)ethyl)-thiazol-4-yl)-7-methoxy-quinazolin-4-yl)-amine;
(4-(3-Fluorobenzyloxy)-3-chlorophenyl)-(6-(2-((2-propane-sulphonyl-ethoxy)propyl)-thiazol-4-yl)-7-methoxy-quinazolin-4-yl)-amine;
(4-(3-Fluorobenzyloxy)-3-bromophenyl)-(6-(2-((2-propanesulphonyl-ethoxy)propyl)-thiazol-4-yl)-7-methoxy-quinazolin-4-yl)-amine;

List 118
(4-(3-Fluorobenzyloxy)-3-chlorophenyl)-(6-(2-((2-iso-propyl-sulphonyl-ethoxy)methyl)-thiazol-4-yl)-7-methoxy-quinazolin-4-yl)-amine;
(4-(3-Fluorobenzyloxy)-3-bromophenyl)-(6-(2-((2-iso-propyl-sulphonyl-ethoxy)methyl)-thiazol-4-yl)-7-methoxy-quinazolin-4-yl)-amine;
(4-(3-Fluorobenzyloxy)-3-chlorophenyl)-(6-(2-((2-iso-propyl-sulphonyl-ethoxy)ethyl)-thiazol-4-yl)-7-methoxy-quinazolin-4-yl)-amine;
(4-(3-Fluorobenzyloxy)-3-bromophenyl)-(6-(2-((2-iso-propyl-sulphonyl-ethoxy)ethyl)-thiazol-4-yl)-7-methoxy-quinazolin-4-yl)-amine;
(4-(3-Fluorobenzyloxy)-3-chlorophenyl)-(6-(2-((2-iso-propyl-sulphonyl-ethoxy)propyl)-thiazol-4-yl)-7-methoxy-quinazolin-4-yl)-amine;
(4-(3-Fluorobenzyloxy)-3-bromophenyl)-(6-(2-((2-iso-propyl-sulphonyl-ethoxy)propyl)-thiazol-4-yl)-7-methoxy-quinazolin-4-yl)-amine;

List 119
(4-(3-Fluorobenzyloxy)-3-chlorophenyl)-(6-(2-((2-ethane-sulphonyl-ethylamino)-methyl)-furan-2-yl)-7-fluoro-quinazolin-4-yl)-amine;
(4-(3-Fluorobenzyloxy)-3-bromophenyl)-(6-(2-((2-ethane-sulphonyl-ethylamino)-methyl)-furan-2-yl)-7-fluoro-quinazolin-4-yl)-amine;
(4-(3-Fluorobenzyloxy)-3-chlorophenyl)-(6-(2-((2-ethane-sulphonyl-ethylamino)-ethyl)-furan-2-yl)-7-fluoro-quinazolin-4-yl)-amine;
(4-(3-Fluorobenzyloxy)-3-bromophenyl)-(6-(2-((2-ethane-sulphonyl-ethylamino)-ethyl)-furan-2-yl)-7-fluoro-quinazolin-4-yl)-amine;
(4-(3-Fluorobenzyloxy)-3-chlorophenyl)-(6-(2-((2-ethane-sulphonyl-ethylamino)-propyl)-furan-2-yl)-7-fluoro-quinazolin-4-yl)-amine;
(4-(3-Fluorobenzyloxy)-3-bromophenyl)-(6-(2-((2-ethane-sulphonyl-ethylamino)-propyl)-furan-2-yl)-7-fluoro-quinazolin-4-yl)-amine;

List 120
(4-(3-Fluorobenzyloxy)-3-chlorophenyl)-(6-(2-((2-ethane-sulphonyl-ethylamino)methyl)-thiazol-4-yl)-7-fluoro-quinazolin-4-yl)-amine;
(4-(3-Fluorobenzyloxy)-3-bromophenyl)-(6-(2-((2-ethane-sulphonyl-ethylamino)methyl)-thiazol-4-yl)-7-fluoro-quinazolin-4-yl)-amine;
(4-(3-Fluorobenzyloxy)-3-chlorophenyl)-(6-(2-((2-ethane-sulphonyl-ethylamino)ethyl)-thiazol-4-yl)-7-fluoro-quinazolin-4-yl)-amine;
(4-(3-Fluorobenzyloxy)-3-bromophenyl)-(6-(2-((2-ethane-sulphonyl-ethylamino)ethyl)-thiazol-4-yl)-7-fluoro-quinazolin-4-yl)-amine;
(4-(3-Fluorobenzyloxy)-3-chlorophenyl)-(6-(2-((2-ethane-sulphonyl-ethylamino)propyl)-thiazol-4-yl)-7-fluoro-quinazolin-4-yl)-amine;
(4-(3-Fluorobenzyloxy)-3-bromophenyl)-(6-(2-((2-ethane-sulphonyl-ethylamino)propyl)-thiazol-4-yl)-7-fluoro-quinazolin-4-yl)-amine;

List 121
(4-(3-Fluorobenzyloxy)-3-chlorophenyl)-(6-(2-((2-propane-sulphonyl-ethylamino)-methyl)-furan-2-yl)-7-fluoro-quinazolin-4-yl)-amine;
(4-(3-Fluorobenzyloxy)-3-bromophenyl)-(6-(2-((2-propanesulphonyl-ethylamino)-methyl)-furan-2-yl)-7-fluoro-quinazolin-4-yl)-amine;
(4-(3-Fluorobenzyloxy)-3-chlorophenyl)-(6-(2-((2-propane-sulphonyl-ethylamino)-ethyl)-furan-2-yl)-7-fluoro-quinazolin-4-yl)-amine;
(4-(3-Fluorobenzyloxy)-3-bromophenyl)-(6-(2-((2-propanesulphonyl-ethylamino)-ethyl)-furan-2-yl)-7-fluoro-quinazolin-4-yl)-amine;
(4-(3-Fluorobenzyloxy)-3-chlorophenyl)-(6-(2-((2-propane-sulphonyl-ethylamino)-propyl)-furan-2-yl)-7-fluoro-quinazolin-4-yl)-amine;
(4-(3-Fluorobenzyloxy)-3-bromophenyl)-(6-(2-((2-propanesulphonyl-ethylamino)-propyl)-furan-2-yl)-7-fluoro-quinazolin-4-yl)-amine;

List 122
(4-(3-Fluorobenzyloxy)-3-chlorophenyl)-(6-(2-((2-iso-propyl-sulphonyl-ethylamino)-methyl)-furan-2-yl)-7-fluoro-quinazolin-4-yl)-amine;
(4-(3-Fluorobenzyloxy)-3-bromophenyl)-(6-(2-((2-iso-propyl-sulphonyl-ethylamino)-methyl)-furan-2-yl)-7-fluoro-quinazolin-4-yl)-amine;
(4-(3-Fluorobenzyloxy)-3-chlorophenyl)-(6-(2-((2-iso-propyl-sulphonyl-ethylamino)-ethyl)-furan-2-yl)-7-fluoro-quinazolin-4-yl)-amine;
(4-(3-Fluorobenzyloxy)-3-bromophenyl)-(6-(2-((2-iso-propyl-sulphonyl-ethylamino)-ethyl)-furan-2-yl)-7-fluoro-quinazolin-4-yl)-amine;
(4-(3-Fluorobenzyloxy)-3-chlorophenyl)-(6-(2-((2-iso-propyl-sulphonyl-ethylamino)-propyl)-furan-2-yl)-7-fluoro-quinazolin-4-yl)-amine;
(4-(3-Fluorobenzyloxy)-3-bromophenyl)-(6-(2-((2-iso-propyl-sulphonyl-ethylamino)-propyl)-furan-2-yl)-7-fluoro-quinazolin-4-yl)-amine;

List 123
(4-(3-Fluorobenzyloxy)-3-chlorophenyl)-(6-(2-((2-propane-sulphonyl-ethylamino)methyl)-thiazol-4-yl)-7-fluoro-quinazolin-4-yl)-amine;
(4-(3-Fluorobenzyloxy)-3-bromophenyl)-(6-(2-((2-propanesulphonyl-ethylamino)methyl)-thiazol-4-yl)-7-fluoro-quinazolin-4-yl)-amine;
(4-(3-Fluorobenzyloxy)-3-chlorophenyl)-(6-(2-((2-propane-sulphonyl-ethylamino)ethyl)-thiazol-4-yl)-7-fluoro-quinazolin-4-yl)-amine;
(4-(3-Fluorobenzyloxy)-3-bromophenyl)-(6-(2-((2-propanesulphonyl-ethylamino)ethyl)-thiazol-4-yl)-7-fluoro-quinazolin-4-yl)-amine;

(4-(3-Fluorobenzyloxy)-3-chlorophenyl)-(6-(2-((2-propane-sulphonyl-ethylamino)propyl)-thiazol-4-yl)-7-fluoro-quinazolin-4-yl)-amine;

(4-(3-Fluorobenzyloxy)-3-bromophenyl)-(6-(2-((2-propanesulphonyl-ethylamino)propyl)-thiazol-4-yl)-7-fluoro-quinazolin-4-yl)-amine;

List 124

(4-(3-Fluorobenzyloxy)-3-chlorophenyl)-(6-(2-((2-iso-propyl-sulphonyl-ethylamino)methyl)-thiazol-4-yl)-7-fluoro-quinazolin-4-yl)-amine;

(4-(3-Fluorobenzyloxy)-3-bromophenyl)-(6-(2-((2-iso-propyl-sulphonyl-ethylamino)methyl)-thiazol-4-yl)-7-fluoro-quinazolin-4-yl)-amine;

(4-(3-Fluorobenzyloxy)-3-chlorophenyl)-(6-(2-((2-iso-propyl-sulphonyl-ethylamino)ethyl)-thiazol-4-yl)-7-fluoro-quinazolin-4-yl)-amine;

(4-(3-Fluorobenzyloxy)-3-bromophenyl)-(6-(2-((2-iso-propyl-sulphonyl-ethylamino)ethyl)-thiazol-4-yl)-7-fluoro-quinazolin-4-yl)-amine;

(4-(3-Fluorobenzyloxy)-3-chlorophenyl)-(6-(2-((2-iso-propyl-sulphonyl-ethylamino)propyl)-thiazol-4-yl)-7-fluoro-quinazolin-4-yl)-amine;

(4-(3-Fluorobenzyloxy)-3-bromophenyl)-(6-(2-((2-iso-propyl-sulphonyl-ethylamino)propyl)-thiazol-4-yl)-7-fluoro-quinazolin-4-yl)-amine;

List 125

(4-(3-Fluorobenzyloxy)-3-chlorophenyl)-(6-(2-((2-methanesulphonyl-ethoxy)methyl)-furan-2-yl)-7-fluoro-quinazolin-4-yl)-amine;

(4-(3-Fluorobenzyloxy)-3-bromophenyl)-(6-(2-((2-methanesulphonyl-ethoxy)methyl)-furan-2-yl)-7-fluoro-quinazolin-4-yl)-amine;

(4-(3-Fluorobenzyloxy)-3-chlorophenyl)-(6-(2-((2-methanesulphonyl-ethoxy)ethyl)-furan-2-yl)-7-fluoro-quinazolin-4-yl)-amine;

(4-(3-Fluorobenzyloxy)-3-bromophenyl)-(6-(2-((2-methanesulphonyl-ethoxy)ethyl)-furan-2-yl)-7-fluoro-quinazolin-4-yl)-amine;

(4-(3-Fluorobenzyloxy)-3-chlorophenyl)-(6-(2-((2-methanesulphonyl-ethoxy)propyl)-furan-2-yl)-7-fluoro-quinazolin-4-yl)-amine;

(4-(3-Fluorobenzyloxy)-3-bromophenyl)-(6-(2-((2-methanesulphonyl-ethoxy)propyl)-furan-2-yl)-7-fluoro-quinazolin-4-yl)-amine;

List 126

(4-(3-Fluorobenzyloxy)-3-chlorophenyl)-(6-(2-((2-methanesulphonyl-ethoxy)methyl)-thiazol-4-yl)-7-fluoro-quinazolin-4-yl)-amine;

(4-(3-Fluorobenzyloxy)-3-bromophenyl)-(6-(2-((2-methanesulphonyl-ethoxy)methyl)-thiazol-4-yl)-7-fluoro-quinazolin-4-yl)-amine;

(4-(3-Fluorobenzyloxy)-3-chlorophenyl)-(6-(2-((2-methanesulphonyl-ethoxy)ethyl)-thiazol-4-yl)-7-fluoro-quinazolin-4-yl)-amine;

(4-(3-Fluorobenzyloxy)-3-bromophenyl)-(6-(2-((2-methanesulphonyl-ethoxy)ethyl)-thiazol-4-yl)-7-fluoro-quinazolin-4-yl)-amine;

(4-(3-Fluorobenzyloxy)-3-chlorophenyl)-(6-(2-((2-methanesulphonyl-ethoxy)propyl)-thiazol-4-yl)-7-fluoro-quinazolin-4-yl)-amine;

(4-(3-Fluorobenzyloxy)-3-bromophenyl)-(6-(2-((2-methanesulphonyl-ethoxy)propyl)-thiazol-4-yl)-7-fluoro-quinazolin-4-yl)-amine;

List 127

(4-(3-Fluorobenzyloxy)-3-chlorophenyl)-(6-(2-((2-ethanesulphonyl-ethoxy)-methyl)-furan-2-yl)-7-fluoro-quinazolin-4-yl)-amine;

(4-(3-Fluorobenzyloxy)-3-bromophenyl)-(6-(2-((2-ethanesulphonyl-ethoxy)-methyl)-furan-2-yl)-7-fluoro-quinazolin-4-yl)-amine;

(4-(3-Fluorobenzyloxy)-3-chlorophenyl)-(6-(2-((2-ethanesulphonyl-ethoxy)-ethyl)-furan-2-yl)-7-fluoro-quinazolin-4-yl)-amine;

(4-(3-Fluorobenzyloxy)-3-bromophenyl)-(6-(2-((2-ethanesulphonyl-ethoxy)-ethyl)-furan-2-yl)-7-fluoro-quinazolin-4-yl)-amine;

(4-(3-Fluorobenzyloxy)-3-chlorophenyl)-(6-(2-((2-ethanesulphonyl-ethoxy)-propyl)-furan-2-yl)-7-fluoro-quinazolin-4-yl)-amine;

(4-(3-Fluorobenzyloxy)-3-bromophenyl)-(6-(2-((2-ethanesulphonyl-ethoxy)-propyl)-furan-2-yl)-7-fluoro-quinazolin-4-yl)-amine;

List 128

(4-(3-Fluorobenzyloxy)-3-chlorophenyl)-(6-(2-((2-ethanesulphonyl-ethoxy)methyl)-thiazol-4-yl)-7-fluoro-quinazolin-4-yl)-amine;

(4-(3-Fluorobenzyloxy)-3-bromophenyl)-(6-(2-((2-ethanesulphonyl-ethoxy)methyl)-thiazol-4-yl)-7-fluoro-quinazolin-4-yl)-amine;

(4-(3-Fluorobenzyloxy)-3-chlorophenyl)-(6-(2-((2-ethanesulphonyl-ethoxy)ethyl)-thiazol-4-yl)-7-fluoro-quinazolin-4-yl)-amine;

(4-(3-Fluorobenzyloxy)-3-bromophenyl)-(6-(2-((2-ethanesulphonyl-ethoxy)ethyl)-thiazol-4-yl)-7-fluoro-quinazolin-4-yl)-amine;

(4-(3-Fluorobenzyloxy)-3-chlorophenyl)-(6-(2-((2-ethanesulphonyl-ethoxy)propyl)-thiazol-4-yl)-7-fluoro-quinazolin-4-yl)-amine;

(4-(3-Fluorobenzyloxy)-3-bromophenyl)-(6-(2-((2-ethanesulphonyl-ethoxy)propyl)-thiazol-4-yl)-7-fluoro-quinazolin-4-yl)-amine;

List 129

(4-(3-Fluorobenzyloxy)-3-chlorophenyl)-(6-(2-((2-propane-sulphonyl-ethoxy)-methyl)-furan-2-yl)-7-fluoro-quinazolin-4-yl)-amine;

(4-(3-Fluorobenzyloxy)-3-bromophenyl)-(6-(2-((2-propanesulphonyl-ethoxy)-methyl)-furan-2-yl)-7-fluoro-quinazolin-4-yl)-amine;

(4-(3-Fluorobenzyloxy)-3-chlorophenyl)-(6-(2-((2-propane-sulphonyl-ethoxy)-ethyl)-furan-2-yl)-7-fluoro-quinazolin-4-yl)-amine;

(4-(3-Fluorobenzyloxy)-3-bromophenyl)-(6-(2-((2-propanesulphonyl-ethoxy)-ethyl)-furan-2-yl)-7-fluoro-quinazolin-4-yl)-amine;

(4-(3-Fluorobenzyloxy)-3-chlorophenyl)-(6-(2-((2-propane-sulphonyl-ethoxy)-propyl)-furan-2-yl)-7-fluoro-quinazolin-4-yl)-amine;

(4-(3-Fluorobenzyloxy)-3-bromophenyl)-(6-(2-((2-propanesulphonyl-ethoxy)-propyl)-furan-2-yl)-7-fluoro-quinazolin-4-yl)-amine;

List 130

(4-(3-Fluorobenzyloxy)-3-chlorophenyl)-(6-(2-((2-iso-propyl-sulphonyl-ethoxy)-methyl)-furan-2-yl)-7-fluoro-quinazolin-4-yl)-amine;

(4-(3-Fluorobenzyloxy)-3-bromophenyl)-(6-(2-((2-iso-propyl-sulphonyl-ethoxy)-methyl)-furan-2-yl)-7-fluoro-quinazolin-4-yl)-amine;

(4-(3-Fluorobenzyloxy)-3-chlorophenyl)-(6-(2-((2-iso-propyl-sulphonyl-ethoxy)-ethyl)-furan-2-yl)-7-fluoro-quinazolin-4-yl)-amine;
(4-(3-Fluorobenzyloxy)-3-bromophenyl)-(6-(2-((2-iso-propyl-sulphonyl-ethoxy)-ethyl)-furan-2-yl)-7-fluoro-quinazolin-4-yl)-amine;
(4-(3-Fluorobenzyloxy)-3-chlorophenyl)-(6-(2-((2-iso-propyl-sulphonyl-ethoxy)-propyl)-furan-2-yl)-7-fluoro-quinazolin-4-yl)-amine;
(4-(3-Fluorobenzyloxy)-3-bromophenyl)-(6-(2-((2-iso-propyl-sulphonyl-ethoxy)-propyl)-furan-2-yl)-7-fluoro-quinazolin-4-yl)-amine;

List 131
(4-(3-Fluorobenzyloxy)-3-chlorophenyl)-(6-(2-((2-propane-sulphonyl-ethoxy)methyl)-thiazol-4-yl)-7-fluoro-quinazolin-4-yl)-amine;
(4-(3-Fluorobenzyloxy)-3-bromophenyl)-(6-(2-((2-propanesulphonyl-ethoxy)methyl)-thiazol-4-yl)-7-fluoro-quinazolin-4-yl)-amine;
(4-(3-Fluorobenzyloxy)-3-chlorophenyl)-(6-(2-((2-propane-sulphonyl-ethoxy)ethyl)-thiazol-4-yl)-7-fluoro-quinazolin-4-yl)-amine;
(4-(3-Fluorobenzyloxy)-3-bromophenyl)-(6-(2-((2-propanesulphonyl-ethoxy)ethyl)-thiazol-4-yl)-7-fluoro-quinazolin-4-yl)-amine;
(4-(3-Fluorobenzyloxy)-3-chlorophenyl)-(6-(2-((2-propane-sulphonyl-ethoxy)propyl)-thiazol-4-yl)-7-fluoro-quinazolin-4-yl)-amine;
(4-(3-Fluorobenzyloxy)-3-bromophenyl)-(6-(2-((2-propanesulphonyl-ethoxy)propyl)-thiazol-4-yl)-7-fluoro-quinazolin-4-yl)-amine;

List 132
(4-(3-Fluorobenzyloxy)-3-chlorophenyl)-(6-(2-((2-iso-propyl-sulphonyl-ethoxy)methyl)-thiazol-4-yl)-7-fluoro-quinazolin-4-yl)-amine;
(4-(3-Fluorobenzyloxy)-3-bromophenyl)-(6-(2-((2-iso-propyl-sulphonyl-ethoxy)methyl)-thiazol-4-yl)-7-fluoro-quinazolin-4-yl)-amine;
(4-(3-Fluorobenzyloxy)-3-chlorophenyl)-(6-(2-((2-iso-propyl-sulphonyl-ethoxy)ethyl)-thiazol-4-yl)-7-fluoro-quinazolin-4-yl)-amine;
(4-(3-Fluorobenzyloxy)-3-bromophenyl)-(6-(2-((2-iso-propyl-sulphonyl-ethoxy)ethyl)-thiazol-4-yl)-7-fluoro-quinazolin-4-yl)-amine;
(4-(3-Fluorobenzyloxy)-3-chlorophenyl)-(6-(2-((2-iso-propyl-sulphonyl-ethoxy)propyl)-thiazol-4-yl)-7-fluoro-quinazolin-4-yl)-amine;
(4-(3-Fluorobenzyloxy)-3-bromophenyl)-(6-(2-((2-iso-propyl-sulphonyl-ethoxy)propyl)-thiazol-4-yl)-7-fluoro-quinazolin-4-yl)-amine;

List 133
(4-(3-Fluorobenzyloxy)-3-bromophenyl)-(6-(2-((2-methanesulphonyl-ethylamino)-ethyl)-furan-2-yl)-quinazolin-4-yl)-amine;
(4-(3-Fluorobenzyloxy)-3-chlorophenyl)-(6-(2-((2-methanesulphonyl-ethylamino)-propyl)-furan-2-yl)-quinazolin-4-yl)-amine;
(4-(3-Fluorobenzyloxy)-3-bromophenyl)-(6-(2-((2-methanesulphonyl-ethylamino)-propyl)-furan-2-yl)-quinazolin-4-yl)-amine;

List 134
(4-(3-Fluorobenzyloxy)-3-bromophenyl)-(6-(2-((2-methanesulphonyl-ethylamino)ethyl)-thiazol-4-yl)-quinazolin-4-yl)-amine;
(4-(3-Fluorobenzyloxy)-3-chlorophenyl)-(6-(2-((2-methanesulphonyl-ethylamino)propyl)-thiazol-4-yl)-quinazolin-4-yl)-amine;
(4-(3-Fluorobenzyloxy)-3-bromophenyl)-(6-(2-((2-methanesulphonyl-ethylamino)propyl)-thiazol-4-yl)-quinazolin-4-yl)-amine;

and salts or solvates thereof, particularly pharmaceutically acceptable salts or solvates thereof; and physiologically functional derivatives thereof.

Certain compounds of formula (I) may exist in stereoisomeric forms (e.g. they may contain one or more asymmetric carbon atoms or may exhibit cis-trans isomerism). The individual stereoisomers (enantiomers and diastereoisomers) and mixtures of these are included within the scope of the present invention. Likewise, it is understood that compounds of formula (I) may exist in tautomeric forms other than that shown in the formula and these are also included within the scope of the present invention.

The compounds of the present invention may have the ability to crystallize in more than one form, a characteristic known as polymorphism, and all such polymorphic forms ("polymorphs") are encompassed within the scope of the present invention. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

As indicated above, the present invention also extends to physiologically functional derivatives of formula (I) as defined above. The term "physiologically functional derivative" as used herein refers to any pharmaceutically acceptable derivative of a compound of the present invention, for example, an ester, which upon administration to a mammal, such as a human, is capable of providing (directly or indirectly) such a compound or an active metabolite thereof. Such derivatives are clear to those skilled in the art, without undue experimentation, and with reference to the teaching of Burger's Medicinal Chemistry And Drug Discovery, 5th Edition, Vol 1: Principles And Practice, which is incorporated herein by reference.

Salts of the compounds of the present invention may comprise acid addition salts derived from a nitrogen in the compound of formula (I). The therapeutic activity resides in the moiety derived from the compound of the invention as defined herein and the identity of the other component is of less importance, although for therapeutic and prophylactic purposes it is, preferably, pharmaceutically acceptable to the patient. Salts encompassed within the term "pharmaceutically acceptable salts" refer to non-toxic salts which are generally prepared by reacting the free base with a suitable organic or inorganic acid. Representative salts include the following salts: Acetate, Aluminum, Benzenesulfonate, Benzoate, Bicarbonate, Bisulfate, Bitartrate, Borate, Bromide, Calcium, Calcium Edetate, Camsylate, Carbonate, Chloride, Chloroprocaine, Choline, Clavulanate, Citrate, Dibenzylethylenediamine, Diethanolamine, Dihydrochloride, Edetate, Edisylate, Estolate, Esylate, Ethylenediamine, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lithium, Lactobionate, Laurate, Malate, Maleate, Magnesium, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Procaine, Salicylate, Sodium, Stearate, Subacetate, Succinate, Sulfate, Tannate, Tartrate, Teoclate, Tosylate, Triethanolamine, Triethiodide, Trimethylammonium and Valerate.

Salts which are not pharmaceutically acceptable may be useful in the preparation of intermediates towards the final synthesis of compounds of formula (I) and these form a further aspect of the present invention.

According to a further aspect of the present invention there is provided a process for the preparation of a compound of formula (I) as defined above which comprises the steps:
(a) the reaction of a compound of formula (II)

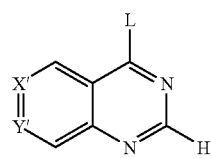
(II)

wherein;
X' is CL' and Y' is N;
or X' is N and Y' is CL';
or X' is CL' and Y' is CR$^2$;
or X' is CR$^2$ and Y' is CL';

wherein R$^2$ is as defined above, and L and L' are suitable leaving groups, with a compound of formula (III)

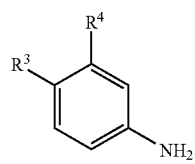
(III)

wherein R$^3$ and R$^4$ are as defined above, to prepare a compound of formula (IV)

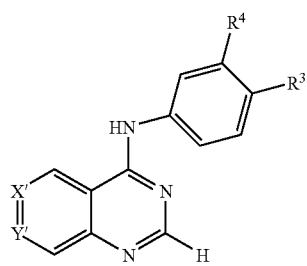
(IV)

and subsequently (b) reaction with appropriate reagent(s) to substitute the group R$^1$ by replacement of the leaving group L'; and, if desired, (c) subsequently converting the compound of formula (I) thereby obtained into another compound of formula (I) by means of appropriate reagents.

Alternatively, the compound of formula (II) as defined above is reacted with the appropriate reagents to substitute the group R$^1$ by replacement of the leaving group L' and then the product thereby obtained (of formula (V) below) is reacted with the compound of formula (III) as defined above, followed, if desired, by conversion of the compound of formula (I) thereby obtained into another compound of formula (I).

In a variant of this alternative the compound of formula (V)

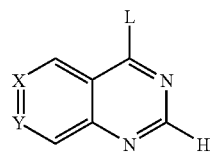
(V)

wherein X, Y, and L are as defined above, may be prepared by the reaction of a compound of formula (VI)

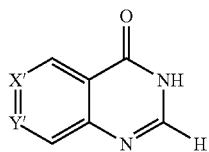
(VI)

wherein Y' and X' are as defined above, with appropriate reagents to substitute the group R$^1$ for the leaving group L' to prepare a compound of formula (VII)

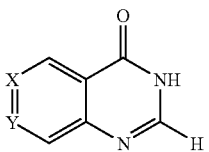
(VII)

and subsequent reaction to incorporate the leaving group L. For example, a chloro leaving group can be incorporated by reaction of a corresponding 3,4-dihydropyrimidone with carbon tetrachloride/triphenylphosphine in an appropriate solvent or with thionyl chloride with catalytic DMF in an appropriate solvent.

The group R$^1$ may, therefore, be substituted onto the basic ring system by replacement of a suitable leaving group. This may, for example, be carried out by reaction of the corresponding aryl or heteroaryl stannane or boronic acid derivative with the corresponding compound of formula (IV) carrying the leaving group L' in the appropriate position on the ring.

According to a further aspect of the present invention there is provided a process for the preparation of a compound of formula (I) as defined above which comprises the steps:
(a) reacting a compound of formula (IV) as defined above with appropriate reagent(s) to prepare a compound of formula (VIII)

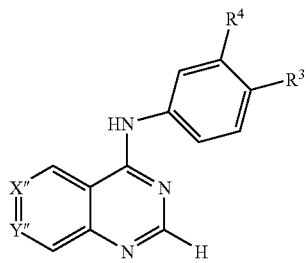

(VIII)

Where $R^3$ and $R^4$ are as defined above;

X" is CT and Y" is N;

or X" is N and Y" is CT;

or X" is CT and Y" is $CR^2$;

or X" is $CR^2$ and Y" is CT; wherein $R^2$ is as defined above and T is an appropriately functionalised group;

and (b) subsequently converting the group T into the group $R^1$ by means of appropriate reagent(s); and, if desired, (c) subsequently converting the compound of formula (I) thereby obtained into another compound of formula (I) by means of appropriate reagents.

Such processes are particularly suitable for the preparation of compounds of formula (I) wherein $R^1$ is as defined above. In such cases preferably the group T would represent a group Ar as defined above carrying a formyl group (CHO).

Where T represents a group Ar carrying a formyl group the compound (of formula (VIIIa)) may be suitably prepared from the corresponding dioxolanyl substituted compound (of formula (VIIIb)), for example by acid hydrolysis. The dioxolanyl substituted compound may be prepared by reaction of a compound of formula (IV) with an appropriate reagent to substitute the relevant leaving group with the substituent carrying the dioxolanyl ring. This reagent could, for example, be an appropriate heteroaryl stannane derivative. Alternatively, where T represents a group Ar carrying a formyl group the compound (of formula VIIIa) may be prepared from the suitably substituted heteroaryl boronic acid.

Therefore a suitable process may comprise reaction of a compound of formula (VIIIa) in which T is a group Ar carrying a formyl substituent (i.e. a —CHO group) with a compound of formula (IX): $R^5$—$SO_2$—$CH_2CH_2$-Z. The reaction preferably involves a reductive amination by means of an appropriate reducing agent, for example sodium triacetoxyborohydride or sodium borohydride in an appropriate solvent such as dichloroethane or dimethoxyethane. A representative example is shown in Scheme I. U represents a phenyl ring substituted with $R^3$ and $R^4$, wherein $R^3$ and $R^4$ are as described above.

Scheme I

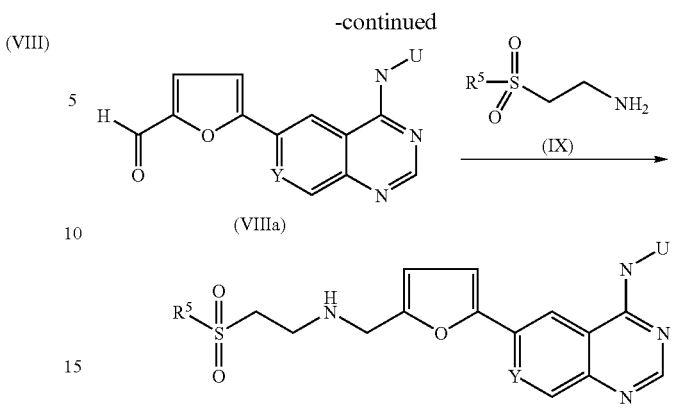

-continued

Alternatively, another suitable process may comprise oxidation of a compound of formula (VIIIb) in which T is a group Ar carrying a substituent of formula (X) ($R^5$S—$CH_2CH_2NH_2CH_2$—). Suitable methods for the oxidation to the desired compound of formula (I) will be well known to the person skilled in the art but include, for example, reaction with an organic peroxide, such as peracetic acid or metachloroperbenzoic acid, or reaction with an inorganic oxidising agent, such as OXONE®. The compound of formula (VIIIb) in which T is a group Ar carrying a substituent of formula (X) may be prepared by an analogous reaction to that described above, namely reaction of a compound of formula (VIIIa) in which T is a group Ar carrying a formyl substituent (i.e. a —CHO group) with a compound of formula (XI) ($R^5$—$SO_2$—$CH_2CH_2NH_2$) respectively.

A suitable process for generating compounds where T represents a group Ar carrying a group of the formula $R^5SO_2$—$CH_2CH_2$-Z-$(CH_2)_p$— where p=3 may comprise a Wittig reaction utilizing a phosphorus ylide, for example triethyl phosphono acetate in the presence of base such as potassium carbonate in a suitable solvent such as acetonitrile with a compound of formula VIIIa to provide a compound of formula VIIIc as depicted in Scheme II. (for reviews of the Wittig reaction: A. Mercker, *Org. Reactions* 14, 270, 1965; I. Gosney and A. G. Rowley, in *Organophosphorus Reagents in Organic Synthesis*, J. I. G. Cadogan (ed.), Academic Press, London, 1979, pp 17-153). A compound of formula (VIIId) could be suitably prepared from a compound of formula (VIIIc) via several methods. For example, where R=ethyl in formula (VIIIc), treatment of a compound of formula (VIIIc) with aqueous base such as aqueous sodium hydroxide would provide a compound of formula (VIIIc) with R=H which could then be converted to a compound of formula (VIIId) utilizing standard amide bond forming reactions, such as treatment with a compound of formula (IX) in the presence of CDI (carbonyldiimidazole) in a suitable solvent such as DMF. Suitable methods for the reduction to the desired compounds of formula (I) will be well known to one skilled in the art, but include, for example, reaction with a borane reducing agent such as borane dimethylsulfide. Further, one skilled in the art could also see the application of this process to a compound of formula (I), wherein Z is oxygen. For example, in the conversion of a compound of formula (VIIIc) to a compound of formula (VIIId), the coupling reaction could be performed using the appropriately substituted ethanol of formula (IX) ($R^5$—$SO_2$—$CH_2CH_2$—OH) and the subsequent reduction could afford the desired compound of formula (I) (where Z=O) utilizing a variety of reduction conditions. By way of example, one such set of reduction conditions may include utilizing lithium aluminum hydride in the presence of a lewis acid such as boron trifluoride etherate.

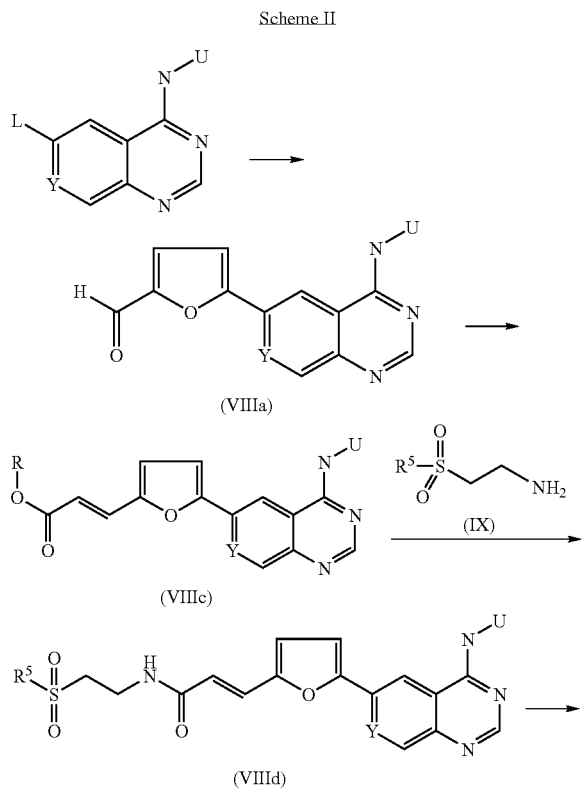

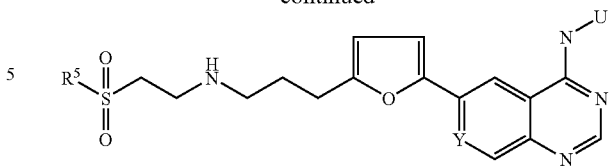

An alternate process includes the transformation of a compound of formula (VIIIc) to a compound of formula (VIIIe) as in Scheme III utilizing a variety of reducing agents such as borane dimethylsulfide or lithium aluminum hydride. From this alcohol intermediate, one skilled in the art can envisage a multitude of pathways to synthesize the desired compound of formula (I). Two representative synthetic routes are depicted in Scheme III as A and B. An esterification or coupling reaction can be carried out on the compound of formula VIIIe with an appropriately substituted carboxylate of formula (XII): $R^5$—$SO_2$—$CH_2CO_2H$. A compound of formula (VIIIf) may be treated with a reducing agent such as lithium borohydride in a suitable solvent such as THF or a compound of formula VIIIf may be converted to an intermediate thioester which may be subsequently reduced (Baxter, S. L., Bradshaw, J. S. *J Org. Chem.* 1981, 46(4), 831-2) to afford the desired compound of formula I wherein Z=O. Following pathway B of Scheme III, a compound of formula (VIIIe) may be converted to a compound of formula (VIIIg) through a variety of methods well known to one skilled in the art, but include, for example treatment with triphenylphosphine in carbon tetrachloride (L=Cl) or treatment with toluenesulfonyl chloride in the presence of base (L=TsO). The conversion of a compound of formula (VIIIg) to the desired compound of formula I may be done utilizing a compound of formula (IX) in the presence of base such as potassium carbonate.

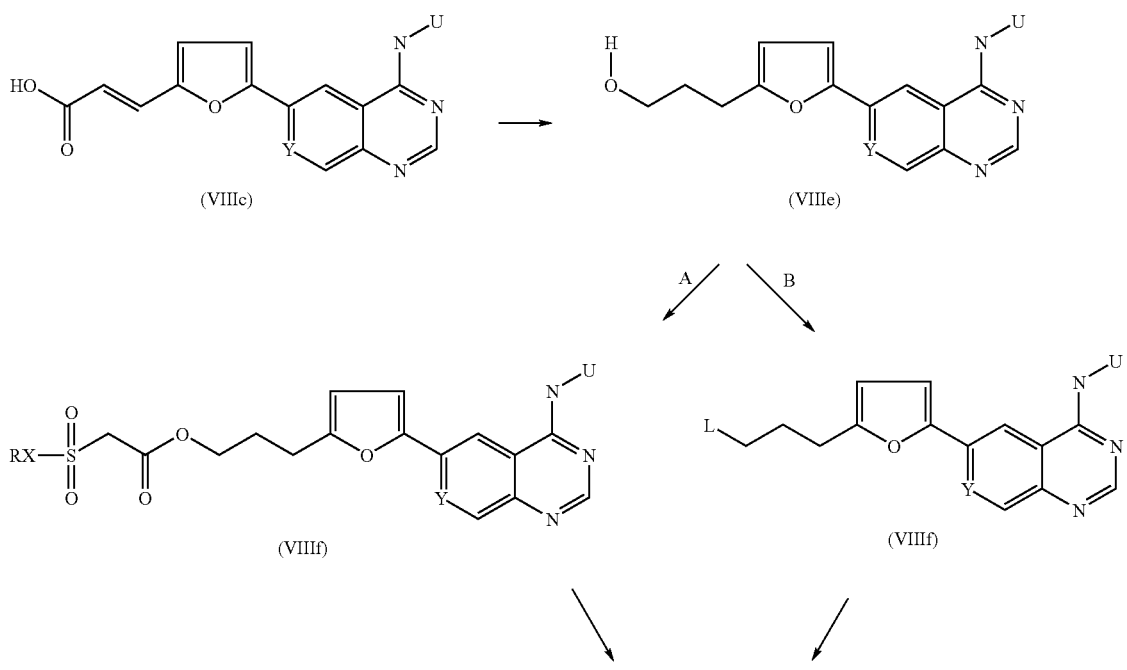

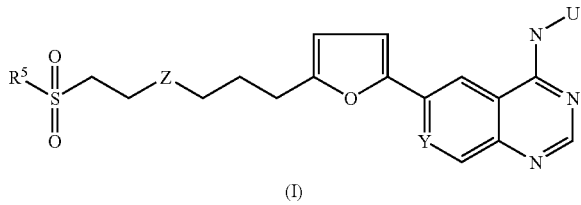

(I)

A similar synthetic route, depicted in Scheme IV, may be utilized to obtain compounds of the present invention wherein I represents a group Ar carrying a group of the formula $R^5SO_2CH_2CH_2$-Z-$(CH_2)_p$— where p=1. The formyl in the compound of formula (VIIIa) may be reduced to the hydroxymethyl group in the compound of formula (VIIIh). From this alcohol intermediate, one skilled in the art may envisage a multitude of pathways to synthesize the desired compound of formula (I). Two representative synthetic routes are depicted in Scheme IV as A and B. An esterification or coupling reaction can be carried out on the compound of formula VIIIh with an appropriately substituted carboxylate of formula (XII). A compound of formula (VIIIi) may be treated with a reducing agent such as borane dimethyl sulfide or lithium borohydride in a suitable solvent such as THF to afford the desired compound of formula (I)

treatment with strong base, for example sodium hydride, in the presence of the appropriately substitutued vinyl sulfone, for example ethyl vinyl sulfone, in a suitable solvent such as DMF. Alternatively, pathway B of Scheme IV may be done with the appropriate leaving group on the compound of formula (XII) ($R^5SO_2CH_2CH_2$-L) in the presence of base, for example sodium hydride or potassium carbonate.

Alternatively, another suitable process may involve the appropriate use of $R^5S$—$CH_2CH_2$-Z or $R^5$—S—$CH_2CO_2H$ in routes similar to those depicted in (III) and (IV) with the employment of an oxidation step to convert the variously substituted sulfides to sulfones. Suitable methods for the oxidation to the desired compound of formula (I) will be well known to the person skilled in the art but include, for example, reaction with an organic peroxide, such as peracetic acid or metachloroperbenzoic acid, or reaction with an inorganic oxidising agent, such as OXONE®.

Scheme IV

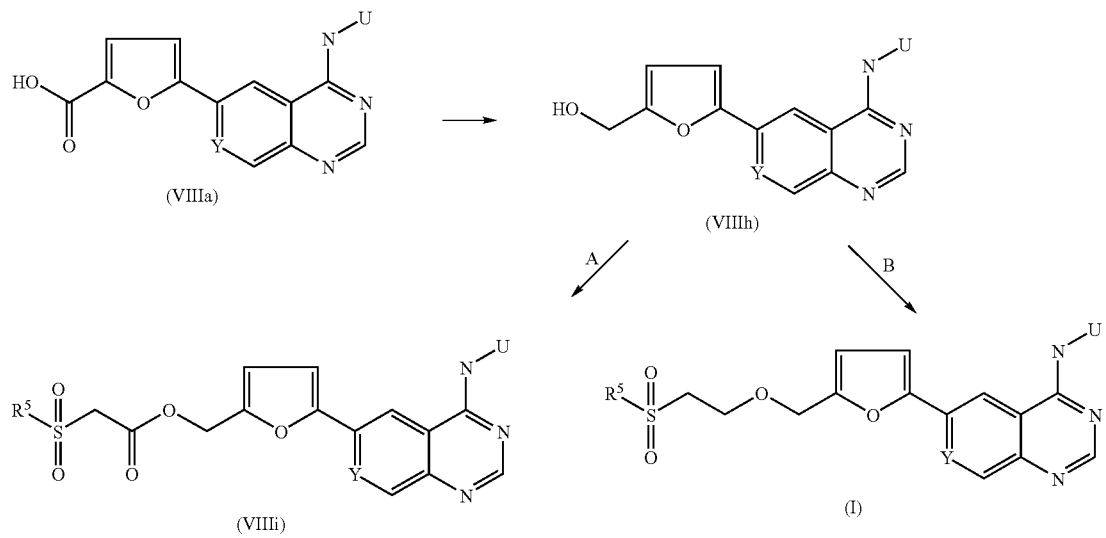

wherein Z=O. Following pathway B of Scheme IV, a compound of formula (VIIIh) may be converted directly to a desired compound of formula (I) through a variety of methods known to one skilled in the art. For example, a compound of formula (VIIIh) may be treated with a compound of formula (IX) when Z=OH in the presence of $ZnCl_2$ (reference: *Journal of Organic Chemistry*, 52, 3917, 1987) or under modified Mitsunobu conditions (reference: *Tetrahedran*, 50(18), 5469, 1994) such as utilizing triphenylphosphine, diethyldiazodicarboxylate in a suitable solvent such as THF with a suitable base present such as triethylamine. Alternatively, pathway B of Scheme IV may be done by Alternatively, another suitable process, depicted in Scheme V, may be utilized to obtain compounds of the present invention wherein T represents a group Ar carrying a group of the formula $R^5SO_2CH_2CH_2$-Z-$(CH_2)_p$— where p=2. The formyl group in the compound of formula (VIIIa) may be converted to the nitro vinyl derivative formula (VIIIj) utilizing nitromethane under basic conditions such as potassium carbonate in a suitable solvent such as methanol or utilizing nitromethane with ammonium acetate (Hamdan, A., Wasley, J. W. *Syn Communication* 1985, 15(1), 71-4). A compound of formula (VIIIj) may be treated under a multitude of reducing conditions to afford a compound of formula (VIIIk) well known to one skilled in the art, but may include, for example treatment of a compound of formula (VIIIj) with lithium aluminum hydride or treatment with zinc in the presence of hydrogen chloride or Raney nickel under an atmosphere of hydrogen. A compound of formula (VIIIk) may be coupled to an appropriately substituted compound of formula (XII) to afford a compound of formula (VIIIL) utilizing standard conditions such as treatment with carbonyl diimidazole in DMF in the presence of a base such as diisopropylethylamine. A compound of formula (VIIIL) may be treated under the appropriate reduction conditions mentioned earlier to provide the desired compound of formula (I).

One skilled in the art may easily apply the representative synthetic routes depicted in Scheme III, Scheme IV and Scheme V to the series of compounds of formula (I) wherein the Ar is the appropriately substituted thiazole.

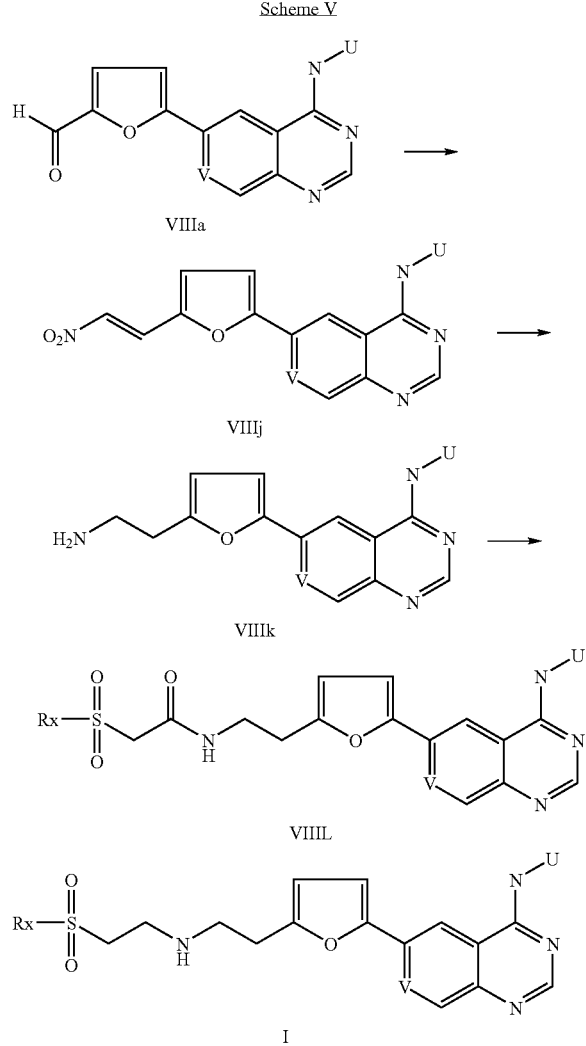

Scheme VI depicts the transformation whereby the appropriately substituted thiazole formyl compound of formula (VIIIm) may be synthesized from a heteroaryl stannane coupling of 2-formyl-4-tributyltinthiazole and a compound of formula (I) wherein L is a bromine, iodine or triflate. Alternatively, (VIIIm) may be synthesized utilizing the 2-formyl-4-thiazolylboronic acid either generated as a discrete intermediate or in situ generation via thexyl boronate reaction with 2-formyl-4-bromo-thiazole (*Angew. Chem. Int. Ed* 37, 84, 1998).

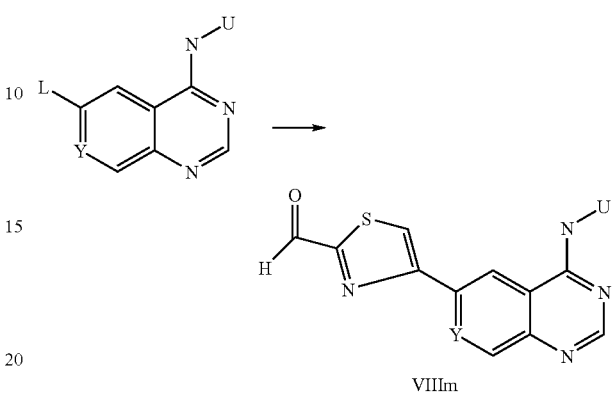

Further, another suitable process for converting a compound of formula (VIII), where X" is a relevant leaving group or Y" is a relevant leaving group, to a desired compound of formula (I) is through the representative synthetic route depicted in Scheme VII. Conversion to a compound of formula (VIIIn) may be achieved by a reaction with vinyl ether stannane, for example 1-ethoxy-1-vinyl tributyl tin in the presence of a metal catalyst such as palladium bistriphenylphosphine dichloride. A compound of formula (VIIIn) may be converted to a halomethyl ketone of formula (VIIIo) utilizing a variety of conditions known to one skilled in the art, but by way of example, include n-bromosuccinimide in a suitable sovent such as THF or bromine in acetic acid in a reaction temperature range of –10° C. to 50° C., preferably 0° C. to 22° C. One skilled in the art can envisage a number of synthetic routes to generate desired compounds of formula (I), two of which are shown in Scheme VII, depicted as Pathway A and B. In Pathway A, a compound of formula (VIIIo) may be condensed with a compound of formula (XIII) (NC—$(CH_2)_p$—C(S)—$NH_2$) where p=1-3 in a suitable solvent such as acetic acid or DMF in a temperature range from 0°-120° C., preferably a temperature range from 50°-110° C. to generate a compound of formula (VIIIp). A compound of formula (VIIIp) may be converted to a compound where T=a 2-aminoalkythiazole of formula (VIIIq) by utilizing a variety of reducing conditions which may include borane dimethylsulfide in THF or Raney Nickelin ethanol under an atmosphere of hydrogen. As described in previous synthetic routes, this aminoalkyl compound may be coupled with a suitably substituted compound of formula (XII) and the amide carbonyl may be subsequently reduced to provide the desired compound of formula (I) utilizing borane dimethylsulfide in THF, for example. An alternative pathway for the conversion of a compound of formula (VIIIo) to the desired compound of formula (I) may be obtained employing pathway B of Scheme VII. A compound of formula (VIIIo) is condensed with a compound of formula (XIII) (Scheme XI may be used to synthesize these appropriately substituted reagents) in a suitable solvent such as DMF or acetic acid in a temperature range from 0°-120° C., preferably a temperature range from 50-110° C. to generate a compound of formula (I) where $R^6$ is defined as before. A compound of formula (I) may be converted to another compound of formula (I) by the selective removal of the $R^6$ substituent. For example, where $R^6$=trifluoroacetate, a compound of formula (I) may be treated with aqueous sodium hydroxide.

such as treatment with (methoxymethyl)diphenylphosphine oxide in the presence of a base such as phenyl lithium or lithium diisopropylamide in a suitable solvent such as THF.

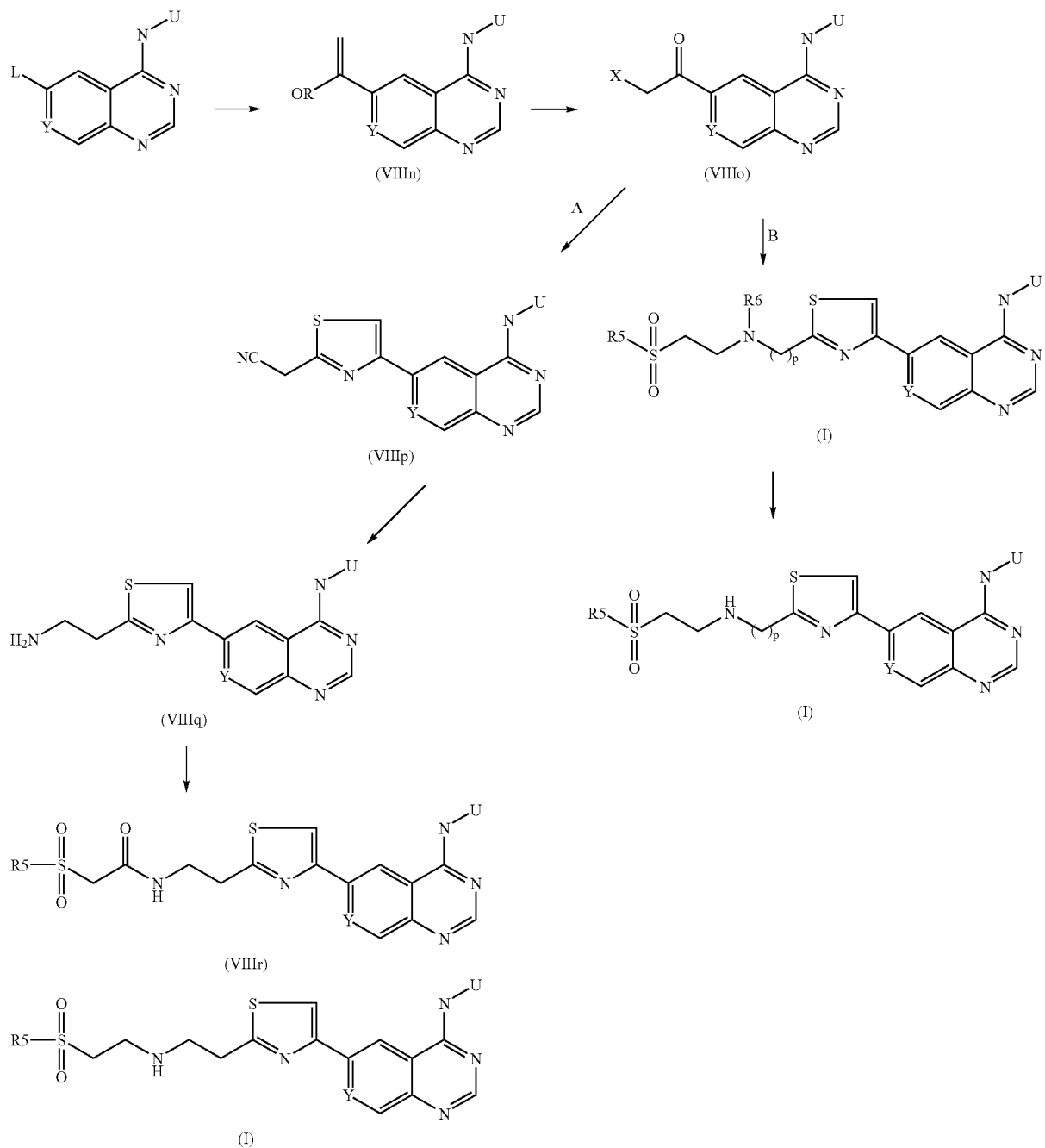

Scheme VII

Alternatively, another suitable process, depicted in Scheme VIII, may be utilized to obtain compounds of the present invention wherein T represents a group Ar carrying a group of the formula $R^5SO_2CH_2CH_2\text{-}Z\text{-}(CH_2)_p$— where p=2. The formyl group in the compound of formula (VIIIa) may be converted to the methoxyvinyl group in the compound of formula VIIIs utilizing standard Wittig conditions, The conversion of a compound of formula VIIIs to the desired compound of formula I may be done utilizing a variety of synthetic transformations. One example might be treatment of a compound of formula VIIIs with a compound of formula IX in the presence of mercuric acetate followed by a reduction of the olefin (Cannon, J. G., Lee, T. *J. Med. Chem.* 27, 386-389, 1984.) Alternatively, a compound of formula VIIIs may be hydrolyzed to an intermediate aldehyde by a variety of methods well known to one skilled in the art, but include, by way of example, treatment with HCl or trimethylsilyl iodide. The intermediate aldehyde, which may not be stable, may be treated with a compound of formula IX under reductive amination conditions such as treatment with triacetoxyborohydride or sodium borohydride to provide a compound of formula I.

Scheme VIII

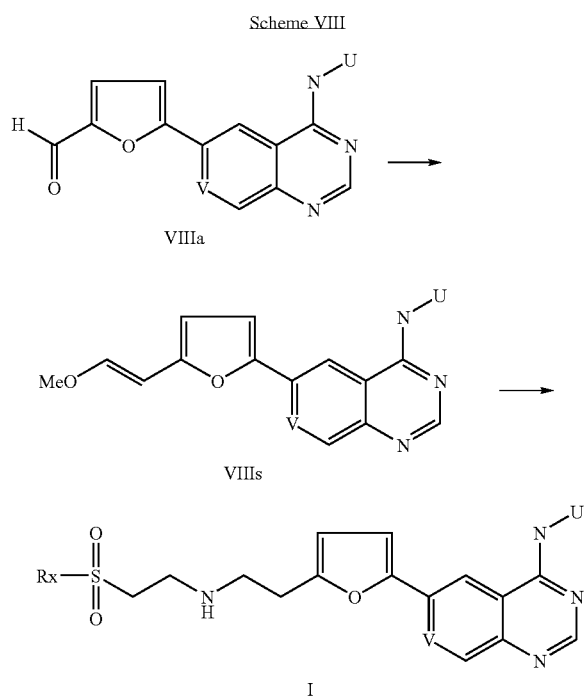

Synthesis of the appropriately substituted sulfonyl ethyl amines of formula (IX) may be achieved through numerous routes, two of which are depicted in Scheme IX and are designated Pathway A and Pathway B. Variously substituted thioethylamines may be substituted with an amino protecting group such as benzyloxycarbonyl or trifluoroacetate. Suitable protecting groups, methods for their introduction and methods for their removal would be well known to the person skilled in the art. For a description of protecting groups and their use see T. W. Greene and P. G. M. Wuts, "Protective Groups in Organic Synthesis", 2nd edn., John Wiley & Sons, New York, 1991. The sulfur may be oxidised utilizing conditions well known to those skilled in the art, but include, for example reaction with an organic peroxide, such as peracetic acid or metachloroperbenzoic acid, or reaction with an inorganic oxidizing agent, such as OXONE®. The removal of the protecting group affords the desired amine of formula IX. An alternative approach employs the appropriately substituted nitrile compound of formula (XIV). Treatment with reducing conditions such as borane dimethylsulfide in THF or Raney nickel in ethanol under an atmosphere of hydrogen may afford the desired amine compound of formula (IX).

Scheme IX

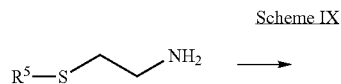

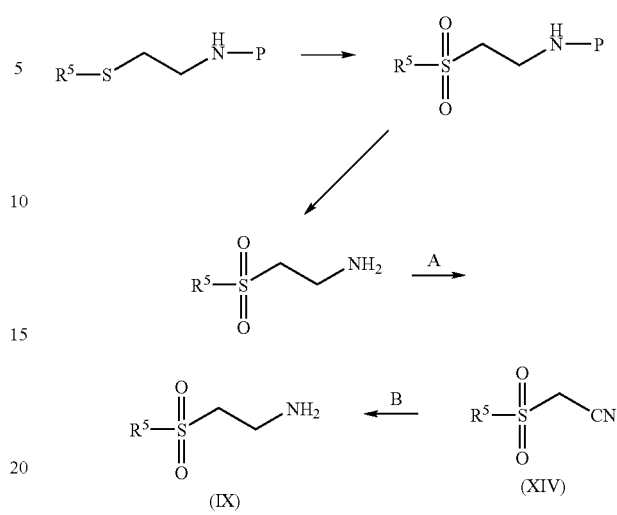

A suitable process for the synthesis of a compound of formula (XIII) which can be used in the condensation reaction to generate the appropriately substituted thiazole derivative of formula (I) is shown in Scheme X beginning with a compound of formula (IX). Under standard alkylating conditions well known to those skilled in the art a compound of formula (XV) may be synthesized, for example by treatment with 3-chloropropionitrile in the presence of a suitable base such as potassium carbonate in a suitable solvent such as DMF. Alternatively, the conversion of a compound of formula (IX) to a compound of formula (XV) may employ standard reductive amination conditions by treatment with an appropriately substituted cyanoalkylcarbaldehyde in the presence of a reducing agent such as sodium cyanoborohydride with a suitable acid present such as acetic acid. A compound of formula (XV) may be subsequently substituted using standard acylating or alkylating conditions such as treatment with trifluoroacetic anhydride in the presence of base such as potassium carbonate in a suitable solvent such as acetonitrile or DMF to afford a compound of formula (XVI). The nitrile substituent on the compound of formula (XVI) may be converted to a thioamide by using various conditions, but include, for example, treatment with hydrogen sulfide.

Scheme X

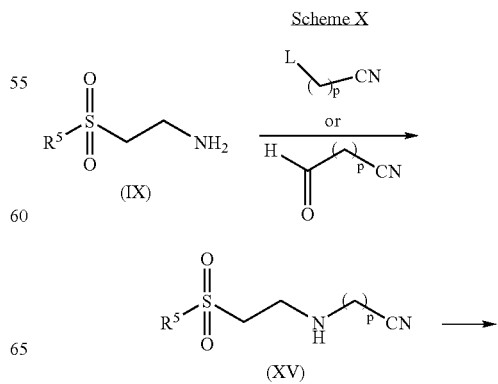

-continued

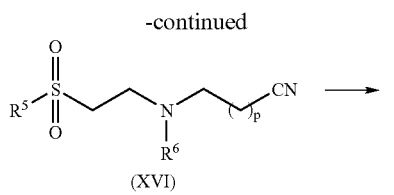
(XVI)

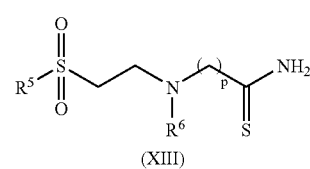
(XIII)

-continued

(XIX)

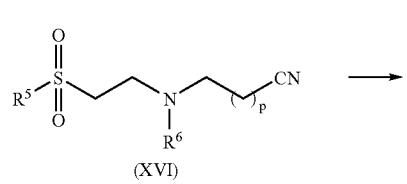
(XVI)

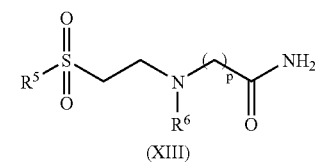
(XIII)

An alternate synthetic route that also represents a suitable process for the synthesis of a compound of formula (XIII) is shown in Scheme XI. Standard amide bond coupling conditions well known to those skilled in the art may be use to convert a compound of formula (IX) to a compound of formula by treatment with the appropriately protected hydroxy alkycarboxylate. The conversion of a compound of formula (XVII) to a compound of formula (XVIII) may be achieved through conditions mentioned earlier such as reduction with borane dimethyl sulfide in THF. The secondary amine in a compound of formula (XVIII) may be further substituted via a standard alkylation or acylation reaction such as treatment with trifluoroacetic anhydride in the presence of a base such as potassium carbonate in a suitable solvent such as acetonitrile or DMF to afford a compound of formula (XIX). The protecting group may be removed and a suitable leaving group generated such as a tosylate or mesylate using conditions well known to those skilled in the art, but include, for example treatment with tosyl chloride in the presence of a base such as triethylamine in a suitable solvent such as dichloromethane. The leaving group may be displaced using a suitable nitrile anion, such as potassium cyanide, in a suitable solvent such as DMF. A suitable process for the conversion of a compound of formula (XVI) to a compound of formula (XIII) is as described for Scheme X.

Alternatively, another suitable process, depicted in Scheme XII, may be utilized to obtain compounds of the present invention wherein T represents a group Ar carrying a group of the formula $R^5SO_2CH_2CH_2\text{-}Z\text{-}(CH_2)_p$— where p=4. A compound of formula VIIIe may be converted to a compound of formula VIIIt through a variety of methods well known to one skilled in the art. By way of example, the conversion of the hydroxyl group of a compound of formula VIIIe to a suitable leaving group may be achieved by treatment with toluenesulfonyl chloride in the presence of base such as triethylamine or sodium hydride. The leaving group in a compound of formula VIIIt may be displaced by treatment with a suitable anion such as sodium cyanide to provide a compound of formula VIIIu. Treatment of a compound of formula VIIIu with reducing conditions such as borane dimethylsulfide or Raney Nickel under an atmosphere of hydrogen may provide a compound of formula VIIIv. As shown in earlier representative synthetic routes, the amino group may be coupled to the appropriately substituted sulphonylacetic acid to afford a compound of formula VIIIw. The amide carbonyl of a compound of formula VIIIw may be reduced using a variety of conditions described earlier to provide the desired compound of formula I. One skilled in the art may easily apply the representative synthetic route depicted in Scheme XII to the series of compounds of formula (I) wherein the Ar is the appropriately substituted thiazole Scheme XI

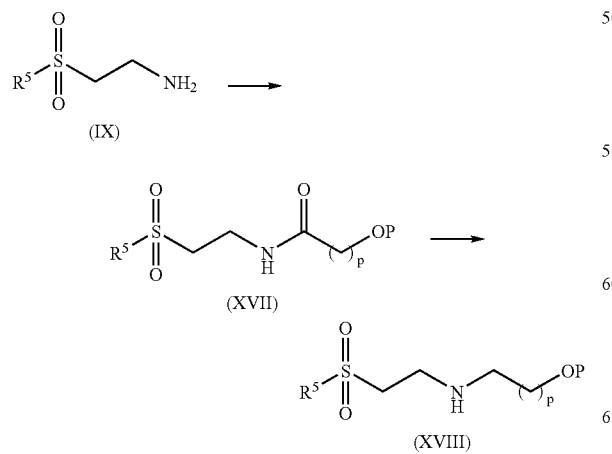

Scheme XII

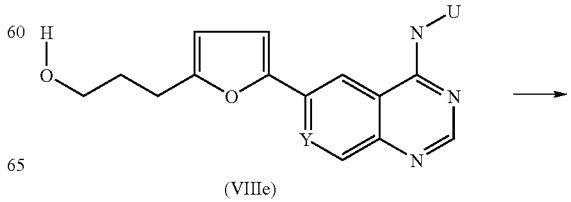
(VIIIe)

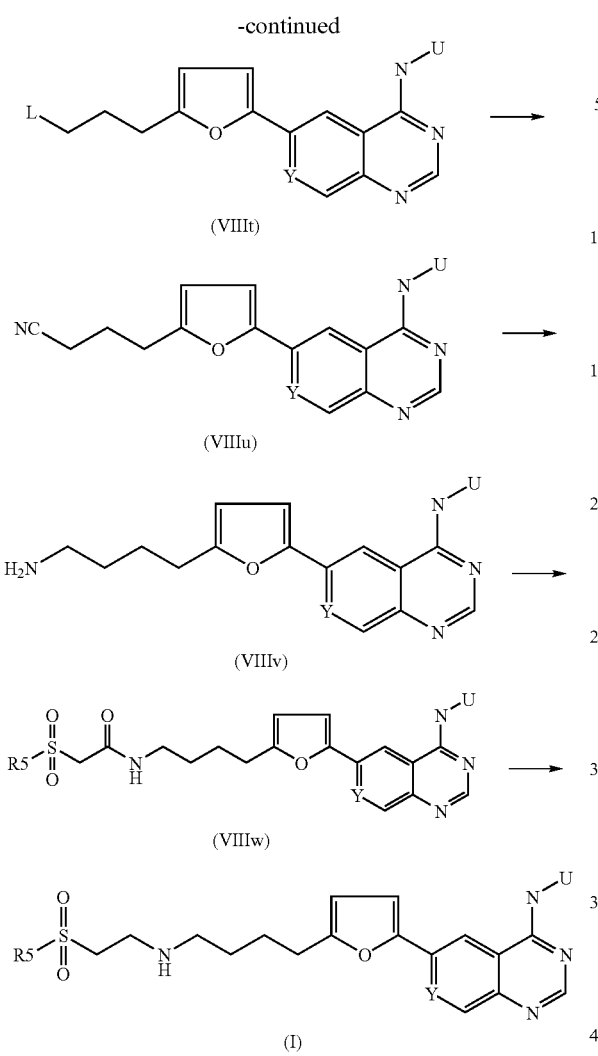

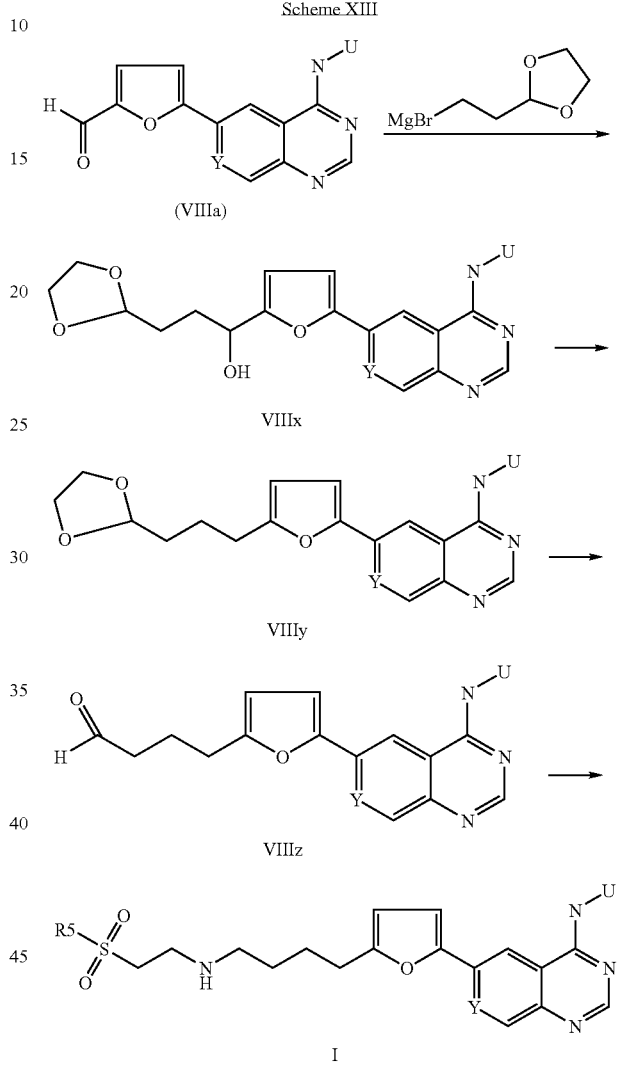

An alternate synthetic route that also represents a suitable process for the synthesis of compounds of the present invention wherein T represents a group Ar carrying a group of the formula $R^5SO_2CH_2CH_2$-Z-$(CH_2)_p$— where p=4 is depicted in Scheme XIII. A compound of formula VIIIa may be converted to a compound of formula VIIIx by treatment with the appropriate organometallic reagent, for example a Grignard reagent (for multiple methods, see *Comprehensive Organic Transformations, a Guide to Functional Group Preparations*, Richard C. Larock, VCH Publishers, Inc., New York, N.Y., 1989, pages 553-557). A deoxygenation reaction used to convert a compound of formula VIIIx to a compound of formula VIIIy would be well known to one skilled in the art (for a general review see: *Comprehensive Organic Syntheses*, Trost, B. M.; Fleming, I.; Vo8, 1991, p 811-826.), but may include for example treatment with phenylchlorothioate in the presence of DMAP followed by treatment with tributylstannyl hydride (Liu, H. J., Kulkarni, M. G. *Tetrahedron Lett.*, 26, 4847, 1985) or treatment with triethylsilane in the presence of acid such as trifluoroacetic acid (Carey, F. A., Tremper, H. S. *J. Org. Chem.* 36,758, 1971). Deprotection of the acetal group in the compound of formula VIIIy may be achieved through a hydrolysis reaction such as treatment with dilute aqueous hydrochloric acid to provide a compound of formula VIIIz. Using previously described conditions, a compound of formula VIIIz may be converted to the desired compound of formula I utilizing reductive amination conditions such as treatment with a compound of formula IX and a reducing agent such as sodium triacetoxyborohydride in the presence of a suitable acid such as acetic acid.

An alternate synthetic route that also represents a suitable process for the synthesis of compounds of the present invention wherein T represents a group Ar carrying a group of the formula $R^5SO_2CH_2CH_2$-Z-$(CH_2)_p$— where p=1, 2, 3, or 4 and Z is O is depicted in Scheme IX. A compound of formula (VIIIaa) may be generated by one skilled in the art, especially via one of the schemes outlined above. The conversion of a compound of formula (VIIIaa) to a compound of formula (I) may be achieved through a variety of methods. By way of example, the conversion of the hydroxyl group of a compound of formula (VIIIaa) to the desired ether of a compound of formula (I) may be achieved by treatment with a strong base, such as sodium hydride in the presence of a suitably substituted vinyl sulfone in an appropriate solvent such as dimethylformamide.

Scheme XIV

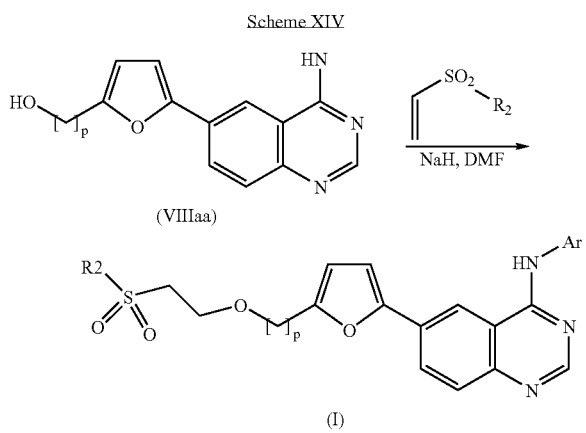

Alternatively, analogous schemes to those described above could be used wherein the substitution of the group $R^1$ onto the basic ring system occurs prior to the coupling reaction with the compound of formula (III).

In general, the group $R^2$ will be present as a substituent in the basic ring system prior to the introduction of the group $R^1$ or the group NHU.

Suitable leaving groups for L and L' will be well known to those skilled in the art and include, for example, halo such as fluoro, chloro, bromo and iodo; sulphonyloxy groups such as methanesulphonyloxy and toluene-p-sulphonyloxy; alkoxy groups; and triflate.

The coupling reaction referred to above with the compound of formula (III) is conveniently carried out in the presence of a suitable inert solvent, for example a $C_{1-4}$ alkanol, such as isopropanol, a halogenated hydrocarbon, an ether, an aromatic hydrocarbon or a dipolar aprotic solvent such as acetone, acetonitrile or DMSO at anon-extreme temperature, for example from 0 to 150° C., suitably 10 to 120° C., preferably 50 to 100° C.

Optionally, the reaction is carried out in the presence of a base. Examples of suitable bases include an organic amine such as triethylamine, or an alkaline earth metal carbonate, hydride or hydroxide, such as sodium or potassium carbonate, hydride or hydroxide.

The compound of formula (I) may be obtained from this process in the form of a salt with the acid HL, wherein L is as hereinbefore defined, or as the free base by treating the salt with a base as hereinbefore defined.

The compounds of formulae (II) and (III) as defined above, the reagents to substitute the group $R^1$, and the reagent(s) to convert the group T into the group $R^1$ are either readily available or can be readily synthesized by those skilled in the art using conventional methods of organic synthesis.

As indicated above, the compound of formula (I) prepared may be converted to another compound of formula (I) by chemical transformation of the appropriate substituent or substituents using appropriate chemical methods (see for example, J. March "Advanced Organic Chemistry", Edition III, Wiley Interscience, 1985).

For example, a compound containing an alkylthio group may be oxidised to the corresponding sulphinyl or sulphonyl compound by use of an organic peroxide (e.g. benzoyl peroxide) or suitable inorganic oxidant (eg OXONE®).

A compound containing a nitro substituent may be reduced to the corresponding amino-compound, e.g. by use of hydrogen and an appropriate catalyst (if there are no other susceptible groups), by use of Raney Nickel and hydrazine hydrate or by use of iron/acetic acid.

Amino substituents may be acylated by use of an acid chloride or an anhydride under appropriate conditions. Equally an amide group may be cleaved to the amino compound by treatment with, for example, dilute aqueous base.

All of the above-mentioned chemical transformations may also be used to convert any relevant intermediate compound to another intermediate compound prior to the final reaction to prepare a compound of formula (I); this would thus include their use to convert one compound of formula (III) to a further compound of formula (III) prior to any subsequent reaction.

Various intermediate compounds used in the above-mentioned processes, including but not limited to certain of the compounds of formulae (II) to (XIX) as illustrated above, are novel and thus represent a further aspect of the present invention.

In particular, a further aspect of the present invention is intermediate compounds of formulae (VIIIa) and (VIIIq) defined above, with the exception of the following compounds:

5-(4-(4-Benzyloxy-phenylamino)-pyrido[3,4-d]pyrimidin-6-yl)-furan-2-carbaldehyde;

5-(4-Benzyloxy-phenyl)-(6-(5-[1,3-dioxolan-2-yl]-furan-2-yl)-quinazolin-4-yl)-amine;

5-(4-(4-Benzyloxy-phenylamino)-quinazolin-6-yl)-furan-2-carbaldehyde;

In particular, a yet further aspect of the present invention is intermediate compounds of formula (VIIIc) as defined above.

with the proviso that the following compound is excluded:
(4-Benzyloxy-phenyl)-(6-(5-((2-methanesulphinyl-ethylamino)-methyl)-furan-2-yl)-pyrido[3,4-d]pyrimidin-4-yl)-amine.

The compounds of formula (I) and salts thereof, are believed to have anticancer activity as a result of inhibition of the protein tyrosine kinase c-erbB-2, c-erbB-4 and/or EGF-R enzymes and their effect on selected cell lines whose growth is dependent on c-erbB-2 or EGF-r tyrosine kinase activity.

The present invention thus also provides compounds of formula (I) and pharmaceutically acceptable salts or solvates thereof, or physiologically functional derivatives thereof, for use in medical therapy, and particularly in the treatment of disorders mediated by aberrant protein tyrosine kinase activity such as human malignancies and the other disorders mentioned above. The compounds of the present invention are especially useful for the treatment of disorders caused by aberrant c-erbB-2 and/or EGF-r activity such as breast, ovarian, gastric, pancreatic, non-small cell lung, bladder, head and neck cancers, and psoriasis.

The present invention is directed to methods of regulating, modulating, or inhibiting protein kinases of both the receptor and non-receptor types, for the prevention and/or treatment of disorders related to unregulated protein kinase activity, including cell proliferative disorders, metabolic disorders and excessive cytokine production disorders. The compounds of the present invention can also be used in the treatment of certain forms of cancer, can be used to provide additive or synergistic effects with certain existing cancer chemotherapies, and/or be used to restore effectiveness of certain existing cancer chemotherapies and radiation. At the present time, there is a need in the areas of diseases characterized by cell proliferation for such therapeutic agents. The compounds of the present invention are additionally useful in the treatment of one or more diseases afflicting mammals which are characterized by cellular proliferation in the areas of blood vessel proliferative disorders, fibrotic disorders, mesangial cell proliferative disorders and metabolic diseases. Blood vessel proliferative disorders include arthritis and restenosis. Fibrotic disorders include hepatic cirrhosis and atherosclerosis. Mesangial cell proliferative disorders include glomerulonephritis, diabetic nephropathy, malignant nephrosclerosis, thrombotic microangiopathy syndromes, organ transplant rejection and glomerulopathies. Metabolic disorders include psoriasis, diabetes mellitus, chronic wound healing, inflammation and neurodegenerative diseases.

A further aspect of the invention provides a method of treatment of a human or animal subject suffering from a disorder mediated by aberrant protein tyrosine kinase activity, including susceptible malignancies, which comprises administering to said subject an effective amount of a compound of formula (I) or a pharmaceutically acceptable salt or solvate thereof, or a physiologically functional derivative thereof.

In one aspect of the method, two or more protein kinases selected from c-erb-b2, c-erbB-4, or EGFr exhibit aberrant activity. In another aspect of the method, erbB-2 and EGFr exhibit aberrant activity.

A further aspect of the invention provides a method of treatment of a human or animal subject suffering from cancer or a malignant tumour, psoriasis, rheumatoid arthritis or bronchitis, which comprises administering to said subject an effective amount of a compound of formula (I) or a pharmaceutically acceptable salt or solvate thereof, or a physiologically functional derivative thereof.

A further aspect of the present invention provides the use of a compound of formula (I), or a pharmaceutically acceptable salt or slovate thereof, or a physiologically functional derivative thereof, in the preparation of a medicament for the treatment of a disorder mediated by aberrant protein tyrosine kinase activity. In one aspect of the use, two or more protein kinases selected from c-erb-b2, c-erbB-4, or EGFr exhibit aberrant activity. In another aspect of the use, erbB-2 and EGFr exhibit aberrant activity.

A further aspect of the present invention provides the use of a compound of formula (I), or a pharmaceutically acceptable salt or solvate thereof, or a physiologically functional derivative thereof, in the preparation of a medicament for the treatment of cancer and malignant tumours.

A further aspect of the present invention provides the use of a compound of formula (I), or a pharmaceutically acceptable salt or solvate thereof, or a physiologically functional derivative thereof, in the preparation of a medicament for the treatment of psoriasis.

A further aspect of the present invention provides the use of a compound of formula (I), or a pharmaceutically acceptable salt or solvate thereof, or a physiologically functional derivative thereof, in the preparation of a medicament for the treatment of rheumatoid arthritis.

A further aspect of the present invention provides the use of a compound of formula (I), or a pharmaceutically acceptable salt or solvate thereof, or a physiologically functional derivative thereof, in the preparation of a medicament for the treatment of bronchitis.

Whilst it is possible for the compounds of the present invention to be administered as the new chemical, it is preferred to present them in the form of a pharmaceutical formulation.

According to a further feature of the present invention there is provided a pharmaceutical formulation comprising at least one compound of formula (I), or a pharmaceutically acceptable salt or solvate thereof, or a physiologically functional derivative thereof, together with one or more pharmaceutically acceptable carriers, diluents or excipients.

Pharmaceutical formulations may be presented in unit dose forms containing a predetermined amount of active ingredient per unit dose. Such a unit may contain for example 0.5 mg to 1 g, preferably 70 mg to 700 mg, more preferably 5 mg to 100 mg of a compound of the formula (I) depending on the condition being treated, the route of administration and the age, weight and condition of the patient.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may include other agents conventional in the art having regard to the type of formulation in question, for example those suitable for oral administration may include flavouring agents.

The animal requiring treatment with a compound of the present invention is usually a mammal, such as a human being.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of the present invention and their salts and solvates, and physiologically functional derivatives thereof, may be employed alone or in combination with other therapeutic agents for the treatment of the above-mentioned conditions. In particular, in anti-cancer therapy, combination with other chemotherapeutic, hormonal or antibody agents is envisaged. Combination therapies according to the present invention thus comprise the administration of at least one compound of formula (I) or a pharmaceutically acceptable salt or solvate thereof, or a physiologically functional derivative thereof, and at least one other pharmaceutically active agent. The compound(s) of formula (I) and the other pharmaceutically active agent(s) may be administered together or separately and, when administered separately this may occur simultaneously or sequentially in any order.

The amounts of the compound(s) of formula (I) and the other pharmaceutically active agent(s) and the relative timings of administration will be selected in order to achieve the desired combined therapeutic effect.

Certain embodiments of the present invention will now be illustrated by way of example only. The physical data given for the compounds exemplified is consistent with the assigned structure of those compounds.

$^1$H NMR spectra were obtained at 500 MHz on a Bruker AMX500 spectrophotometer, on a Bruker spectrophotometer at 300 Mz, or on a Bruker AC250 or Bruker AM250 spectrophotometer at 250 MHz. J values are given in Hz. Mass spectra were obtained on one of the following machines: VG Micromass Platform (electrospray positive or negative), HP5989A Engine (thermospray positive) or Finnigan-MAT LCQ (ion trap) mass spectrometer or GC-MS MD 1000 Mass Spectrometer. Analytical thin layer chromatography (tlc) was used to verify the purity of some intermediates which could not be isolated or which were too unstable for full characterisation, and to follow the progess of reactions. Unless otherwise stated, this was done using silica gel (Merck Silica Gel 60 F254). Unless otherwise stated, column chromatography for the purification of some compounds used Merck Silica gel 60 (Art. 1.09385, 230-400 mesh), and the stated solvent system under pressure.

Petrol refers to petroleum ether, either the fraction boiling at 40-60° C., or at 60-80° C.

Ether refers to diethylether.

DMSO refers to dimethylsulphoxide.

THF refers to tetrahydrofuran.

DMF refers to dimethylformamide

HPLC refers to high pressure liquid chromatography.

Useful preparative techniques are described in WO96/09294, WO97/03069, WO97/13771, WO95/19774, WO96/40142 and WO97/30034; also described in these publications are appropriate intermediate compounds other than those detailed below.

Preparation processes specified in the prior art or in the experimental details below for compounds with a particular basic ring system (1) to (3) above may be suitably adapted for others of these basic ring systems.

General Procedures (A) Reaction of an Amine with a Bicyclic Species Containing a 4-chloropyrimidine or 4-chloropyridine Ring The optionally substituted bicyclic species and the specified amine were mixed in an appropriate solvent (typically acetonitrile unless otherwise specified, although ethanol, 2-propanol or DMSO may also be used), and heated to reflux. When the reaction was complete (as judged by tlc), the reaction mixture was allowed to cool. The resulting suspension was diluted, e.g. with acetone, and the solid collected by filtration, washing e.g. with excess acetone, and dried at 60° C. in vacuo, giving the product as the hydrochloride salt. If the free base was required (e.g. for further reaction), this was obtained by treatment with a base e.g. triethylamine; purification by chromatography was then performed if required.

(B-1) Reaction of a Product from Procedure (A) with a Heteroaryl Tin Reagent

A stirred mixture of the product from Procedure (A), (containing a suitable leaving group such as chloro, bromo, iodo or triflate), a heteroaryl stannane and a suitable palladium catalyst, such as bis(triphenylphosphine)palladium (II) chloride or 1,4-bis(diphenylphosphino)butane palladium (II) chloride (prepared as described in C. E. Housecroft et. al., Inorg. Chem., (1991), 30(1), 125-130), together with other appropriate additives, were heated at reflux in dry dioxane or another suitable solvent under nitrogen until the reaction was complete. The resulting mixture was generally purified by chromatography on silica.

(B-2) Reaction of a Product from Procedure (A) with a Heteroaryl Boronic Acid Reagent A stirred mixture of the product from Procedure (A), (containing a suitable leaving group such as chloro, bromo, iodo or triflate), a heteroaryl boronic acid and a suitable palladium catalyst, such as Palladium Acetate together with other appropriate additives such as triphenyl phosphine and triethylamine, were heated at reflux in dry dioxane or another suitable solvent under nitrogen until the reaction was complete. The resulting mixture was generally purified by chromatography on silica.

(C) Removal of a 1,3-dioxolan-2-yl Protecting Group to Liberate an Aldehyde

The compound containing the 1,3-dioxolan-2-yl group was suspended in an appropriate solvent, e.g. THF and treated with hydrochloric acid, either as an aqueous solution (e.g. 2N) or as a solution in dioxane (e.g. 4 molar) and stirred at ambient temperature until the reaction was judged complete (e.g. by tlc or LC/MS analysis). Generally the mixture was diluted with water, and the resulting precipitate was collected by filtration, washed with water and dried to give the aldehyde.

(D) Reaction of an Aldehyde with an Amine by Reductive Amination

An aldehyde (such as the product of General Procedure C) and the required primary or secondary amine were stirred together in a suitable solvent (such as dichloromethane) containing glacial acetic acid (4A molecular sieves may also be present) for ca. 1 h. A suitable reducing agent, such as sodium (triacetoxy) borohydride was then added and stirring continued under nitrogen until the reaction was complete (as judged by hplc or tlc). The resulting mixture was washed with an aqueous basic solution (e.g. sodium or potassium carbonate) and extracted with a suitable solvent, e.g. dichloromethane. The dried organic phase was evaporated and the residue purified either by column chromatography or by Bond Elut™ cartridge. If desired, the isolated material was then converted into the hydrochloride salt e.g. by treatment with ethereal hydrogen chloride.

(E) Reaction Sequence to Prepare Appropriately Substituted Thioamides

E-1 Reaction of an Aminosulfide with Chloroacetonitrile

To a stirred mixture of an aminosulfide and a suitable base such as sodium bicarbonate or sodium carbonate in an appropriate solvent (typically acetonitrile, although DMF or dioxane can be used) was added chloroacetonitrile dropwise. The resulting mixture was heated to reflux until the reaction was complete. The solid was filtered and the filtrate was concentrated to provide the corresponding aminonitrile.

E-2 Trifluoroacetamide Protection of an Aminonitrile

A solution of the aminonitrile (such as the product of general procedure A) and an amine base, such as triethylamine or NMM in a suitable solvent (e.g. dichloromethane), was cooled to 0° C. and trifluoroacetic anhydride was added dropwise. The resulting mixture was stirred at room temperature until the reaction was complete. Water was added and the mixture was extracted with a suitable solvent (e.g. dichloromethane), the organic layer was dried over anhydrous magnesium sulfate and concentrated. The crude product was purified by column chromatography to provide the corresponding trifluoroacetamide.

E-3 Oxidation of a Cyanosulfide

To a stirred solution of a sulfide (such as the product of general procedure E1) in a suitable solvent (typically methanol/water (2:1), although dichloromethane can be used) cooled to 0° C. was added an oxidizing agent (typically oxone, although MCPBA can be used). The resulting mixture was stirred at room temperature until the reaction was complete. The reaction was concentrated to remove any organic solvents, diluted with water, and extracted with an appropriate solvent (e.g. dichloromethane). The organic layer was dried and concentrated to provide the corresponding cyanosulfone.

E-4 Preparation of Thioamides

To a solution of a cyanosulfone (such as the product of general procedure E-3) and an organic base (e.g. triethylamine) in THF was added hydrogen sulfide gas. The resulting mixture was stirred at room temperature until the reaction was complete. The mixture was concentrated and triturated with hexane to provide thioamide.

(F) Reaction Sequence to Prepare an Optionally Substituted Thiazole

F-1 Reaction of a Vinylstannane with a Product from Procedure (A)

A stirred mixture of the optionally substituted bicyclic 4-anilinopyrimidine species, tributyl(1-ethoxyvinyl)stannane (1 to 5 molar equivalents), and a suitable palladium catalyst (0.03 to 0.1 molar equivalents), such as bis(triphenylphosphine) palladium (II) chloride or tetrakis(triphenylphosphine) palladium (0) was heated at reflux in an appropriate solvent (typically acetonitrile, although DMF or dioxane can be used) until the reaction was complete. The resulting mixture was concentrated and generally purified by trituration with diethyl ether to provide the corresponding bicyclic pyrimidine vinyl ether.

F-2 Reaction of a Product from Procedure (F-1) with a Bromination Reagent

A bicyclic pyrimidine vinyl ether (such as the product of general procedure F-1) and one equivalent of a bromination reagent, such as N-bromosuccinimide or bromine, were stirred at 0° C. in a suitable solvent (typically 10% aqueous THF or dichloromethane) until the reaction was complete. The resulting mixture was dried over anhydrous magnesium sulfate and concentrated, or in the case of bromine the solid was filtered, to provide the corresponding α-bromoketone.

F-3 Reaction of a Product from Procedure (F-2) with a Product from Procedure (E-4)

A stirred mixture of an α-bromoketone (such as the product of general procedure F-2) and thioamide from Procedure E-4 in a 1:1 molar ratio was heated to 70-100° C. in an appropriate solvent (typically DMF, although acetonitrile and THF can be used) until the reaction was complete. The resulting mixture was washed with an aqueous basic solution (e.g. sodium carbonate) and extracted with a suitable solvent, e.g. ethyl acetate. The dried organic layer was concentrated and the residue was purified by column chromatography to provide the corresponding trifluoroacetamide aminothiazole.

F-4 Removal of a Trifluoroacetamide Protecting Group to Liberate an Aminothiazole A mixture of a trifluoroacetamide protected aminothiazole (such as the product of general procedure F-3) in 2M NaOH/methanol (1:1) was stirred at room temperature until the reaction was complete. The mixture was concentrated, poured into water and extracted with an appropriate solvent e.g. 10% MeOH/dichloromethane. The dried organic layer was concentrated, then dissolved in ethyl acetate/MeOH (1:1) and treated with 4M HCl/dioxane. The resulting solid was filtered to provide the corresponding amine hydrochloride salt.

(G) Reaction of an Aldehyde with a Phosphorylide

An aldehyde (such as the product from General Procedure B-2 and General Procedure C) and the required phosponoacetate (such as triethylphosphonoacetate) were stirred together in a suitable solvent (such as acetonitrile) in the presence of excess base, for example three equivalents of potassium carbonate. The stirring was continued for 3-20 h. When the reaction was judged complete using TLC the reaction was diluted with an organic solvent such as ethyl acetate and water. The layers were separated and the volatiles were removed from the organic layer. The residue was triturated in an organic solvent such as methylene chloride and the solids that persisted were collected by filtration. The purity of the material was typically acceptable.

(H) Hydrolysis of an Ester

An ester such as the product of General Procedure G was dissolved in a suitable solvent such a methanol and treated with excess aqueous sodium hydroxide (such as a 2 M NaOH solution) in a temperature range of room temperature to 100° C., preferrable 60°-85° C. The desired product is isolated by acidifying with aqueous hydrochloric acid and extraction into an organic solvent such as ethyl acetate. A precipitate formed in the biphasic system and was collected by filtration. Generally, the solids were dried to provide the carboxylic acid.

(I) Reaction of a Carboxylic Acid and an Amine Through a Coupling Procedure

An acid, such as that afforded from General Procedure (H) was dissolved in a suitable solvent such as DMF and a coupling reagent was added, for example 1,1'-carbonyldiimidazole. The amine was added and the reaction was stirred at room temperature for 3-36 h. Upon completion as judged by TLC, an extractive work-up was done. Desired amide was either precipitated from an organic solvent in acceptable purity or the material was purified using column chromatography.

(J) Reduction of the Amide (Including an Alpha, Beta Unsaturated Amide) to an Alkyl Amine An amide, such as that afforded from General Procedure (I) was dissolved and warmed to a temperature between 50°-900° C. in a suitable solvent such as THF. A solution of reducing agent, for example a 2M solution of borane dimethylsulfide in THF or lithium borohydride, was added dropwise and the reaction was continued under heating until all starting material was consumed as judged by TLC. The reaction was quenched under typical acidic conditions and purified using column chromatography techniques.

(K) Reduction of a Nitrile to an Amine

An alkylsulphonylacetonitrile such as isopropylsulphonylacetonitrile or propanesulphonylacetonitrile was heated in THF in a temperature range of 50°-80° C. with dropwise addition of a reducing agent such as borane dimethylsulfide, for example a 2M solution of borane dimethylsulfide in THF. When the reaction was completed as judged by TLC, a solution of HCl in methanol was added dropwise (gas evolution occurred). The volatiles were removed. The desired product was free-based by treatment with base such as saturated potassium carbonate and extraction into dichloromethane. The desired amine was purified using column chromatography.

(L) Reaction of an Aldehyde with Nitromethane to Form a Nitrovinyl Group

An aromatic aldehyde such as that formed from General Procedure (B-2) or General Procedure C, nitromethane and ammonium acetate were combined and heated to 85° C. for 15 min. The reaction mixture was cooled to rt and concentrated under reduced pressure. The residue was dissolved in an organic solvent such as ethyl acetate and washed with aq. sat'd $NaHCO_3$ solution before removing volatiles in vacuo. Purification by column chromatography afforded desired product.

(M) Reduction of Nitro-vinyl Group to form Amino-ethyl Group

To a solution of lithium tetrahydride-aluminate (1.0 M in THF) in anhydrous THF was added dropwise a solution of a vinyl-nitro compound such as that generated from General Procedure (L) in THF at 0° C. under nitrogen. The ice bath was removed and the mixture was heated to 50° C. for 18 h. The reaction was then cooled to rt and water was added cautiously followed by 15% NaOH solution and water again. The aqueous layer was extracted with ethyl acetate. The desired product was isolated through standard methods in acceptable purity or can be purified through column chromatography.

(N) Reduction of an Aldehyde to an Alcohol

An aromatic aldehyde such as that formed from General Procedure (B-2) or General Procedure C, was dissolved in $CH_2Cl_2$ in the presence of catalytical amount of acetic acid. To the solution was added reducing reagents such as sodium cyanoboron hydride, and the resulting mixture was stirred at rt for 3 h. The reaction was then quenched with sat'd aqueous sodium bicarbonate. The aqueous layer was extracted with methylene chloride and the combined organics were washed with water and brine and dried over anhydrous magnesium sulfate. Filtration through Celite-silica gel and concentration in vacuo provided desired product in acceptable purity.

(O) Michael Addition of an Alcohol to an Vinyl Sulfone

To a solution of an alcohol that formed from General Procedure (N) in anhydrous DMF was added a catalytical amount of appropriate bases such as NaH, NaOH, KOBu$^t$ etc. After 10 min, to the resulting anion solution was introduced a solution of an appropriate vinyl sulfone in DMF and the mixture was stirred at rt for 2 days. Then the reaction was diluted with EtOAc and water and the aqueous layer was extracted with EtOAc. The combined organic layers were washed with water and brine and filtered through Celite. The concentrated residue was purified by column (silica gel, 60% EtOAc/hexanes) to yield desired product.

(P) N-Alkylation of the Side Chain

A quinazoline product from General Procedure (D), an appropriate halide, diisopropyl ethyl amine were combined in anhydrous DMF and the mixture was heated to 70° C. for 5 to 48 h. The reaction was then quenched with water and EtOAc. After extraction of the aqueous layer, the organic was concentrated in vacuo and the residue was dissolved in minimal amount of EtOAc. Tritration from $Et_2O$ or hexanes gave pure product.

Synthesis of Intermediates

N-5-[N-tert-Butoxycarbonyl)amino]-2-chloropyridine

A stirred solution of 6-chloronicotinic acid (47.3 g), diphenylphosphoryl azide (89.6 g) and triethylamine (46 ml) in t-butanol (240 ml) were heated under reflux under nitrogen for 2.5 hours. The solution was cooled and concentrated in vacuo. The syrupy residue was poured into 3 liters of a rapidly stirred solution of 0.33N aqueous sodium carbonate. The precipitate was stirred for one hour and filtered. The solid was washed with water and dried in vacuo at 70° C. to give the title compound (62 g) as a pale brown solid; m.p. 144-146° C.; 67H [$^2$H$_6$]-DMSO 8.25(1H,d), 7.95 (1H, bd), 7.25 (1H, d), 6.65(1H, bs), 1.51 (9H,s); m/z (M+1)$^+$ 229.

This material may subsequently be carried forward to the appropriately substituted pyridopyrimidine intermediate according to the procedures as described in WO95/19774, J. Med. Chem., 1996, 39, pp 1823-1835, and J. Chem. Soc., Perkin Trans. 1, 1996, pp 2221-2226. Specific compounds made by such procedures include 6-chloro-pyrido[3,4-d]pyrimidin-4-one and 4,6-dichloro-pyrido[3,4-d]pyrimidine.

4-Chloro-6-bromoquinazoline and 4-Chloro-6-iodoquinazoline were prepared as described in WO 96/09294.

4-Benzyloxyaniline is commercially available as the hydrochloride salt; this is treated with aqueous sodium carbonate solution, and the mixture extracted with ethyl acetate; the organic solution is dried (MgSO$_4$) and concentrated to give the free base as a brown solid, used without further purification.

Other substituted anilines were in general prepared by analogous methods to those outlined in WO 96/09294 and/or as follows:

Step 1: Preparation of the Precursor Nitro-compounds

4-Nitrophenol (or an appropriate substituted analogue, such as 3-chloro-4-nitrophenol) was treated with a base such as potassium carbonate or sodium hydroxide in an appropriate solvent, such as acetone or acetonitrile. The appropriate aryl or heteroaryl halide was added and the reaction mixture heated or stirred at room temperature overnight.

Purification A: Most of the acetonitrile was removed in vacuo, and the residue was partitioned between water and dichloromethane. The aqueous layer was extracted with further dichloromethane (×2), and the combined dichloromethane layers were concentrated in vacuo.

Purification B: removal of insoluble material by filtration, followed by concentration of the reaction mixture in vacuo, and chromatography on silica.

Step 2: Reduction to the Corresponding Aniline

The precursor nitro compound was reduced by catalytic hydrogenation at atmospheric pressure using 5% Pt/carbon, in a suitable solvent (eg ethanol, THF, or mixtures thereof to promote solubility). When reduction was complete, the mixture was filtered through Harborlite™, washing with excess solvent, and the resulting solution concentrated in vacuo to give the desired aniline. In some cases, the anilines were acidified with HCl (e.g. in a solution in dioxane) to give the corresponding hydrochloride salt.

Anilines prepared by such methods include:
4-(3-Fluorobenzyloxy)aniline; m/z (M+1)$^+$ 218
3-Chloro-4-(3-fluorobenzyloxy)aniline; m/z (M+1)$^+$ 252
4-Benzyloxy-3-chloroaniline; m/z (M+1)$^+$ 234 and, in appropriate cases, their hydrochloride salts.

2-Bromo-4-nitrophenol

2-Bromo-4-nitroanisole (20 g, 0.086 mol) was dissolved in DMF (414 mL) at rt under N$_2$. Sodium ethylthiolate (17.4 g, 0.207 mol) was added and the reaction mixture was warmed to 115° C. for 2 h. The reaction was cooled to rt and diluted with EtOAc (200 mL) and 1 M HCl (aq., 200 mL). The phases were separated, and the desired product was extracted into 1 M NaOH (aq, 150 mL×3). The basic aqueous extracts were combined and acidified using conc. HCl. The desired product was extracted from the acidic aqueous solution using EtOAc (250 mL×2). The combined organic layers were washed with brine and dried over sodium sulfate. The volatiles were removed in vacuo to afford a light brown semi-solid (9.8 g, 52% yield). $^1$H NMR (DMSO-d6) δ 8.33 (m, 1H); 8.09 (m, 1H); 7.07 (d, 1 H).

2-Bromo-1-(3-fluorobenzyloxy)-4-nitrobenzene

2-Bromo-4-nitrophenol (4.86 g, 0.0223 mol), triphenylphosphine (7.6 g, 0.0290 mol), 3-fluorobenzylalcohol (3.65 g, 0.0290 mol) were combined and dissolved in THF (89 mL). The reaction temperature was cooled to 0° C. and DIAD (4.50 g, 0.0290 mol) was added. The reaction was allowed to warm slowly to rt and stirred for 3 h before it was diluted with water (100 mL) and EtOAc (100 mL). The layers were separated and the aqueous layer was extracted with EtOAc (200 mL×2). The organic extracts were combined and washed with brine, followed by drying over sodium sulfate. The volatiles were removed in vacuo and the residual semi-solid was treated with diethyl ether. The solids were removed by filtration. The volatiles from the resulting filtrate were removed in vacuo and the material was purified using EtOAc:Hexanes (90/10) in a biotage LC system to afford the title compound as a yellow solid (3.73 g, 68% yield). $^1$H NMR (DMSO-d6) □ 8.43 (d, 1H); 8.26 (m, 1H); 7.45 (m, 1H); 7.38 (d, 1H); 7.30 (m, 2H); 7.17 (m, 1H) 5.39 (s, 2H).

2-Bromo-1-(benzyloxy)-4-nitrobenzene

Synthesized in an analogous manner to that described for 2-bromo-1-(3-fluorobenzyloxy)-4-nitrobenzene utilizing benzylalcohol in place of 3-fluorobenzylalcohol. 1H NMR (DMSO) 8.45 (m, 1H); 8.27 (m, 1H); 7.51-7.33 (m, 6H); 5.37 (s, 2H).

3-Bromo-4-(3-fluorobenzyloxy)-aniline

Under a blanket of N$_2$, Pt/C (5%, 0.37 g) was charged to a Parr Shaker Flask. Ethanol (150 mL) and 2-bromo-1-(3-fluorobenzyloxy)-4-nitrobenzene (3.73 g, 0.011 mol) were added and the reaction mixture was placed on a Parr Shaker Apparatus under 30 psi of H$_2$ for 5 h. The reaction was filtered through a pad of Celite to remove the catalyst and the volatiles were removed from the filtrate. The residue was dissolved in the CH$_2$Cl$_2$ (5 mL) and treated with conc. HCl (1 mL). The precipitate was collected by filtration and free-based using saturated aqueous sodium bicarbonate (2.27 g, 67% yield) $^1$H NMR (DMSO-d6) δ 7.4 (m, 1H); 7.23 (m, 2H); 7.11 (m, 1H); 6.86 (d, 1H); 6.77 (m, 1H); 6.48 (m, 1H); 5.0 (s, 2H); 4.93 (bs, 2H).

3-Bromo-4-(benzyloxy)-aniline

Synthesized in an analogous manner to that described for 3-Bromo-4-(3-fluorobenzyloxy)-aniline. $^1$H NMR (DMSO) 7.56 (s, 1H); 7.47-7.43 (m, 2H); 7.39 (m, 2H); 7.35-7.24 (m, 3H); 5.21 (s, 2H).

Iso-Propylsulfonylethylamine

Prepared according to Procedure K. 2-iso-Propylsulfonylacetonitrile (0.50 g, 3.39 mmol) was dissolved in THF and warmed to reflux under $N_2$. Borane dimethylsulfide (2M, 1.7 mL, 3.39 mmol) was added dropwise and the reaction was stirred for an additional 40 minutes at reflux. After cooling the reaction to rt, HCl (2 M in MeOH) was added to the reaction slowly due to gas evolution. The volatiles were removed and fresh methanol was added to the resulting residue. Again, the volatiles were removed and the resulting residue was taken up in $CH_2Cl_2$ (25 mL) and washed with saturated potassium carbonate (aqueous). The organic layer was dried over sodium sulfate and the volatiles were removed to afford the title compound. GC-MS m/z 152 (MH+).

n-Propane-sulfonylethylamine hydrochloride

Prepared according to Procedure K from propanesulfonylacetonitrile (1 eq.) and borane dimethylsulfide (1 eq.) in THF. 8.30 (bs, 2H); 3.44 (m, 3H); 3.20 (m, 3H); 1.69 (m, 2H); 0.99 (m, 3H). GC-MS m/z 152 (MH+).

6-Iodo-(4-(3-fluorobenzyloxy)-3-bromophenyl)-quinazolin-4-yl)amine

Prepared according to Procedure A from 3-bromo-4-(3-fluorobenzyloxy)-aniline (0.79 g, 2.7 mmol) and 4-chloro-6-iodo-quinazoline (0.8 g, 2.7 mmol). $^1$H NMR (DMSO-d6) δ 11.1 (bs, 1H); 9.10 (s, 1H); 8.87 (s, 1H); 8.29 (d, 1H); 8.03 (s, 1H); 7.68 (m, 1H); 7.62 (d, 1H); 7.45 (m, 1H); 7.33-7.26 (m, 3H); 7.16 (m, 1H); 5.28 (s, 2H).

6-Iodo-(4-benzyloxy)-3-bromophenyl)-quinazolin-4-yl)amine

Prepared according to Procedure A from 3-bromo-4-(benzyloxy)-aniline (1 eq.) and 4-chloro-6-iodo-quinazoline (1 eq.) in acetonitrile. Electrospray MS m/z 532 (MH+).

(4-Benzyloxyphenyl)-(6-iodo-7-fluoro-quinazolin-4-yl)-amine hydrochloride

Prepared according to Procedure A from 4-chloro-6-iodo-7-fluoro-quinazoline hydrochloride (4.02 grams, 11.65 mmoles), anhydrous dioxane (70 ml), dichloromethane (20 ml), and 4-benzyloxyaniline hydrochloride (2.83 grams, 12 mmoles). The mixture was stirred and heated to 110° C. (oil bath temperature) for 16 hours, cooled to room temperature and filtered to remove the precipitated solids. The solids were washed with cold anhydrous dioxane (100 ml) followed by cold anhydrous diethyl ether. The yellowish solid was collected and dried under vacuum at room temperature to yield 4.68 grams (79%) of the title compound. δH NMR (400 MHz, DMSO-d$_6$): 11.2(s, 1H), 9.3(d, 1H), 8.79(s, 1H), 7.64(d, 1H), 7.58(d, 2H), 7.44(d, 2H), 7.38(m, 2H), 7.31(m, 1H), 7.09(d, 2H), 5.14(s, 2H) ESI-MS m/z 472(M+1).

7-Iodoquinazolin-4-one

7-Amino-quinazolin-4-one (R. Dempsy and E. Skito, Biochemistry, 30, 1991, 8480) (1.61 g) was suspended in 6N HCl (20 ml) and cooled in an ice bath. A solution of sodium nitrite (0.75 g) in water (10 ml) was added dropwise over 15 minutes. After a further 10 minutes, a solution of potassium iodide (1.66 g) in water (5 ml) was added dropwise. The mixture was warmed to 20° C. and after 3 hours partitioned between ethyl acetate and sodium thiosulphate. The organic phase was dried and concentrated in vacuo to give the title compound (0.485 g); m/z (M+1+) 271.

4-Chloro-7-iodoquinazoline

7-Iodoquinazolin-4-one (0.46 g) was treated with phosphorous oxychloride (5 ml) at reflux under nitrogen for 2 hours. The mixture was cooled, evaporated and partitioned between saturated aqueous sodium carbonate and ethyl acetate. The organic phase was dried and concentrated in vacuo to give the title compound (0.43 g); m/z (M+1+) 291.

2-Amino-4-fluoro-5-iodo-benzoic acid

To a vigorously stirred solution of dichloromethane (700 ml), methanol (320 ml), and 2-amino-4-fluoro-benzoic acid (33.35 grams, 215 mmoles) was added solid sodium hydrogencarbonate (110 grams, 1.31 moles) followed by portion addition of benzyltrimethyl ammonium dichloroiodate (82.5 grams, 237 mmoles). The mixture was allowed to stir for 48 hours. The mixture was filtered to remove the insolubles. The remaining solid residue was washed with 200 ml of dichloromethane. The filtrate was concentrated and redissolve in a one to one mixture of ethyl acetate (1 liter) and a 0.2 N solution of sodium hydroxide (1 liter), added to a 2 liter separatory funnel and extracted. The organic layer was washed with an additional 200 ml of water. The aqueous layers were combined and acidified with 2N hydrochloric acid. The resulting precipitate was collected by suction filtration, washed with water and dried under vacuum at 60° C. to yield 46.5 grams (77%) of the title compound. $^1$H NMR (400 MHz, DMSO-d$_6$) δ: 8.04(d, 1H), 7.1(s, broad, 2H), 6.63(d, 1H). ESI-MS m/z 280 (M−1).

4-Fluoro-5-iodo-isatoic anhydride

Anhydrous dioxane (0.5 liters), 2-amino-4-fluoro-5-iodo-benzoic acid (46 grams, 164 mmoles), and trichloromethylchloroformate (97.4 grams, 492 mmoles) were added to a one liter one neck flask equipped with a magnetic stir bar and reflux condenser. The solution was placed under anhydrous nitrogen, stirred and heated to reflux for 16 hours. The reaction mixture was allowed to cool and was poured into one liter of hexanes. The solid was collected by suction filtration, washed with an additional 0.5 liters of hexanes, and dried under vacuum at room temperature to yield 45.5 grams (90%) of the title compound. $^1$H NMR (400 MHz, DMSO-d$_6$) δ: 11.86(s, 1H), 8.24(d, 1H), 6.84(d, 1H). ESI-MS m/z 308 (M+1).

4-Hydroxy-6-iodo-7-fluoroquinazoline

Dimethylformamide (0.5 liters), 4-fluoro-5-iodo-isatoic anhydride (45 grams, 147 mmoles), and formamidine acetate (45.92 grams, 441 mmoles), were combined in a one liter one-neck flask fitted with a magnetic stir bar. The mixture was placed under anhydrous nitrogen and heated at 110° C. for 6 hours. The mixture was allowed to cool, followed by concentrating the reaction mixture to one third its original volume on the rotary evaporator. The resulting mixture was poured onto 3 liters of ice water. The resulting precipitated solid was collected by suction filtration. The solid was washed with an additional one liter of distilled water. The resulting solid was dried under vacuum at 70° C. to yield 38.9 grams (91%) of the title compound. $^1$H NMR (400 MHz, DMSO-$d_6$) δ: 12.43(s, 1H), 8.46(d, 1H), 8.12(s, 1H), 7.49(d, 1H). ESI-MS m/z 291 (M+1).

4-Chloro-6-iodo-7-fluoro-quinazoline hydrochloride

Thionyl chloride (0.6 liters), 4-hydroxy-6-iodo-7-fluoro-quinazoline (36 grams, 124 mmoles), and dimethylformamide (6 ml) were combined in a one liter one-neck flask fitted with a magnetic stir bar. The mixture was placed under anhydrous nitrogen and heated to a gentle reflux for 24 hours. The mixture was allowed to cool, followed by concentrating the reaction mixture to a thick yellowish residue. To this residue was added dichloromethane (0.1 liter) and toluene (0.1 liter). The mixture was concentrated to dryness. This procedure was repeated two additional times. To the resulting solid was added 0.5 liters of dry dichloromethane and the mixture was stirred for one hour. The mixture was filtered and the remaining solids were washed with minimal dichloromethane. The dichoromethane filtrates were combined, concentrated to a solid, and dried under vacuum at room temperature to yield 28.6 grams (67%) of the title compound. $^1$H NMR (400 MHz, CDCl$_3$-$d_1$) δ: 9.03(s, 1H), 8.76(d, 1H), 7.69(d, 1H). ESI-MS m/z 309(M+1).

2-Bromo-4-(1,3-dioxolan-2-yl) thiazole

2-Bromothiazole-4-carbaldehyde (6.56 g, 34.17 mmol) [A. T. Ung, S. G. Pyne/Tetrahedron: Asymmetry 9 (1998) 1395-1407] and ethylene glycol (5.72 ml, 102.5 mmol) were heated under reflux in toluene (50 ml), with a Dean and Stark trap fitted, for 18 hr. The product was concentrated and purified by column chromatography (15% ethyl acetate/hexane) to give the product as a yellow solid (6.03 g); m/z 236,238.

4-(1,3-Dioxolan-2-yl)-5-(tributylstannyl)thiazole

2-Bromo-4-(1,3-dioxolan-2-yl) thiazole (6.4 g, 27.14 mmol) was stirred at −78° C. in dry THF (38 ml).1.6M n butyl lithium in hexane (18.6 ml, 29.78 mmol) was added dropwise under nitrogen. After 30 min at this temperature, tributyl tin chloride (7.35 ml, 27.14 mmol) was added dropwise. The reaction was allowed to warm to 0° and water (20 ml) was added. The product was extracted into ether (3×100 ml). The combined organic extracts were dried (MgSO$_4$) and evaporated. The residue was triturated with isohexane (3×100 ml) and the mother liquors were decanted, combined and concentrated to give a brown oil (11.88 g); m/z 444-450.

2-(Phenylsulfonyl)-ethylamine hydrochloride

Prepared according to General Procedure (K) utilizing phenylsulfonylacetonitrile (5 g, 0.027 moles) and borane dimethyl sulfide (2M, 18 mL). $^1$H NMR (DMSO) 7.94 (m, 2H); 7.80 (m, 1H); 7.71 (m, 2H); 3.65 (m, 2H); 3.33 (s, 2H); 3.00 (m, 2H).

N-Methyl-2-(aminoethylsulfonyl)-imidazole hydrochloride

Prepared according to General Procedure K utilizing $^1$H NMR (DMSO-d6) 7.64 (s, 1H); 7.22 (s, 1H); 3.84 (s, 3H); 3.82 (m, 2H); 3.17 (m, 2H).

2-(Aminoethylsulfonyl)-pyridine

Prepared according to $^1$H NMR (DMSO-d6) 8.75 (d, 1H); 8.12 (m, 1H); 7.99 (d, 1H); 7.71 (m, 1H); 3.44 (m, 2H); 2.76 (m, 2H).
GC-MS 187.

(4-Benzyloxyphenyl)-(6-bromoquinazolin-4-yl)-amine hydrochloride

4-Chloro-6-bromoquinazoline (0.25 g, 1.0 mmol) and 4-benzyloxyaniline (0.25 g, 1.3 mmol) were mixed in 2-propanol (6 ml) and heated at reflux for 10 mins (Procedure A). The solution was allowed to cool at room temperature and the 2-propanol removed in vacuo. The resulting solid was triturated with acetone to give the product as a yellow solid (0.39 g, 88%); δH [$^2$H$_6$]-DMSO 11.60 (1H, b, NH), 9.21 (1H, s, 5-H), 8.86 (1H, s, 2-H), 8.20 (1H, d, 7-H), 7.90 (1H, d, 8-H), 7.65 (2H, d, 2'-H, 6'-H), 7.50-7.25 (5H, m, Ph-H), 7.10 (2H, d, 3'-H, 5'-H), 5.15 (2H, s, CH$_2$); m/z 405/407 (M+).

(4-Benzyloxyphenyl)-(6-iodoquinazolin-4-yl)-amine hydrochloride

4-Chloro-6-iodoquinazoline (8 g) was treated with 4-benzyloxyaniline (5.5 g) in acetonitrile (500 ml) at reflux under N$_2$ for 18 hours. Subsequent cooling and filtration gave the title compound (13.13 g); δH [$^2$H$_6$]-DMSO 11.45 (1H, b, NH), 9.22 (1H, s, 5-H), 8.89 (1H, s, 2-H), 8.36 (1H, d, 7-H), 7.69 (1H, d, 8-H) 7.63 (2H, d, 2'-H, 6'-H), 7.52-7.29 (5H, m, Ph-H), 7.14 (2H, d, 3'-H, 5'-H), 5.18 (2H, s, CH$_2$); m/z (M+1)$^+$ 454.

(4-Benzyloxyphenyl)-(6-iodo-7-fluoro-quinazolin-4-yl)-amine hydrochloride

Prepared according to Procedure A from 4-chloro-6-iodo-7-fluoro-quinazoline hydrochloride (4.02 grams, 11.65 mmoles), anhydrous dioxane (70 ml), dichloromethane (20 ml) and 4-benzyloxyaniline hydrochloride (2.83 grams, 12 mmoles). The mixture was stirred and heated to 110° C. (oil bath temperature) for 16 hours. The mixture was cooled to room temperature and filtered to remove the precipitated solids. The solids were washed with cold anhydrous dioxane (100 ml) followed by cold anhydrous diethyl ether. The yellowish solid was collected and dried under vacuum at room temperature to yield 4.68 grams (79%) of the title compound. δH (400 MHz, DMSO-d$_6$): 11.2(s, 1H), 9.3(d, 1H), 8.79(s, 1H), 7.64(d, 1H), 7.58(d, 2H), 7.44(d, 2H), 7.38(m, 2H), 7.31 (m,1H), 7.09(d, 2H), 5.14(s, 2H) ESI-MS m/z 472(M+1).

6-Iodo-(4-(3-fluorobenzyloxy)-3-chlorophenyl)-quinazolin-4yl)amine

Prepared according to Procedure A from (4-(3-fluorobenzyloxy)-3-chlorophenyl)amine (1 eq) and 4-chloro-6-iodo-quinazoline (1 eq) in iso-propyl alcohol. $^1$H NMR (DMSO-d6) 9.83 (s, 1H); 8.92 (s, 1H); 8.58 (s, 1H); 8.09 (d, 1H); 8.00 (d, 1H); 7.61 (d, 1H); 7.52 (d, 1H); 7.44 (m, 1H); 7.20-7.33 (m, 3H); 7.15 (m, 1H); 5.21 (s, 2H); MS m/z 506 (M+1).

6-Iodo-(4-(3-fluorobenzyloxy)-phenyl)-quinazolin-4-yl)amine

Prepared according to Procedure A from (4-(3-fluorobenzyloxy)-phenyl)amine (1 eq.) and 4-chloro-6-iodo-quinazoline (1 eq.) in acetonitrile. $^1$H NMR (DMSO-d6) 9.77 (s, 1H); 8.92 (s, 1H); 8.50 (s, 1H); 8.06 (d, 1H); 7.66 (d, 2H); 7.50 (d, 1H); 7.42 (m, 1H); 7.30-7.25 (m, 2H); 7.14 (m, 1H); 7.03 (d, 2H); 5.13 (s, 2H); MS m/z 472 (M+1)

(4-Benzyloxyphenyl)-(6-chloro-pyrido[3,4-d]pyrimidin-4-yl)-amine

Prepared according to Procedure A from 4-benzyloxyaniline (1 eq) and 4,6-dichloro-pyrido[3,4-d]pyrimidine (1 eq); δH (CDCl$_3$) 9.11 (1H,s), 8.78 (1H,s), 7.75 (1H,d), 7.56 (2H,dd), 7.40 (5H,m), 7.15 (2H,d), 5.10 (2H,s); m/z (M+1)$^+$ 409.

(6-Chloropyrido[3,4-d]pyrimidin-4-yl)-(4-(3-fluorobenzyloxy)-phenyl)-amine 4,6-Dichloro-pyrido[3,4-d]pyrimidine (1 g) and 4-(3-fluorobenzyloxy)aniline (1.08 g) in acetonitrile (70 ml) were reacted together as in Procedure A. The product was collected by filtration as a yellow solid (1.86 g); m/z 381 (M+1)$^+$.

N-(4-(3-fluorobenzyloxy)-chlorophenyl)-6-(1-ethoxyvinylether)-quinazolin-4-yl)-amine To a suspension of the 6-iodo-(4-(3-fluorobenzyloxy)-3-chlorophenyl)-quinazolin-4-yl amine (12.6 g, 24.93 mmol) in acetonitrile (100 mL) was added tributyl(1-ethoxyvinyl) stannane (9 g, 24.93 mmol) and bis(triphenylphosphine) palladium (II) chloride (1.75 g, 2.29 mmol). The reaction mixture was refluxed for 18 h, then filtered through a plug of silica gel. The resulting solution was poured into 5% aqueous NH$_4$OH (200 mL) and extracted with ethyl acetate (500 mL). The organic layer was dried over anhydrous sodium sulfate, concentrated, and purified by silica gel chromatography to provide the title compound as a yellow solid (7.2 g, 64% yield). $^1$H NMR (400 MHz, d$_6$ DMSO) δ 9.92 (s, 1H), 8.76 (s, 1H), 8.58 (s, 1H), 8.08 (m, 1H), 8.01 (m, 1H), 7.76 (m, 2H), 7.48 (m, 1H), 7.32 (m, 3H), 7.22 (m, 1H), 5.28 (s, 2H), 5.02 (s, 1H), 4.56 (s, 1H), 4.01 (q, 2H) 1.42 (t, 3H); ESI-MS m/z 449.9 (M+H)$^+$.

N-(4-(Benzyloxy)-chlorophenyl)-6-(1-ethoxyvinylether)-quinazolin-4-yl)-amine To a suspension of the 6-iodo-(4-benzyloxy)-3-chlorophenyl)-quinazolin-4-yl amine (516 mg, 1.06 mmol) in acetonitrile (10 mL) was added tributyl(1-ethoxyvinyl)-stannane (382 mg, 1.06 mmol) and bis(triphenylphosphine) palladium (II) chloride (74 mg,.106 mmol). The reaction mixture was refluxed for 18 h, then filtered through a plug of silica gel. The resulting solution was poured into 5% aqueous NH$_4$H (20 mL) and extracted with ethyl acetate (50 mL). The organic layer was dried over anhydrous sodium sulfate, concentrated, and purified by silica gel chromatography to provide the title compound as a yellow solid (230 mg, 50% yield). $^1$H NMR (400 MHz, d$_6$ DMSO) δ 9.89 (s, 1H), 8.66 (s, 1H), 8.54 (s, 1H), 8.02 (d, 1H), 7.94 (s, 1H), 7.74 (d, 2H), 7.68 (d, 1H), 7.42 (m, 2H), 7.38 (m, 2H), 7.30 (m, 1H), 7.22 (d, 1H), 5.22 (s, 2H), 4.96 (s, 1H), 4.42 (s, 1H), 3.97 (q, 2H), 1.40 (t, 3H).

4-(3-Fluorobenzyloxy)-3-chlorophenyl)-(7-fluoro-6-iodo-quinazolin-4-yl) amine Prepared according to Procedure A from 3-chloro-4-(3-fluorobenzyloxy)-aniline (1 eq.) and 4-chloro-6-iodoquinazoline (1 eq.). ESI-MS m/z 524 (M+1).

5-(4-(4-(3-Fluorobenzyloxy-3-chlorophenylamino)-(6-(5-(1,3-dioxolan-2-yl)-furan-2-yl)-7-fluoro-quinazoline-4-yl)-amine Prepared according to Procedure B from 4-(3-fluorobenzyloxy)-3-chlorophenyl)-(7-fluoro-6-iodo-quinazolin-4-yl) amine (1 eq.), 5-(1,3-dioxolan-2-yl)-2-(tributylstannyl)furan (1.5 eq.), diisopropylethyl amine (5 eq.), and dichlorobis(triphenylphosphine) palladium (0.2 eq.). ESI-MS m/z 536 (M+1).

5-(4-(3-Chloro-4-(3-fluorobenzyloxy)-anilino)-7-fluoro-quinazolin-6-yl)-furan-2-carbaldehyde hydrochloride Prepared according to procedure C from 5-(4-(4-(3-Fluorobenzyloxy-3-chlorophenylamino)-(6-(5-(1,3-dioxolan-2-yl)-furan-2-yl)-7-fluoro-quinazoline-4-yl)-amine (1 g) and THF/1 M aqueous HCl (4:1, 25 mL). ESI-MS m/z 492 (M+1).

5-(4-(4-Benzyloxy-phenylamino)-pyrido[3,4-d]pyrimidin-6-yl)-furan-2-carbaldehyde (4-Benzyloxyphenyl)-(6-chloro-pyrido[3,4-d]pyrimidin-4-yl)-amine (4.0 g, 11.0 mmol), 5-(1,3-dioxolan-2-yl)-2-(tributylstannyl)furan (J. Chem. Soc., Chem. Commun., (1988), 560) (6.0 g, 14.0 mmol) were reacted together in a procedure analogous to Procedure B above for 20 hrs. The reaction mixture was allowed to cool, 1 N HCl (50 ml) added and stirred at room temperature for 15 minutes. The reaction was filtered and the residue washed with dioxane (20 ml) and 2N HCl (20 ml). The combined filtrate and washings were stirred at room temperature for a further hour. The dioxane was removed under vacuum, the reaction diluted with water and the solid which precipitated was collected by filtration, and washed with water, iso-hexane and acetone. This precipitate was converted to the free base by partitioning into a mixture of triethylamine, ethyl acetate and water. The organic phase was washed with water, dried (magnesium sulphate) and the solvent removed under vacuum. The residue was triturated with iso-hexane/ethyl acetate to give the product (2.41 g, 52%) as a yellow solid; δH [$^2$H$_6$]-DMSO 10.60 (1H, b, NH), 9.83 (1H, s, CHO), 9.30 (1H, s, 2-H), 9.08 (1H, s, 5-H or 8-H), 8.76 (1H, s, 5-H or 8-H), 7.89 (1H, d, furan-H), 7.82 (2H, d, 2'-H, 6'-H), 7.65-7.42 (6H, m, 5×Ph-H, furan-H), 7.21 (2H, d, 3'-H, 5'-H), 5.26 (2H, s, OCH$_2$); m/z (M+1)$^+$ 423.

(4-Benzyloxyphenyl)-(6-(5-(1,3-dioxolan-2-yl)-furan-2-yl)-pyrido[3,4-d]pyrimidin-4-yl)-amine Reaction of (4-benzyloxyphenyl)-(6-chloro-pyrido[3,4-d]pyrimidin-4-yl)amine (5.44 g, 15.0 mmol), 5-(1,3-dioxolan-2-yl)-2-(tributylstannyl)furan (10.4 g, 24.2 mmol) and bis (triphenylphosphine)palladium (II) chloride (catalytic amount) in dioxane (150 ml) according to Procedure B, followed by purification by silica gel chromatography (eluted with 50-100% EtOAc/i-hexane), allowed the isolation of the dioxolane product (3.45 g, 7.40 mmol, 49%); δH [$^2$H$_6$]DMSO 10.28 (1H,s), 9.13 (1H,s), 8.69 (1H,s), 8.61 (1H,s), 7.71 (2H,d), 7.31-7.52 (5H,m), 7.14 (1H,d), 7.09 (2H,d), 6.77 (1H,d), 6.03 (1H,s), 5.15 (2H,s), 3.95-4.19 (4H,m).

This could then be converted to 5-(4-(4-Benzyloxy-phenylamino)-pyrido[3,4-d]pyrimidin-6-yl)-furan-2-carbaldehyde (identical to that described above) using Procedure C.

5-(4-(3-Bromo-4-(3-fluorobenzyloxy)-anilino)-quinazolin-6-yl)-furan-2-carbaldehyde Prepared according to Procedure B followed by Procedure C from 6-iodo-(4-(3-fluorobenzyloxy)-3-bromophenyl)- quinazolin-4-yl)amine (1.0 g, 1.82 mmol) and (1,3 dioxolan-2-yl)-2-(tributylstannyl)furan (1.17 g, 2.73 mmol). $^1$H NMR (DMSO-d6) δ 11.89 (bs, 1H); 9.66 (s, 1H); 9.41 (s, 1H); 8.90 (s, 1H); 8.49 (d, 1H); 8.05 (m, 1H); 7.96 (d, 1H); 7.75 (m, 1H); 7.70 (m, 1H); 7.61 (m, 1H); 7.43 (m, 1H); 7.30 (m, 3H); 7.16 (m, 1H); 5.29 (s, 2H).

5-(4-(3-Bromo-4-(benzyloxy)-anilino)-quinazolin-6-yl)-furan-2-carbaldehyde

Prepared according to Procedure B followed by Procedure C from 6-iodo-(4-(benzyloxy)-3-bromophenyl)-quinazolin-4-yl)amine (1.0 eq.) and (1,3 dioxolan-2-yl)-2-(tributylstannyl)furan (1.5 eq.). 1H NMR (DMSO) 11.96 (bs, 1H); 9.67 (s, 1H); 9.42 (s, 1H);8.91 (s, 1H); 8.48 (d, 1H); 8.03 (s, 1H); 7.97 (d, 1H); 7.75 (d, 1H); 7.70 (m, 1H); 7.62 (d, 1H); 7.49 (m, 2H); 7.40 (m, 2H); 7.34 (m, 2H); 5.25 (s, 2H).

(4-Benzyloxyphenyl)-(6-(5-(1,3-dioxolan-2-yl)-furan-2-yl)-7-fluoro-quinazolin-4-yl)-amine Synthesized according to Procedure B from a solution of (4-benzyloxyphenyl)-(6-iodo-7-fluoro-quinazolin-4-yl)-amine hydrochloride (508 mg, 1 mmole), 5-(1,3-dioxolan-2-yl)-2-(tributylstannyl)furan (645 mg, 1.5 mmole), diisopropylethyl amine (650 mg, 5 mmole), and dichlorobis (triphenylphosphine) palladium (140 mg, 0.2 mmole) in 6 ml of DMF under nitrogen was stirred at 100° C. (oil bath temperature) for 4 hours. The cooled reaction mixture was extracted with water (100 ml) and ethyl acetate (100 ml). The organic phase was washed with brine (100 ml). The aqueous layers were combined and washed with additional ethyl acetate (100 ml). The organic layers were combined, dried with MgSO$_4$, filtered and concentrated to a residue. The residue was chromatographed on silica gel with a methanol-chloroform mixture. Fractions were collected, combined, and concentrated. The resultant solid was suspended in dichloromethane (10 ml) and diethyl ether was added facilitate precipitation. The solid was filtered and dried under vacuum at room temperature to yield a yellowish solid 287 mg (59%). $^1$H NMR (400 MHz, DMSO-d$_6$) δ: 10.1 (s, 1H), 8.85(d, 1H), 8.45(s, 1H), 7.6(m, 3H), 7.44(d, 2H), 7.38(m, 2H), 7.31(m,1H), 7.03(m, 2H), 6.94(m, 1H), 6.74(d, 1H), 6.01(s, 1H), 5.1(s, 2H), 4.10(m, 2H), 3.96(m, 2H). ESI-MS m/z 482(M−1).

(4-Benzyloxyphenyl)-(6-(5-(1,3-dioxolan-2-yl)-furan-2-yl)-quinazolin-4-yl)-amine Prepared according to Procedure B from (4-benzyloxyphenyl)-(6-bromoquinazolin-4-yl)-amine (1.5 g, 3.7 mmol) and 5-(1,3-dioxolan-2-yl)-2-(tributylstannyl)-furan (1.9 g, 4.42 mmol) dissolved in dioxan (30 ml) and heated at reflux under nitrogen for 6 hr. The solvent was removed from the cooled reaction under vacuum, and the residual oil was triturated with iso-hexane/ethyl acetate to give the product (1.07 g, 62%) as a pale yellow solid; δH [$^2$H$_6$]-DMSO 9.96 (1H, b, NH), 8.80 (1H, s, 5-H), 8.51 (1H, s, 2-H), 8.18 (1H, d, 7-H), 7.80 (1H, d, 8-H), 7.70 (2H, d, 2'-H, 6'-H), 7.58-7.30 (5H, m 5×Ph-H), 7.10 (3H, m, 3'-H, 5'-H, furan 3-H), 6.78 (1H, d, furan 4-H), 6.12 (1H, s, CH0$_2$), 5.18 (2H, s, PhC$\underline{H}_2$), 4.22-3.94 (4H, m, 2×CH$_2$); m/z 466 (M+1)$^+$.

(4-Benzyloxyphenyl)-(6-(5-(1,3-dioxolan-2-yl)-furan-2-yl)-7-methoxy-quinazolin-4-yl)-amine Prepared according to Procedure B from a solution of (4-benzyloxyphenyl)-7-methoxy-6-trifluoromethanesulfonyl-quinazolin-4-yl)-amine (0.30 g, 0.59 mmol), 5-(1,3-dioxolan-2-yl)-2-(tributylstannyl)furan (0.37 g, 0.86 mmol), lithium chloride (78 mg, 1.8 mmol), and dichloro-bis(triphenylphosphine)palladium (90 mg, 0.13 mmol) in 2 ml of DMF under nitrogen was stirred at 85-90° C. for 50 minutes. The cooled reaction mixture was partitioned between 30 ml of water and 40 ml of ethyl acetate. The organic solution was washed with 30 ml of brine, dried with Na$_2$SO$_4$ and concentrated in vacuo. The residue was chromatographed on silica gel with hexanes/ethyl acetate (1:1 to 0:1). The resulting solution was concentrated to near dryness and the resulting solid suspended in ether and filtered to give 0.232 g of product as a pale yellow solid. $^1$H NMR (400 MHz, DMSO-d$_6$) δ: 9.90(s, 1H), 8.71(s, 1H), 8.40(s, 1H), 7.60(d, 2H), 7.44(d, 2H), 7.37(t, 2H), 7.30(t, 1H), 7.24(s, 1H), 7.00(m, 3H), 6.67(d, 1H), 5.99(s, 1H), 5.09(s, 2H), 4.10(m, 2H), 4.02(s, 3H), 3.95(m, 2H). ESI-MS m/z 496(M+1).

(4-Benzyloxyphenyl)-(6-(5-(1,3-dioxolan-2-yl)-furan-2-yl)-7-fluoro-quinazolin-4-yl)-amine Prepared according to Procedure B from a solution of (4-benzyloxyphenyl)-(6-iodo-7-fluoro-quinazolin-4-yl)-amine hydrochloride (508 mg, 1 mmole), 5-(1,3-dioxolan-2-yl)-2-(tributylstannyl)furan (645 mg, 1.5 mmole), diisopropylethyl amine (650 mg, 5 mmole), and dichlorobis (triphenylphosphine) palladium (140 mg, 0.2 mmole) in 6 ml of DMF under nitrogen was stirred at 100° C. (oil bath temperature) for 4 hours. The cooled reaction mixture was extracted with water (100 ml) and ethyl acetate (100 ml). The organic phase was washed with brine (100 ml). The aqueous layers were combined and washed with additional ethyl acetate (100 ml). The organic layers were combined, dried with MgSO$_4$, filtered and concentrated to a residue. The residue was chromatographed on silica gel with a methanol-chloroform mixture. Fractions were collected, combined, and concentrated. The resultant solid was suspended in dichloromethane (10 ml) and diethyl ether was added to facilitate precipitation. The solid was filtered and dried under vacuum at room temperature to yield a yellow solid 287 mg (59%). $^1$H NMR (400 MHz, DMSO-d$_6$) δ: 10.1 (s, 1H), 8.85 (d, 1H), 8.45 (s, 1H), 7.6 (m, 3H), 7.44 (d, 2H), 7.38 (m, 2H), 7.31 (m, 1H), 7.03 (m, 2H), 6.94 (m, 1H), 6.74 (d, 1H), 6.01 (s, 1H), 5.1 (s, 2H), 4.10 (m, 2H), 3.96 (m, 2H). ESI-MS m/z 482(M−1).

5-(4-(4-Benzyloxy-phenylamino)-quinazolin-6-yl)-furan-2-carbaldehyde

Prepared according to Procedure C from 4-(4-benzyloxy-phenylamino)-(6-(5-(1,3-dioxolan-2-yl)-furan-2-yl)-quinazolin-4-yl)-amine (1.0 g, 2.1 mmol). The precipitate which formed was collected by filtration and washed with acetone, then partitioned between ethyl acetate, triethylamine and water. The organic phase was washed with water, dried (magnesium sulphate) and the solvent was removed under vacuum. Trituration with iso-hexane/ethyl acetate gave the product as an orange solid (610 mg, 69%); δH [$^2$H$_6$]-DMSO 10.05 (1H, b, NH), 9.62 (1H, s, CHO), 8.95 (1H, s, 5-H), 8.48 (1H, s, 2-H), 8.24 (1H, d, 7-H), 7.80 (1H, d, 8-H), 7.70 (1H, d, furan 4-H), 7.59 (2H, d, 2'-H, 6'-H), 7.48-7.25 (6H, m, 5×Ph-H, furan 3-H), 7.02 (2H, m, 3'-H, 5'-H), 5.09 (2H, s, CH$_2$); m/z 422 (M+1)$^+$.

5-(4-(4-Benzyloxy-phenylamino)-7-methoxy-quinazolin-6-yl)-furan-2-carbaldehyde hydrochloride Prepared according to Procedure C from (4-benzyloxyphenyl)-(6-(5-(1,3-dioxolan-2-yl)-furan-2-yl)-7-methoxy-pyrido[3,4-d]pyrimidin-4-yl)-amine(0.301 g, 0.60 mmol). After stirring 45 minutes, the resulting suspension was filtered and washed with ether to give 0.26 g of product as a yellow solid. $^1$H NMR (400 MHz, DMSO-d$_6$) δ: 11.67(br s, 1H), 9.68(s, 1H), 9.14(s, 1H), 8.78(s, 1H), 7.73(d, 1H), 7.52(d, 2H), 7.44(m, 3H), 7.39(m, 3H), 7.32(m, 1H), 7.11(d, 2H), 5.14(s, 2H), 4.12(s, 3H). ESI-MS m/z 452(M+1).

(4-Benzyloxy-phenyl)-(6-(5-(2-nitroethylene)-furan-2-yl)-quinazolin-4-yl)-amine

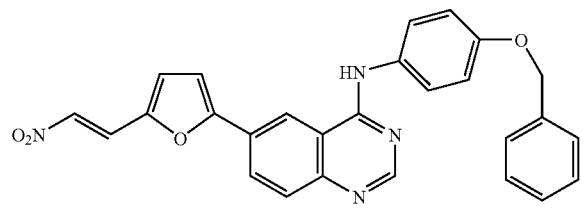

Prepared according to Procedure (L) utilizing 5-(4-(4-benzyloxy-phenylamino)-quinazolin-6-yl)-furan-2-carbaldehyde (0.69 g, 1.589 mmol), ammonium acetate (0.141 g) and nitromethane (20 mL). $^1$H (DMSO) 9.82 (s, 1 H), 8.92 (s, 1 H), 8.47 (s, 1 H), 8.31 (d, 1 H), 8.04 (m, 2 H), 7.76 (1 H),7.62 (d, 2 H), 7.29-7.44 (7 H), 7.04 (d, 2 H), 5.09 (s, 2 H). LC/MS 465 (MH$^+$).

(4-Benzyloxy-phenyl)-(6-(5-(2-aminoethyl)-furan-2-yl)-quinazolin-4-yl)-amine

Preparation according to Procedure (M) utilizing (4-benzyloxy-phenyl)-(6-(5-(2-nitroethylene)-furan-2-yl)-quinazolin-4-yl)-amine (0.134 g, 0.289 mmol) and lithium aluminium hydride (1.0 M in THF, 0.87 mL). $^1$H (DMSO) 9.69 (s, 1 H), 8.55 (s, 1 H), 8.31 (s, 1 H), 7.97 (d, 1 H), 7.60 (d, 1 H), 7.51 (d, 2 H), 7.17-7.34 (m, 5 H), 6.92 (d, 2 H), 6.86 (d, 1 H), 6.20 (d, 1 H), 4.99 (s, 2 H), 2.79 (t, 2 H), 2.68 (t, 2 H). LC/MS 437 (MH$^+$).

(4-(3-Fluorobenzyloxy)-3-chlorophenyl)-(6-(5-(2-nitroethylene)-furan-2-yl)-quinazolin-4-yl)-amine Prepared according to Procedure (L) utilizing 5-(4-{3-chloro-4-[(3-fluorobenzyl)oxy]anilino}-6-quinazolinyl)-2-furaldehyde (2.0 g, 4.228 mmol), ammonium acetate (0.359 g) and nitromethane (30 mL). $^1$H (DMSO) 9.87 (s, 1 H), 8.90 (s, 1 H), 8.55 (s, 1 H), 8.34 (d, 1 H), 8.04 (m, 2 H), 7.96 (d, 1 H), 7.80 (d, 1 H), 7.66 (d, 1 H), 7.26-7.42 (m, 6 H), 7.14 (m, 1 H), 5.22 (s, 2 H). LC/MS 517 (MH$^+$).

(4-(3-Fluorobenzyloxy)-3-chlorophenyl)-(6-(5-(2-aminoethyl)-furan-2-yl)-quinazolin-4-yl)-amine Prepared according to Procedure (M) utilizing (4-(3-fluorobenzyloxy)-3-chlorophenyl)-(6-(5-(2-nitroethylene)-furan-2-yl)-quinazolin-4-yl)-amine (0.123 g, 0.239 mmol) and lithium aluminum hydride (1.0 M in THF, 0.72 mL). $^1$H (DMSO) 9.86 (s, 1 H), 8.63 (s, 1 H), 8.48 (s, 1 H), 8.08 (d, 1 H), 7.95 (d, 1 H), 7.68-7.75 (m, 2 H), 7.39-7.43 (m, 1 H), 7.22-7.29 (m, 3 H), 7.15 (m, 1 H), 6.96 (d, 1 H), 6.29 (d, 1 H), 5.21 (s, 2 H), 2.85 (t, 2 H), 2.75 (t, 2 H). Electrospray MS m/z 489 (MH$^+$).

(4-Benzyloxy-phenyl )-(6-((5-(2-methylthio-ethylamino)-methyl)-furan-2-yl)-quinazolin-4-yl)-amine dihydrochloride 5-(4-(4-Benzyloxy-phenylamino)-quinazolin-6-yl)-furan-2-carbaldehyde (100 mg) and (methylthio)ethylamine (80 mg) in dichloromethane (5 ml) were reacted together as in Procedure D. Purification using column chromatography, followed by conversion to the hydrochloride salt gave a yellow solid (61 mg). m/z 497 (M+1)$^+$.

(4-(3-Fluorobenzyloxy)-phenyl)-(6-(5-(2-(methylthio)-ethylaminomethyl)-furan-2-yl)-pyrido[3,4-d]pyrimidin-4-yl)-amine (5-(4-(4-(3-Fluorobenzyloxy)-phenyl)-pyrido[3,4-d]pyrimidin-6-yl)-furan-2-carbaldehyde (125 mg) and (methylthio)ethylamine (0.08 ml) in dichloromethane (5 ml) were reacted together as in Procedure D. Purification using a Bond Elut™ cartridge gave a yellow oil (80 mg); m/z 516 (M+1)$^+$.

(4-(3-Fluorobenzyloxy)-3-chlorophenyl)-(6-(2-(2-cyano-methyl)-thiazol-4-yl)-quinazolin-4-yl)-amine N-(4-(3-fluorobenzyloxy)-chlorophenyl)-6-(1-ethoxyvinylether)-quinazolin-4-yl)-amine (0.67 mmol) and NBS (0.67 mmol) were reacted together in THF as in Procedure (F-2) to provide the crude α-bromo ketone intermediate. This material was then immediately reacted with 2-cyanothioacetamide (0.67 mmol) in DMF following procedure (F-3) to provide the title compound after purification by chromatography. $^1$H NMR (CDCl$_3$) δ 8.76 (s,1 H), 8.57 (s, 1H), 8.16 (d, 1H), 7.92 (d, 1 H), 7.85 (s, 1 H), 7.75 (s, 1H), 7.62 (s, 1 H), 7.58 (d, 1H), 7.36 (m, 1H), 7.21 (m, 2H), 6.99 (m, 2H), 5.17 (s, 2H), 4.22 (s, 2H). Electrospray MS m/z 502 (MH+).

(4-(3-Fluorobenzyloxy)-3-chlorophenyl)-(6-(2-(2-aminoethyl)-thiazol-4-yl)-quinazolin-4-yl)-amine (4-(3-Fluorobenzyloxy)-3-chlorophenyl)-(6-(2-(2-cyanomethyl)-thiazol-4-yl)-quinazolin-4-yl)-amine (0.239 mmol) was treated with borane dimethylsulfide in THF as outlined in procedure (K) to provide the title compound. Electrospray MS m/z 506.1 (MH+).

(4-(3-Fluorobenzyloxy)-3-chlorophenyl)-(6-(2-(2-(methylsulfonyl)acetamidoethyl)-thiazol-4-yl)-quinazolin-4-yl)-amine (4-(3-Fluorobenzyloxy)-3-chlorophenyl)-(6-(2-(2-aminoethyl)-thiazol-4-yl)-quinazolin-4-yl)-amine (0.229 mmol) was reacted with methanesulfonyl acetic acid (0.252 mmol) and 1-(3-dimethylaminopropyl)-3-ethylcarbodiimide hydrochloride (0.252 mmol) in DMF as outlined in procedure (I) to provide the title compound after purification by chromatography. $^1$H NMR (CDCl$_3$) δ 8.82 (s, 1H), 8.68 (s, 1H), 8.44 (s, 1H), 8.14 (d, 1 H), 8.02 (m, 1H), 7.92 (d, 1H), 7.81 (s, 1H), 7.62 (m, 1H), 7.55 (s, 1H), 7.36 (m, 1H), 7.21 (m, 2H), 7.02 (m, 2H), 5.18 (s, 2H), 3.95 (s, 2H), 3.91 (m, 2H), 3.36 (m, 2H), 2.88 (s, 3H). Electrospray MS m/z 625.87 (MH+).

(4-(3-Fluorobenzyloxy)-3-chlorophenyl)-(6-(5-(2-(methylsulfonyl)acetamidoethyl)-furan-2-yl)-quinazolin-4-yl)-amine Preparation according to Procedure (I) utilizing (4-(3-fluorobenzyloxy)-3-chlorophenyl)-(6-(5-(2-aminoethyl)-furan-2-yl)-quinazolin-4-yl)-amine (26 mg, 0.0537 mmol), methanesulfonylacetic acid (22.2 mg, 0.161 mmol), 1-(3-dimethylaminopropyl)-3-ethylcarbodiimide hydrochloride (30.0 mg, 0.161 mmol) and N,N-diisopropylethylamine (0.028 mL, 0.161 mmol). ¹H (DMSO) 9.84 (s, 1 H), 8.65 (s, 1 H), 8.49 (s, 1 H), 8.10 (d, 1 H), 7.96 (d, 1 H), 7.73 (d, 1 H), 7.69 (m, 1 H), 7.41 (m, 1 H), 7.22-7.29 (m, 3 H), 7.13 (m, 1 H), 6.98 (d, 1 H), 6.35 (d, 1 H), (5.21 (s, 2 H), 4.02 (s, 2 H), 3.07 (t, 2 H), 3.05 (s, 3 H), 2.87 (t, 2 H). Electrospray m/z 609 (MH+).

5-(4-(4-Benzyloxy-phenylamino)-7-fluoro-quinazolin-6-yl)-furan-2-carboxaldehyde hydrochloride Prepared according to Procedure C from a stirred solution of (4-benzyloxyphenyl)-(6-(5-(1,3-dioxolan-2-yl)-furan-2-yl)-7-fluoro-quinazolin-4-yl)-amine (0.51 grams, 1.1 mmol) in 20 ml of THF was added 5 ml of 1 N HCl. After stirring for 90 minutes, the resultant suspension was filtered and washed with diethyl ether (200 ml) to yield, after drying under vacuum, a yellow solid (0.32 grams, 61% yield). δ¹H NMR (400 MHz, DMSO-d₆) 11.52(s, 1H), 9.70(s, 1H), 9.25(d, 1H),8.76(s, 1H), 7.76(m, 2H), 7.55(d, 2H), 7.45(d, 2H), 7.33(m, 4H), 7.11(d, 2H), 5.14(s, 2H). ESI-MS m/z 440(M+1).

5-(4-(4-Benzyloxy-phenylamino)-quinazolin-6-yl)-furan-2-carbaldehyde hydrochloride Prepared according to Procedure C from 4-(4-benzyloxyphenylamino)-(6-(5-(1,3-dioxolan-2-yl)-furan-2-yl)-quinazolin-4-yl)-amine (6.70 g, 14.4 mmol). The resulting precipitate was collected by filtration and washed with water to give the hydrochloride salt as a yellow solid (6.50 g, 14.1 mmol, 98%); δH [²H₆]DMSO 12.15 (1H,s), 9.69 (1H,s) 9.58 (1H,s), 8.88 (1H,s), 8.50 (1H,dd), 8.02 (1H,d), 7.77 (1H,d), 7.62-7.74 (3H,m), 7.31-7.52 (5H,m), 7.15 (2H,d), 5.17 (2H, s).

5-(4-{3-Chloro-4-[(3-fluorobenzyl)oxy]anilino}-6-quinazolinyl)-2-furaldehyde Prepared according to Procedure B utilizing 6-Iodo-(4-(3-fluorobenzyloxy)-3-chlorophenyl)-quinazolin-4yl)amine (1 eq) and 5-(1,3-dioxolan-2-yl)-2-(tributylstannyl)furan (1.5 eq) in dioxane followed by Procedure C using THF and aqueous HCl (1 M). ¹H NMR 400 MHz (DMSO-d6) 12.0 (s, 1H); 9.66 (s, 1H); 9.41 (s, 1H); 8.93 (s, 1H); 8.51 (d, 1H); 7.97 (d, 1H); 7.89 (s, 1H); 7.76 (d, 1H); 7.64 (d, 1H); 7.61 (d, 1H); 7.46 (m, 1H); 7.37-7.28 (m, 3H); 7.16 (m, 1H); 5.30 (s, 2H). Electrospray MS 501, 472 m/z (M−1).

5-(4-{3-Chloro-4-benzyloxyanilino}-6-quinazolinyl)-2-furaldehyde

Prepared according to Procedure B utilizing 6-Iodo-(4-(benzyloxy)-3-chlorophenyl)-quinazolin-4yl)amine (1 eq) and 5-(1,3-dioxolan-2-yl)-2-(tributylstannyl)furan (1.5 eq) in dioxane followed by Procedure C using THF and aqueous HCl (1 M). ¹H NMR 400 MHz (DMSO-d6) 9.66 (s,1H); 9.16 (s,1H); 8.83 (s,1H); 8.45 (d,1H); 7.91 (d,1H); 7.88 (d,1H); 7.75 (d,1H); 7.62 (m,1H) 7.51-7.31 (m,7H); 5.25 (s,2H) Electrospray MS 456 m/z (M+1).

(6-(5-(1,3-Dioxolan-2-yl)-furan-2-yl)-pyrido[3,4-d]pyrimidin-4-yl)-(4-(3-fluorobenzyloxy)-phenyl)-amine (6-Chloropyrido[3,4-d]pyrimidin-4-yl)-(4-(3-fluorobenzyloxy)-phenyl)-amine (1.85 g) and 5-(1,3-dioxolan-2-yl)-2-(tributylstannyl)-furan (3.82 g) in dioxan (40 ml) were reacted together as in Procedure B. The mixture was evaporated and the residue suspended in dichloromethane. This was then filtered through Celite® and the solvent evaporated. The gummy residue was then triturated with hexane giving a beige solid (1.74 g); m/z 485 (M+1)⁺.

5-(4-(4-(3-Fluorobenzyloxy)-phenylamino)-pyrido[3,4-d]pyrimidin-6-yl)-furan-3-carbaldehyde (6-Chloropyrido[3,4-d]pyrimidin-4-yl)-(4-(3-fluorobenzyloxy)-phenyl)-amine (1 g) and 5-(tributylstannyl)-furan-3-carbaldehyde (J. Org. Chem. (1992), 57(11), 3126-31) (1.84 g) in dioxan (35 ml) were reacted together as in Procedure B. The solvent was evaporated and the residue suspended in dichloromethane. The mixture was filtered through Celite® and then evaporated. The residue was triturated with hexane giving a beige solid (1 g); m/z 441 (M+1)⁺.

5-(4-(4-(3-Flauorobenzyloxy)-phenylamino)-pyrido[3,4-d]pyrimidin-6-yl)-furan-2-carbaldehyde (6-(5-(1,3-Dioxolan-2-yl)-furan-2-yl)-pyrido[3,4-d]pyrimidin-4-yl)-(4-(3-fluorobenzyloxy)-phenyl)-amine (500 mg) was treated with acid as in Procedure C. The product was collected by filtration as a beige solid (251 mg); m/z 441 (M+1)⁺.

4-(4-(4-Benzyloxy-phenyl)-amino)-quinazolin-6-yl)-thiazol-2-carbaldehyde (4-Benzyloxy-phenyl)-(6-iodo-quinazolin-4-yl)-amine (2 g) and 4-(tributylstannyl)-thiazol-2-carbaldehyde (3.28 g) in dioxan (25 ml) were reacted together as in Procedure B. The mixture was evaporated and the residue purified using column chromatography, giving a yellow solid (849 mg); m/z 439 (M+1)⁺.

Ethyl 3-(5-{4-[4-(benzyloxy)-3-chloroanilino]-6-quinazolinyl}-2-furyl)-2-propenoate Prepared according to Procedure G utilizing 5-(4-{3-chloro-4-benzyloxyanilino}-6-quinazolinyl)-2-furaldehyde (0.672 g, 1.48 mmol) and triethylphosphonoacetate (0.73 mL, 3.69 mmol) to afford the title compound (0.65 g). Electrospray MS m/z 526 (MH⁺).

Ethyl 3-[5-(4-{3-chloro-4-[(3-fluorobenzyl)oxy]anilino}-6-quinazolinyl)-2-furyl]-2-propenoate Prepared according to Procedure G utilizing 5-(4-{3-chloro-4-(3-fluorobenzyloxy)anilino}-6-quinazolinyl)-2-furaldehyde (0.62 g, 1.31 mmol) and triethylphosphonoacetate (0.65 mL, 3.27 mmol) to afford the title compound (0.5 g). Electrospray MS m/z 542 (M−H).

3-(5-{4-[4-(Benzyloxy)-3-chloroanilino]-6-quinazolinyl}-2-furyl)-2-propenoic acid Prepared according to Procedure H utilizing ethyl 3-(5-{4-[4-(benzyloxy)-3-chloroanilino]-6-quinazolinyl}-2-furyl)-2-propenoate (0.65 g) and aqueous sodium hydroxide (2M, 4 mL) in THF (8 mL) and ethanol (4 mL) to afford the title compound (0.63 g). Electrospray MS m/z 498 (MH⁺).

3-(5-{4-[4-(3-Fluoro-benzyloxy)-3-chloroanilino]-6-quinazolinyl}-2-furyl)-2-propenoic acid Prepared according to Procedure H utilizing ethyl 3-(5-{4-[4-(3-fluorobenzyloxy)-3-chloroanilino]-6-quinazolinyl}-2-furyl)-2-propenoate (0.50 g) and aqueous sodium hydroxide (2M, 2 mL) in THF (6 mL) to afford the title compound (0.46 g). Electrospray MS m/z 516 (MH+).

3-(5-{4-[4-(3-Fluoro-benzyloxy)-3-chloroanilino]-6-quinazolinyl}-2-furyl)-N-[2-(phenylsulfonyl)ethyl]-2-propenamide Prepared according to Procedure (I) utilizing 3-(5-{4-[4-(3-fluorobenzyloxy)-3-chloroanilino]-6-quinazolinyl}-2-furyl)-2-propenoic acid (0.25 g, 0.45 mmol), 2-(phenylsulfonyl)-ethylamine hydrochloride (0.30 g, 1.36 mmol), 1-(3-dimethylaminopropyl)-3-ethylcarbodiimide hydrochloride (0.26 g, 1.36 mmol) and diisopropylethylamine (0.55 mL, 3.18 mmol) in acetonitrile. Electrospray MS m/z 683 (MH+).

3-(5-{4-[4-(Benzyloxy)-3-chloroanilino]-6-quinazolinyl}-2-furyl)-N-[2-methanesulfonyl)ethyl]-2-propenamide Prepared according to Procedure I utilizing 3-(5-{4-[4-(benzyloxy)-3-chloroanilino]-6-quinazolinyl}-2-furyl)-2-propenoic acid (0.095 g, 0.19 mmol), carbonyldiimidazole (0.10 g, 0.61 mmol), and methanesulfonylethylamine (0.14 g, 1.1 mmol) in CH3CN to afford the title compound (0.06 g). Electrospray MS m/z 625 (M–Na+).

3-(5-{4-[4-(3-Fluoro-benzyloxy)-3-chloroanilino]-6-quinazolinyl}-2-furyl)-N-[2-iso-propanesulfonyl)ethyl]-2-propenamide Prepared according to Procedure I utilizing 3-(5-{4-[4-(3-fluorobenzyloxy)-3-chloroanilino]-6-quinazolinyl}-2-furyl)-2-propenoic acid (0.22 g, 0.4 mmol), carbonyldiimidazole (0.58 g, 3.6 mmol), and iso-propanesulfonylethylamine (0.24 g, 1.6 mmol) in DMF to afford the title compound (0.088 g). Electrospray MS 649 m/z (MH+).

3-(5-{4-[4-(3-Fluoro-benzyloxy)-3-chloroanilino]-6-quinazolinyl}-2-furyl)-N-[2-(n-propanesulfonyl)ethyl]-2-propenamide Prepared according to Procedure I utilizing 3-(5-{4-[4-(3-fluoroenzyloxy)-3-chloroanilino]-6-quinazolinyl}-2-furyl)-2-propenoic acid (0.23 g, 0.42 mmol), carbonyldiimidazole (0.21 g, 1.27 mmol), and n-propanesulfonylethylamine (0.16 g, 0.85 mmol) in DMF to afford the title compound (0.05 g) after purification by chromatography. Electrospray MS m/z 649 (MH+).

3-[5-(4-{3-chloro-4-[(3-fluorobenzyl)oxy]anilino}-6-quinazolinyl)-2-furyl]-2-methen alcohol Prepared according Procedure N utilizing 5-(4-(3-Chloro-4-(3-fluorobenzyloxy)-anilino)-7-fluoro-quinazolin-6-yl)-furan-2-carbaldehyde (1.31 g, 2.76 mmol), sodium cyanoboron hydride (0.347 g, 5.52 mmol), acetic acid (0.25 mL) in 25 mL of methylene chloride to afford the title compound (1.09 g) by chromatography. 1H NMR 400 MHz (DMSO-d6) 9.93 (1 H, s), 8.72 (1 H, s), 8.52 (1 H, s), 8.13 (1 H, s), 7.98 (1 H, s), 7.88 (1 H, d), 7.76-7.72 (2 H, m), 7.44 (1 H, m), 7.32-7.24 (2 H, m), 7.16 (1 H, m), 7.03 (1 H, s), 6.48 (1 H, d, J=4.0 Hz), 5.31 (1 H, t), 5.23 (2 H, s), 4.49 (1 H, d, J=5.2 Hz). Electroscopy MS m/z 476 (M+H+)

EXAMPLES

Example 1

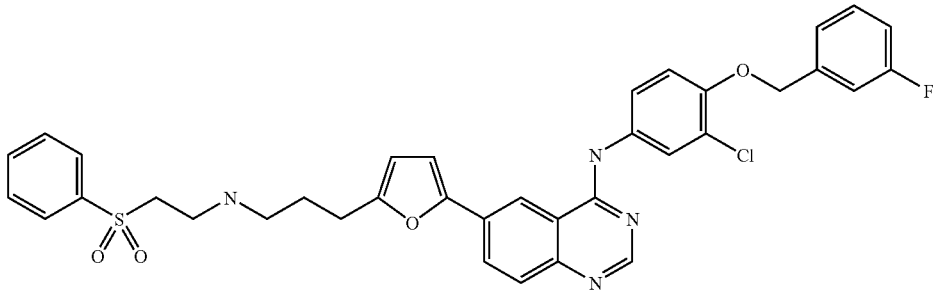

(4-(3-Fluorobenzyloxy)-3-chlorophenyl)-(6-(2-((2-phenylsulphonyl-ethylamino)-propyl)-furan-2-yl)-quinazolin-4-yl)-amine Prepared according to Procedure (J) utilizing 3-(5-{4-[4-(3-fluoro-benzyloxy)-3-chloroanilino]-6-quinazolinyl}-2-furyl)-N-[2-(phenylsulfonyl)ethyl]-2-propenamide (0.070 g, 0.103 mmol) and borane dimethyl sulfide (2M, 0.18 mL). Electrospray MS m/z 673 (MH+).

Example 2

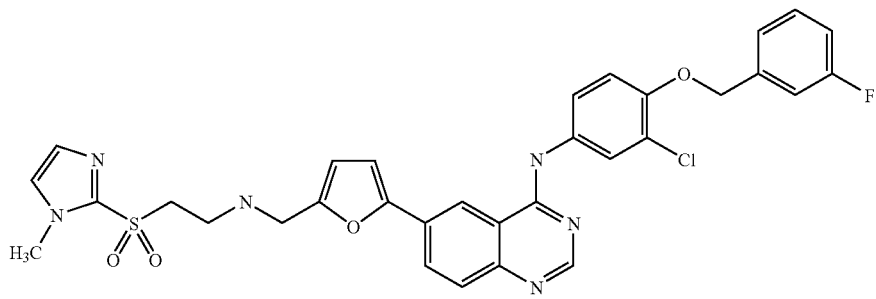

**(4-(3-Fluorobenzyloxy)-3-chlorophenyl)-(6-(2-((2-
(2-N-methylimidazolyl)-sulphonyl-ethylamino)-
methyl)-furan-2-yl)-quinazolin-4-yl)-amine**

The title compound and its hydrochloride salt are prepared according to Procedure D utilizing 5-{4-[4-(3-fluorobenzyloxy)-3-chloroanilino]-6-quinazolinyl}-2-furaldehyde (0.264 mmol, 0.125 g), 1-Methylimidazolesulfonylethyl amine hydrochloride salt (0.565 mmol, 0.1 g) in the presence of Et$_3$N (0.6 mmol, 0.8 mL) and NaBH$_4$ (0.79 mmol, 0.029 g) in THF/MeOH.

Example 3

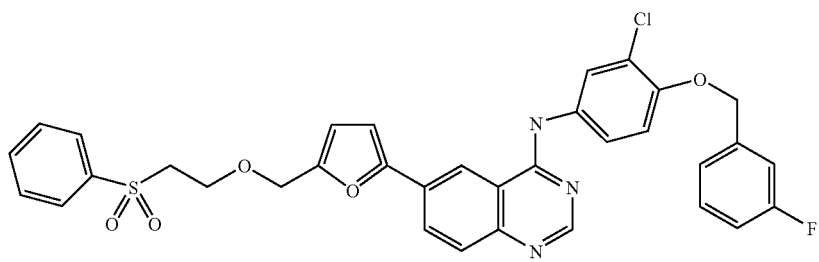

4-{3-chloro-4-[(3-fluorobenzyl)oxy]phenyl}-6-(5-{[2-(phenylsulfonyl)ethoxy]methyl}-2-furyl)-4-quinazolinamine

Prepared according to Procedure O utilizing 3-[5-(4-{3-chloro-4-[(3-fluorobenzyl)oxy]anilino}-6-quinazolinyl)-2-furyl]-2-methen alcohol (83 mg, 0.175 mmol), phenyl vinyl sulfone (35 mg, 0.21 mmol) and sodium hydride (60% in mineral oil, 0.7 mg, 0.017 mmol) in DMF (3 mL) to provide the title compound (68 mg) after purification by chromatography. $^1$H NMR 400 MHz (DMSO-d6) 9.97 (1 H, s), 8.70 (1 H, s), 8.52 (1 H, s), 8.10 (1 H, d), 7.94 (1 H, s), 7.84-7.51 (7 H, m), 7.43 (1 H, m), 7.29-7.23 (3 H, m), 7.13 (1 H, m), 7.01 (1 H, d), 6.52 (1 H, d), 5.22 (2 H, s), 4.36 (2 H, s), 3.72 (2 H, t), 3.61 (2 H, t). LC/MS m/z 644 (M+H$^+$).

Example 4

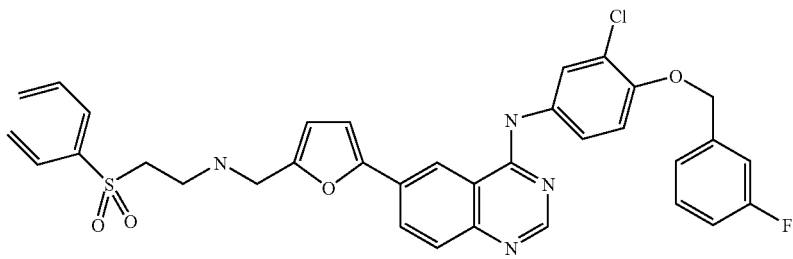

(4-(3-Fluorobenzyloxy)-3-chlorophenyl)-(6-(2-((2-phenylsulphonyl-ethylamino)-methyl)-furan-2-yl)-quinazolin-4-yl)-amine The title compound and its hydrochloride salt are prepared according to Procedure D utilizing 5-{4-[4-(3-fluorobenzyloxy)-3-chloroanilino]-6-quinazolinyl}-2-furaldehyde (0.317 mmol, 0.15 g), Phenylsulfonylethyl amine hydrochloride salt (0.475 mmol, 0.105 g) in the presence of Et$_3$N (0.51 mmol, 0.067 mL) and NaBH$_4$ (0.79 mmol, 0.029 g) in THF/MeOH. $^1$H NMR (DMSO-d6) 11.76 (bs, 1H); 9.82 (bs, 2H); 9.59 (s, 1H); 8.91 (s, 1H); 8.37 (d, 1H); 8.04 (m, 1H); 7.98-7.89 (m, 3H); 7.78 (m, 2H); 7.67 (m, 2H); 7.48 (m, 1H); 7.37-7.27 (m, 4H); 7.19 (m, 1H); 6.78 (m, 1H); 5.31 (s, 2H); 4.41 (s, 2H); 3.89 (m, 2H); 3.27 (m, 2H). Electrospray MS 643.

Example 5

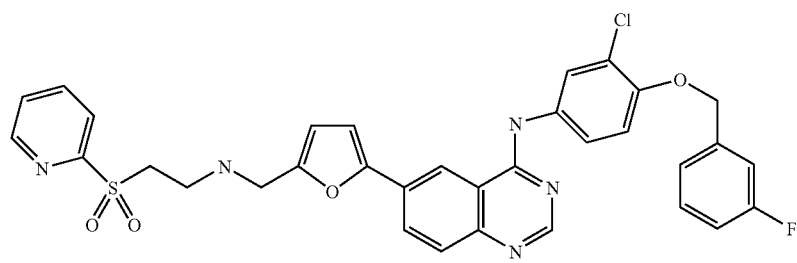

(4-(3-Fluorobenzyloxy)-3-chlorophenyl)-(6-(2-((2-(2-pyridyl)-sulphonyl-ethylamino)-methyl)-furan-2-yl)-quinazolin-4-yl)-amine The title compound and its hydrochloride salt are prepared according to Procedure D utilizing 5-{4-[4-(3-fluorobenzyloxy)-3-chloroanilino]-6-quinazolinyl}-2-furaldehyde (0.264 mmol, 0.125 g), 2-Pyridylsulfonylethyl amine hydrochloride salt (0.473 mmol, 0.88 g) in the presence of Et$_3$N (0.51 mmol, 0.67 mL) and NaBH$_4$ (0.793 mmol, 0.03 g) in THF/MeOH. $^1$H NMR (DMSO-d6) 11.63 (bs, 1H); 9.84 (bs, 2H); 9.56 (bs, 1H); 8.90 (s, 1H); 8.78 (d, 1H); 8.37 (d, 1H); 8.18 (m, 1H); 8.08 (d, 1H); 8.03 (m, 1H); 7.94 (d, 1H); 7.78 (m, 2H); 7.47 (m, 1H); 7.36-7.29 (m, 4H); 7.19 (m, 1H); 6.80 (m, 1H); 5.30 (s, 2H); 4.44 (s, 2H); 4.02 (m, 2H); 3.40 (m, 2H). Electrospray MS 644.

Example 6

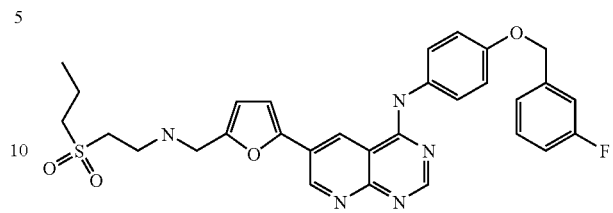

(4-(3-Fluorobenzyloxy)-phenyl)-(6-(2-((2-propane-sulphonyl-ethylamino)methyl)-furan-2-yl)-pyrido[3,4-d]pyrimidin-4-yl)-amine;

5-(4-(4-(3-Fluorobenzyloxy)-phenylamino)-pyrido[3,4-d]pyrimidin-6-yl)-furan-2-carbaldehyde (0.31 mmol) and 2-n-propanesulphonyl-ethyl amine (0.94 mmol) were reacted together in dimethoxyethane as in Procedure D. $^1$H NMR (DMSO) 11.25 (bs, 1H); 9.88 (bs, 1H); 9.49 (s, 1H); 9.20 (s, 1H); 8.80 (s, 1H); 7.85 (d, 2H); 7.44 (m, 1H); 7.32-7.27 (m, 3H); 7.16 (m, 1H); 7.11 (d, 2H); 6.87 (m, 1H); 5.18 (s, 2H); 4.46 (s, 2H); 3.66 (m, 2H); 3.45 (m, 2H); 3.23 (m, 2H); 1.71 (m, 2H); 0.97 (m, 3H). Electrospray MS m/z 576 (MH$^+$).

Example 7

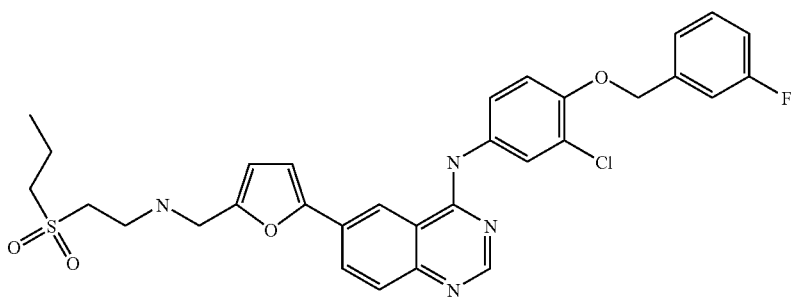

(4-(3-Fluorobenzyloxy)-3-chlorophenyl)-(6-(2-((2-propanesulphonyl-ethylamino)-methyl)-furan-2-yl)-quinazolin-4-yl)-amine;

5-(4-{3-Chloro-4-[(3-fluorobenzyl)oxy]anilino}-6-quinazolinyl)-2-furaldehyde (0.32 mmol) and 2-n-propane-sulphonyl-ethyl amine (0.95 mmol) were reacted together in dimethoxyethane as in Procedure D. $^1$H NMR (DMSO) 11.85 (bs, 1H); 9.94 (bs, 2H); 9.67 (s, 1H); 8.95 (s, 1H); 8.45 (d, 1H); 8.08 (s, 1H); 8.00 (d, 1H); 7.84 (d, 1H); 7.50 (m, 1H); 7.38 (m, 4H); 7.22 (m, 1H); 6.88 (s, 1H); 5.35 (s, 2H) 4.48 (s, 2H); 3.68 (m, 2H); 3.46 (m, 2H); 3.26 (m, 2H); 1.75 (m, 2H); 1.01 (m, 3H). Electrospray MS m/z 609 (MH$^+$).

Example 8

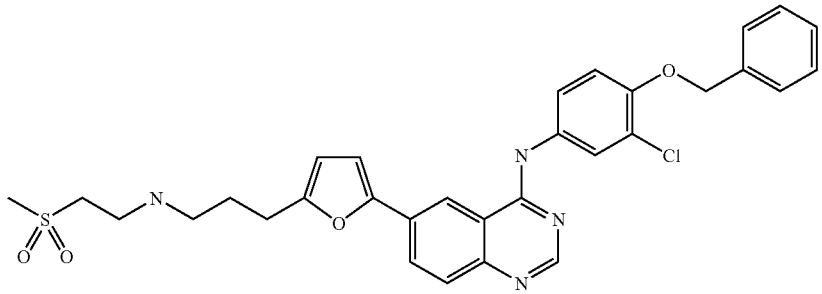

(4-Benzyloxy-3-chlorophenyl)-(6-(2-((2-methane-sulphonyl-ethylamino)propyl)-furan-2-yl)-quinazolin-4-yl)-amine Prepared according to Procedure (J) utilizing 3-(5-{4-[4-(benzyloxy)-3-chloroanilino]-6-quinazolinyl}-2-furyl)-N-[2-methanesulfonyl)ethyl]-2-propenamide (0.11 g, 0.18 mmol) and borane dimethylsulfide (2M, 0.29 mL). $^1$H NMR (DMSO) 9.26 (bs, 2H); 9.19 (s, 1H); 8.87 (s, 1H); 8.34 (m, 1H); 7.91 (m, 2H); 7.68 (m, 1H); 7.49 (m, 2H); 7.42 (m, 3H); 7.36 (m, 2H); 7.25 (m, 1H); 6.45 (m, 1H); 5.28 (s, 2H); 3.58 (m, 2H); 3.36 m, 2H, peak obscured by water); 3.11 (s, 3H); 3.05 (m, 2H); 2.85 (m, 2H); 2.08 (m, 2H).Electrospray MS m/z 591 (MH$^+$).

Example 9

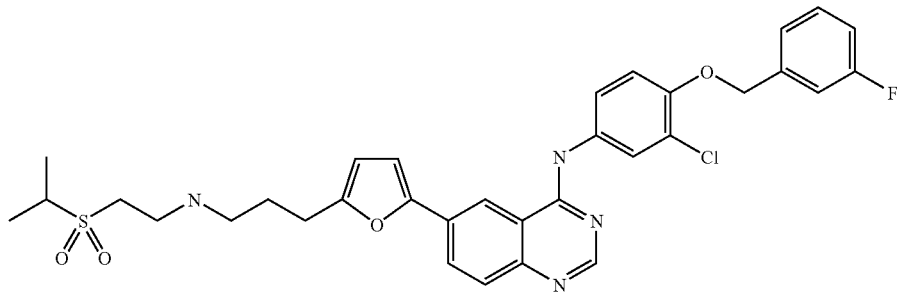

(4-(3-Fluorobenzyloxy)-3-chlorophenyl)-(6-(2-((2-iso-propyl-sulphonyl-ethylamino)-propyl)-furan-2-yl)-quinazolin-4-yl)-amine Prepared according to Procedure (J) utilizing 3-(5-{4-[4-(3-fluoro-benzyloxy)-3-chloroanilino]-6-quinazolinyl}-2- furyl)-N-[2-(iso-propanesulfonyl)ethyl]-2-propenamide (0.088 g, 0.14 mmol) and borane dimethyl sulfide (2M, 0.24 mL). $^1$H NMR (DMSO) 11.13 (s, 1H); 9.44 (s, 1H); 9.05 (bs, 1H); 8.25 (s, 1H); 7.81 (d, 1H); 7.68 (s, 1H); 7.48 (m, 1H); 7.40 (m, 2H); 7.32 (m, 2H); 7.20 (m, 1H); 7.01 (d, 1H); 6.75 (s, 1H); 6.30 (m, 1H); 5.31 (s, 2H); 3.51 (m, 2H); 3.40 (m, 3H); 3.03 (m, 2H); 2.76 (m, 2H); 1.99 (m, 2H); 1.25 (d, 6H). Electrospray MS m/z 639 (MH$^+$).

Example 10

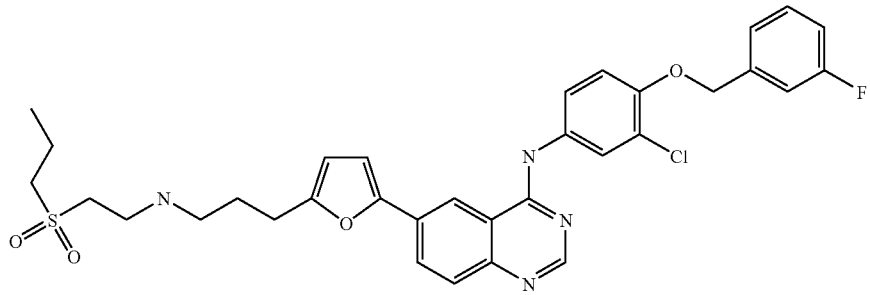

(4-(3-Fluorobenzyloxy)-3-chlorophenyl)-(6-(2-((2-propanesulphonyl-ethylamino)-propyl)-furan-2-yl)-quinazolin-4-yl)-amine Prepared according to Procedure (J) utilizing 3-(5-{4-[4-(3-fluoro-benzyloxy)-3-chloroanilino]-6-quinazolinyl}-2-furyl)-N-[2-(n-propanesulfonyl)ethyl]-2-propenamide (0.045 g, 0.069 mmol), borane dimethyl sulfide (2M, 0.086 mL) and a catalytic amount of sodium borohydride. Electrospray MS m/z 637 (M$^+$).

Example 11

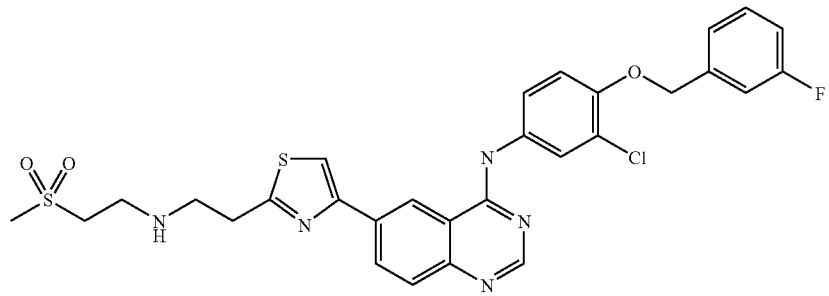

(4-(3-Fluorobenzyloxy)-3-chlorophenyl)-(6-(2-((2-methanesulphonyl-ethylamino)ethyl)-thiazol-4-yl)-quinazolin-4-yl)-amine;

2-(4-{4-[4-(3-Fluoro-benzyloxy)-3-chloroanilino]-6-quinazolinyl}-thiazol-2-yl)-acetic acid (0.018 mmol) was treated with borane dimethylsulfide in THF as outlined in procedure (K) to provide the title compound. Electrospray MS m/z 612 (MH+).

Example 12

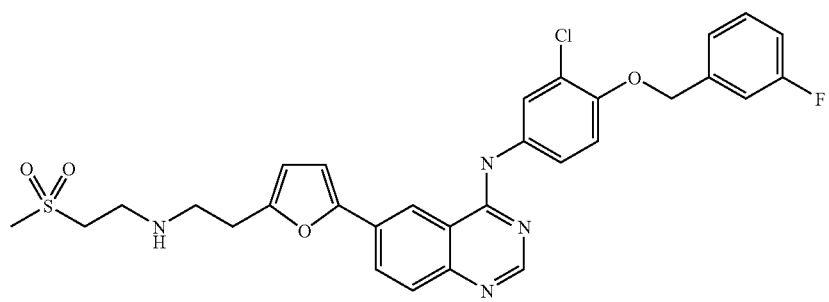

(4-(3-Fluorobenzyloxy)-3-chlorophenyl)-(6-(2-((2-methanesulphonyl-ethylamino)-ethyl)-furan-2-yl)-quinazolin-4-yl)-amine (4-(3-Fluorobenzyloxy)-3-chlorophenyl)-(6-(5-(2-(methylsulfonyl)acetamidoethyl)-furan-2-yl)-quinazolin-4-yl)-amine (15 mg, 0.0247 mmol) was treated with borane dimethylsulfide (2.0 M in THF, 0.0432 mmol) in THF as outlined in procedure (K) to provide the title compound. LC/MS m/z 595 (MH+).

Example 13

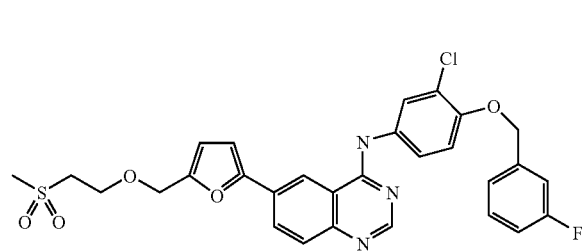

N-{3-chloro-4-[(3-fluorobenzyl)oxy]phenyl}-6-(5-{[2-(methylsulfonyl)ethoxy]methyl}-2-furyl)-4-quinazolinamine Prepared according to Procedure O utilizing 3-[5-(4-{3-chloro-4-[(3-fluorobenzyl)oxy]anilino}-6-quinazolinyl)-2-furyl]-2-methen alcohol (66.8 mg, 0.141 mmol), methyl vinyl sulfone (0.015 mL, 0.169 mmol) and sodium hydride (60% in mineral oil, 0.7 mg, 0.017 mmol) in DMF (3 mL) to provide the title compound (51 mg) after purification by chromatography. $^1$H NMR 400 MHz (DMSO-d6) 9.95 (1 H, s), 8.74 (1 H, s), 8.50 (1 H, s), 8.11 (1 H, d, J=8.8 Hz) 7.96 (1 H, s), 7.76-7.68 (2 H, m), 7.41 (1 H, m), 7.29-7.22 (3 H, m), 7.11 (1 H, m), 7.06 (1 H, d, J=2.8 Hz), 6.65 (1 H, d, J=2.8 Hz), 5.21 (2 H, s), 4.55 (2 H, s), 3.81 (2 H, t), 3.37 (2 H, t), 2.94 (3 H, s). LC/MS m/z 582 (M+H+).

Example 14

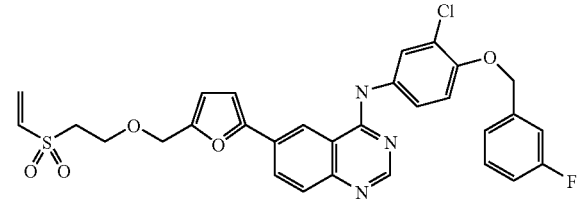

N-{3-chloro-4-[(3-fluorobenzyl)oxy]phenyl}-6-(5-{[2-(vinylsulfonyl)ethoxy]methyl}-2-furyl)-4-quinazolinamine Prepared according to Procedure O utilizing 3-[5-(4-{3-chloro-4-[(3-fluorobenzyl)oxy]anilino}-6-quinazolinyl)-2-furyl]-2-methen alcohol (114 mg, 0.24 mmol), vinyl sulfone (0.0745 mL, 0.72 mmol) and sodium hydride (60% in mineral oil, 0.7 mg, 0.017 mmol) in DMF (3 mL) to provide the title compound (46 mg) after purification by chromatography. $^1$H NMR 400 MHz (DMSO-d6) 9.90 (1 H, s), 8.71 (1 H, s), 8.50 (1 H, s), 8.12 (1 H, m), 7.95 (1 H, d, J=2.8 Hz), J=8.8 Hz), 7.68 (1 H, m), 7.41 (1 H, m), 7.29-7.22 (3 H, m), 7.13 (1 H, m), 7.04 (1 H, d, J=3.2 Hz), 6.89 (1 H, m), 6.64 (1 H, d, J=3.2 Hz), 6.14 (2 H, m), 5.21 (2 H, s), 4.51 (2 H, s), 3.76 (2 H, t), 3.22 (2 H, t). LC/MS m/z 595 (M+H+).

Example 15

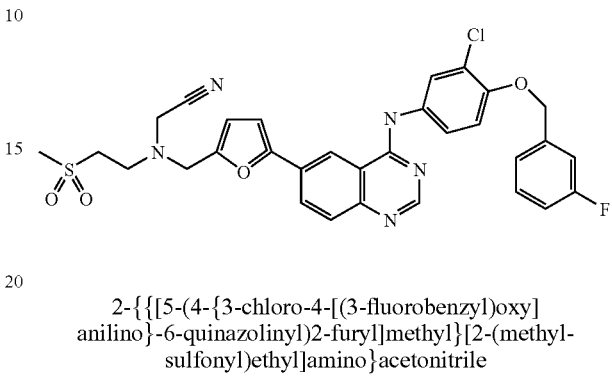

2-{{[5-(4-{3-chloro-4-[(3-fluorobenzyl)oxy]anilino}-6-quinazolinyl)2-furyl]methyl}[2-(methylsulfonyl)ethyl]amino}acetonitrile (4-(3-Fluorobenzyloxy)-3-chlorophenyl)-(6-(2-((2-methanesulphonyl-ethylamino)-ethyl)-furan-2-yl)-quinazolin-4-yl)-amine (116 mg, 0.2 mmol), chloroacetonitrile (0.014 mL, 0.22 mmol) and diisopropyl ethyl amine (0.07 mL, 0.2 mmol) were mixed as outlined in Procedure P to provide the title compound (110 mg). $^1$H NMR 400 MHz (DMSO-d6) 9.84 (1 H, s), 8.69 (1 H, s), 8.50 (1 H, s), 8.10 (1 H, d, J=8.8 Hz), 7.96 (1 H, d, J=2.4 Hz), 7.76 (1 H, d, J=8.8 Hz), 7.68 (1 H, m) 7.42 (1 H, m), 7.29-7.22 (3 H, m), 7.13 (1 H, m), 7.03 (1 H, d, J=3.6 Hz), 6.59 (1 H, d, J=3.6 Hz), 5.22 (2 H, s), 3.84 (2 H, s), 3.81 (2 H, s), 3.37 (2 H, t), 2.98 (3 H, s), 2.96 (2 H, t). LC/MS m/z 620 (M+H+).

Example 16

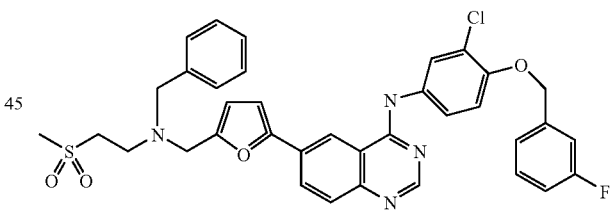

6-[5-({benzyl[2-(methylsulfonyl)ethyl]amino}methyl)-2-furyl]-N-{3-chloro-4-[(3-fluorobenzyl)oxy]phenyl}-4-quinazolinamine (4-(3-Fluorobenzyloxy)-3-chlorophenyl)-(6-(2-((2-methanesulphonyl-ethylamino)-ethyl)-furan-2-yl)-quinazolin-4-yl)-amine (100 mg, 0.173 mmol), benzylbromide (0.025 mL, 0.21 mmol) and diisopropyl ethyl amine (0.07 mL, 0.2 mmol) were mixed as outlined in Procedure P to provide the title compound (89 mg). $^1$H NMR 400 MHz (DMSO-d6) 9.81 (1 H, s), 8.67 (1 H, s), 8.51 (1 H, s), 8.10 (1 H, d, J=8.8 Hz), 7.96 (1 H, d, J=2.4 Hz), 7.77 (1 H, d, J=8.8 Hz), 7.69 (1 H, m), 7.42 (1 H, m), 7.36-7.20 (8 H, m), 7.13 (1 H, m), 7.03 (1 H, d, J=3.6 Hz), 6.53 (1 H, d, J=3.6 Hz), 5.22 (2 H, s), 3.72 (2 H, s), 3.66 (2 H, s), 3.38 (2 H, t), 2.96 (3 H, s), 2.88 (2 H, t). LC/MS m/z 671 (M+H+).

Example 17

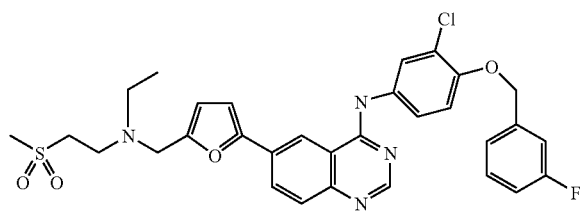

N-{3-chloro-4-[(3-fluorobenzyl)oxy]phenyl}-6-[5-({ethyl[2-(methylsulfonyl) ethyl]amino}methyl)-2-furyl]-4-quinazolinamine (4-(3-Fluorobenzyloxy)-3-chlorophenyl)-(6-(2-((2-methanesulphonyl-ethylamino)-ethyl)-furan-2-yl)-quinazolin-4-yl)-amine (100 mg, 0.17 mmol), bromoethane (0.015 mL, 0.21 mmol) and diisopropyl ethyl amine (0.07 mL, 0.2 mmol) were mixed as outlined in Procedure P to provide the title compound (75 mg). $^1$H NMR 400 MHz (DMSO-d6) 9.81 (1 H, s), 8.66 (1 H, s), 8.50 (1 H, s), 8.08 (1 H, d, J=8.8 Hz), 7.96 (1 H, d, J=2.4 Hz), 7.75 (1 H, d, J=8.8 Hz), 7.68 (1 H, m), 7.42 (1 H, m), 7.29-7.23 (3 H, m), 7.13 (1 H, m), 7.01 (1 H, d, J=3.6 Hz), 6.50 (1 H, d, J=3.6 Hz), 5.21 (2 H, s), 3.73 (2 H, s), 2.95 (5 H, m), 2.86 (2 H, t), 2.50 (2 H, q), 1.00 (3 H, t). LC/MS m/z 608 (M+H$^+$).

Example 18

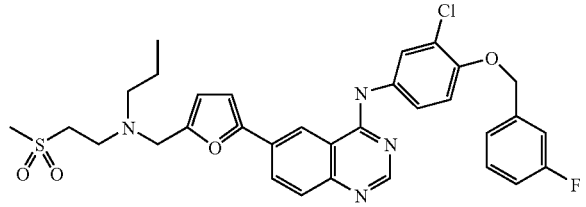

N-{3-chloro-4-[(3-fluorobenzyl)oxy]phenyl}-6-(5-{[[2-(methylsulfonyl) ethyl](propyl)amino]methyl}-2-furyl)-4-quinazolinamine (4-(3-Fluorobenzyloxy)-3-chlorophenyl)-(6-(2-((2-methanesulphonyl-ethylamino)-ethyl)-furan-2-yl)-quinazolin-4-yl)-amine (100 mg, 0.17 mmol), 1-bromopropane (0.019 mL, 0.21 mmol) and diisopropyl ethyl amine (0.07 mL, 0.2 mmol) were mixed as outlined in Procedure P to provide the title compound (79 mg). $^1$H NMR 400 MHz (DMSO-d6) 9.81 (1 H, s), 8.66 (1 H, s), 8.50 (1 H, s), 8.08 (1 H, d, J=8.8 Hz), 7.96 (1 H, d, J=2.4 Hz), 7.75 (1 H, d, J=8.8 Hz), 7.68 (1 H, m), 7.42 (1 H, m), 7.28-7.23 (3 H, m), 7.13 (1 H, m), 7.00 (1 H, d, J=3.6 Hz), 6.49 (1 H, d, J=3.6 Hz), 5.21 (2 H, s), 3.72 (2 H, s), 3.0-2.93 (5 H, m), 2.86 (2 H, t), 2.40 (2 H, q), 1.45 (2 H, m), 0.80 (3 H, t). LC/MS m/z 623 (M+H$^+$).

Example 19

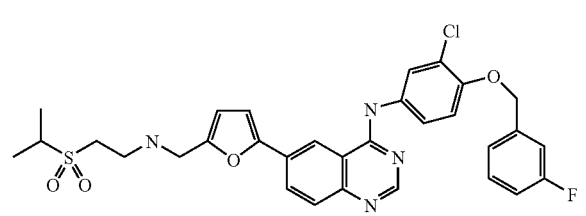

(4-(3-Fluorobenzyloxy)-3-chlorophenyl)-(6-(2-((2-iso-propyl-sulphonyl-ethylamino)-methyl)-furan-2-yl)-quinazolin-4-yl)-amine The title compound and its hydrochloride salt are prepared according to Procedure D utilizing 5-{4-[4-(3-fluorobenzyloxy)-3-chloroanilino]-6-quinazolinyl}-2-furaldehyde (0.317 mmol, 0.15 g), Isopropylsulfonylethyl amine hydrochloride salt (0.475 mmol, 0.105 g) in the presence of Et$_3$N (0.95 mmol, 0.13 mL) and NaBH$_4$ (1.1 mmol, 0.041 g) in THF/MeOH. $^1$H NMR (DMSO-d6) 11.74 (bs, 1H); 9.90 (bs, 2H); 9.63 (s, 1H); 8.91 (s, 1H); 8.42 (d, 1H); 8.04 (m, 1H); 7.95 (d, 1H); 7.81 (d, 1H); 7.47 (m, 1H); 7.37-7.28 (m, 4H); 7.18 (m, 1H); 6.83 (m, 1H); 5.29 (s, 2H); 4.45 (s, 2H); 3.72-3.39 (m, 5H); 1.26 (d, 6H). Electrospray MS 609.

Biological Data

Kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma; psoriasis, arteriosclerosis, arthritis and diabetic retinopathy or other disorders related to uncontrolled angiogenesis and/or vasculogenesis.

The efficacy of compounds of the present invention as inhibitors of protein kinase activity, in particular as inhibitors of erbB family kinase inhibitors, can be evaluated and measured using pharmacological methods known in the art or as described in detail below based on similarly established methodologies.

Substrate Phosphorylation Assay Examples:

EGFR/erbB2/erbB4

The substrate phosphorylation assays use baculovirus expressed, recombinant constructs of the intracellular domains of c-erbB-2 and c-erbB-4 that are constitutively active and EGFr isolated from solubilised A431 cell membranes. The method measures the ability of the isolated enzymes to catalyse the transfer of the γ-phosphate from ATP onto tyrosine residues in a biotinylated synthetic peptide (Biotin-GluGluGluGluTyrPheGluLeuVal). The enzyme is incubated for 30 minutes, at room temperature, with 10 mM MnCl$_2$, ATP and peptide at Km concentrations, and test compound (diluted from a 5 mM stock in DMSO, final DMSO concentration is 2%) in 40 mM HEPES buffer, pH 7.4. The reaction is stopped by the addition of EDTA (final concentration 0.15 mM) and a sample is transferred to a streptavidin-coated 96-well plate. The plate is washed and level of phosphotyrosine on the peptide is determined using a Europium-labelled antiphosphotyrosine antibody and quantified with a time-resolved fluorescence technique. The results are shown in Table 1 as the IC50 value in Micromolar ranges.

TABLE 1

| Example | ErbB4 | ErbB2 | EGFR |
| --- | --- | --- | --- |
| 2 | ++ | +++ | +++ |
| 3 | + | +++ | +++ |
| 4 | + | +++ | +++ |
| 5 | + | +++ | +++ |
| 6 | + | +++ | +++ |
| 7 | ++ | +++ | +++ |
| 8 | + | +++ | +++ |
| 13 | ++ | +++ | +++ |
| 14 | ++ | +++ | +++ |
| 15 | ++ | +++ | +++ |

TABLE 1-continued

| Example | ErbB4 | ErbB2 | EGFR |
|---|---|---|---|
| 16 | ++ | ++ | ++ |
| 17 | ++ | +++ | +++ |
| 18 | +++ | +++ | +++ |
| 19 | ++ | +++ | +++ |

Cell Proliferation Assays

Cellular Assays: Methylene Blue Growth Inhibition Assay

Human breast (BT474), head and neck (HN5) and gastric tumor (N87) cell lines were cultured in low glucose DMEM (Life Technologies 12320-032) containing 10% fetal bovine serum (FBS) at 37° C. in a humidified 10% $CO_2$, 90% air incubator. The SV40 transformed human mammary epithelial cell line HB4a was transfected with either human H-ras cDNA (HB4a r4.2) or the human c-erbB2 cDNA (HB4a c5.2). The HB4a clones were cultured in RPMI containing 10% FBS, insulin (5 μg/ml), hydrocortisone (5 μg/ml), supplemented with the selection agent hygromycin B (50 μg/ml). Cells were harvested using trypsin/EDTA, counted using a haemocytometer, and plated in 100 ml of the appropriate media, at the following densities, in a 96-well tissue culture plate (Falcon 3075): BT474 10,000 cells/well, HN5 3,000 cells/well, N87 10,000 cells/well, HB4a c5.2 3,000 cells/well, HB4a r4.2 3,000 cells/well. The next day, compounds were diluted in DMEM containing 100 mg/ml gentamicin, at twice the final required concentration, from 10 mM stock solutions in DMSO. 100 ml/well of these dilutions were added to the 100 ml of media currently on the cell plates. Medium containing 0.6% DMSO was added to control wells. Compounds diluted in DMEM were added to all cell lines, including the HB4a r4.2 and HB4a c5.2 cell lines. The final concentration of DMSO in all wells was 0.3%. Cells were incubated at 37° C., 10% $CO_2$ for 3 days. Medium was removed by aspiration. Cell biomass was estimated by staining cells with 100 μl per well methylene blue (Sigma M9140, 0.5% in 50:50 ethanol:water), and incubation at room temperature for at least 30 minutes. Stain was removed, and the plates rinsed under a gentle stream of water, and air-dried. To release stain from the cells 100 μl of solubilization solution was added (1% N-lauroyl sarcosine, Sodium salt, Sigma L5125, in PBS), and plates were shaken gently for about 30 minutes. Optical density at 620 nM was measured on a microplate reader. Percent inhibition of cell growth was calculated relative to vehicle treated control wells. Concentration of compound that inhibits 50% of cell growth ($IC_{50}$) was interpolated using nonlinear regression (Levenberg-Marquardt) and the equation, $y=V_{max}*(1-(x/(K+x)))+Y2$, where "K" was equal to the $IC_{50}$. The results are shown in Table 2.

TABLE 2

| Example | BT474 | N87 | HN5 | HB4a c5.2 |
|---|---|---|---|---|
| 2 | ++ | ++ | ++ | ++ |
| 3 | ++ | ++ | ++ | ++ |
| 4 | + | + | ++ | + |
| 5 | + | ++ | ++ | + |
| 6 | ++ | ++ | ++ | ++ |
| 7 | + | + | + | + |
| 8 | ++ | ++ | ++ | ++ |
| 13 | ++ | ++ | ++ | ++ |
| 14 | + | + | + | + |
| 15 | +++ | ++ | +++ | ++ |

TABLE 2-continued

| Example | BT474 | N87 | HN5 | HB4a c5.2 |
|---|---|---|---|---|
| 16 | ++ | ++ | + | + |
| 17 | ++ | ++ | ++ | ++ |
| 18 | ++ | ++ | ++ | ++ |
| 19 | ++ | ++ | ++ | ++ |

| $IC_{50}$ values | Symbol |
|---|---|
| <0.10 uM | +++ |
| 0.10–1.0 uM | ++ |
| 1.0–10.0 uM | + |
| >10.0 uM | − |
| Not determined | ND |

We claim:

1. A compound of formula (I)

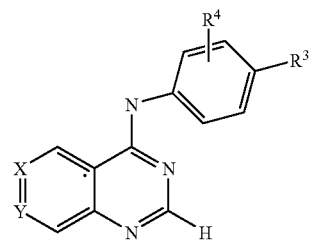

or a salt thereof;

wherein

X is $CR^1$ and Y is N;

$R^1$ represents the group $R^5SO_2CH_2CH_2Z\text{-}(CH_2)_p\text{—Ar—}$, wherein Ar is selected from thiophene and thiazole, wherein said thiophene or thiazole is optionally substituted by one or two groups selected independently from halo, $C_{1-4}$ alkyl; and $C_{1-4}$ alkoxy; Z is selected from O, S, NH and $NR^6$, and p is 1, 2, 3 or 4;

$R^5$ is $C_{1-6}$ alkyl optionally substituted by one or more $R^8$ groups; or $R^5$ is $C_{1-6}$ alkyl substituted by a 5 to 10-membered heterocyclic group or a 3 to 10-membered carbocyclic group, each of which may be optionally substituted by one or more $R^8$ groups; or $R^5$ is selected from the group consisting of a 5 to 10-membered heterocyclic group or a 3 to 10-membered carbocyclic group, each of which may be optionally substituted by one or more $R^8$ groups;

each $R^8$ is independently selected from halo, hydroxy, $C_{1-4}$ alkoxy, nitrile, $NH_2$ or $NR^6R^7$;

$R^6$ is $C_{1-4}$ alkyl, $C_{1-4}$ alkoxy-$C_{1-4}$alkyl, hydroxy$C_{1-4}$alkyl, cyanomethyl, benzyl, $CF_3C(O)$ or $CH_3C(O)$;

$R^7$ is hydrogen or $R^6$;

$R^3$ is selected from pyridylmethoxy, benzyloxy, halo-, dihalo- and trihalobenzyloxy;

$R^4$ is selected from hydrogen, halogen, $C_{1-4}$ alkyl, $C_{2-4}$ alkynyl or cyano.

2. The compound or salt thereof of claim 1, wherein Z is NH, $NR^6$ or O.

3. The compound or salt thereof of claim 1, wherein Z is NH or O.

4. The compound or salt thereof of claim 1, wherein Z is NH.

5. The compound or salt thereof of claim 1, wherein p is 1, 2 or 3.

6. The compound or salt thereof of claim 1, wherein Ar does not carry any optional substituents.

7. The compound or salt thereof of claim 1, wherein $R^5$ is an aromatic heterocyclic or carbocyclic group optionally substituted by a $C_{1-4}$ alkyl group.

8. The compound or salt thereof of claim 1, wherein $R^5$ is pyridyl, phenyl, imidazolyl or N-methylimidazolyl.

9. The compound or salt thereof of claim 1, wherein $R^5$ is $C_{1-6}$ alkyl optionally substituted by one or more groups selected from halo, hydroxy, $C_{1-4}$ alkoxy, nitrile, $NH_2$ or $NR^6R^7$.

10. The compound or salt thereof of claim 1, wherein $R^5$ is $C_{1-6}$ alkyl optionally substituted by one or more groups selected from hydroxy, $C_{1-4}$ alkoxy, $NH_2$ or $NR^6R^7$, wherein $R^6$ represents $C_{1-4}$ alkyl.

11. The compound or salt thereof of claim 1, wherein $R^5$ is unsubstituted $C_{1-6}$ alkyl.

12. The compound or salt thereof of claim 1, wherein $R^3$ is benzyloxy or fluorobenzyloxy.

13. The compound or salt thereof of claim 1, wherein $R^4$ is chloro, bromo, or hydrogen.

14. The compound or salt thereof of claim 1, wherein $R^3$ is benzyloxy or 3-fluorobenzyloxy and $R^4$ is chloro or bromo.

15. The compound or salt thereof of claim 1, wherein Ar is unsubstituted thiazole; $R^3$ is benzyloxy or fluorobenzyloxy; and $R^4$ is hydrogen, chloro or bromo.

16. The compound or salt thereof of claim 1, wherein Ar is unsubstituted thiazole; $R^3$ is fluorobenzyloxy; and $R^4$ is chloro or bromo.

17. The compound or salt thereof of claim 1, wherein Ar is unsubstituted thiazole; $R^3$ is benzyloxy or fluorobenzyloxy; $R^4$ is hydrogen, chloro or bromo; and $R^5$ is unsubstituted $C_{1-6}$ alkyl.

18. The compound or salt thereof of claim 1, wherein Ar is unsubstituted thiazole; $R^3$ is fluorobenzyloxy; $R^4$ is chloro or bromo; and $R^5$ is unsubstituted $C_{1-6}$ alkyl.

19. The compound or salt thereof of claim 1, wherein Ar is unsubstituted thiazole; $R^3$ is benzyloxy or fluorobenzyloxy; $R^4$ is hydrogen, chloro or bromo; and $R^5$ is pyridine, imidazole, or phenyl.

20. The compound or salt thereof of claim 1, wherein Ar is unsubstituted thiazole; $R^3$ is fluorobenzyloxy; $R^4$ is chloro or bromo; and $R^5$ is pyridine, imidazole, or phenyl.

21. The compound or salt thereof of claim 1, wherein Ar is unsubstituted thiophene; $R^3$ is benzyloxy or fluorobenzyloxy; and $R^4$ is hydrogen, chloro or bromo.

22. The compound or salt thereof of claim 1, wherein Ar is unsubstituted thiophene; $R^3$ is fluorobenzyloxy; and $R^4$ is chloro or bromo.

23. The compound or salt thereof of claim 1, wherein Ar is unsubstituted thiophene; $R^3$ is benzyloxy or fluorobenzyloxy; $R^4$ is hydrogen, chloro or bromo; and $R^5$ is unsubstituted $C_{1-6}$ alkyl.

24. The compound or salt thereof of claim 1, wherein Ar is unsubstituted thiophene; $R^3$ is fluorobenzyloxy; $R^4$ is chloro or bromo; and $R^5$ is unsubstituted $C_{1-6}$ alkyl.

25. The compound or salt thereof of claim 1, wherein Ar is unsubstituted thiophene; $R^3$ is benzyloxy or fluorobenzyloxy; $R^4$ is hydrogen, chloro or bromo; and $R^5$ is pyridine, imidazole, or phenyl.

26. The compound or salt thereof of claim 1, wherein Ar is unsubstituted thiophene; $R^3$ is fluorobenzyloxy; $R^4$ is chloro or bromo; and $R^5$ is pyridine, imidazole, or phenyl.

27. A compound according to claim 1, wherein the compound is a compound of formula (I')

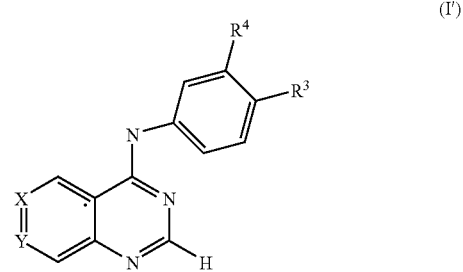

or a salt thereof.

28. A pharmaceutical composition, comprising: a therapeutically effective amount of at least one compound or salt thereof as claimed in claim 1 and one or more pharmaceutically acceptable carriers, diluents or excipients.

29. A pharmaceutical composition, comprising: a therapeutically effective amount of at least one compound as claimed in claim 27 and one or more pharmaceutically acceptable carriers, diluents or excipients.

* * * * *

UNITED STATES PATENT AND TRADEMARK OFFICE
CERTIFICATE OF CORRECTION

PATENT NO.        : 7,265,123 B2                                        Page 1 of 1
APPLICATION NO. : 11/562047
DATED             : September 4, 2007
INVENTOR(S)       : Cockerill et al.

It is certified that error appears in the above-identified patent and that said Letters Patent is hereby corrected as shown below:

On the Title Page (62) and col 1, lines 3-13 – Related U.S. Application Data should read:
Related U.S. Application Data
--Division of application No. 11/400,284, filed on Apr. 7, 2006, now Pat. No. 7,189,734, which is a division of application No. 11/061,578, filed on Feb. 18, 2005, now Pat. No. 7,084,147, which is a division of application No. 10/030,527, filed on Jan. 9, 2002, now Pat. No. 6,933,299, filed as 371 of international application No. PCT/US00/18128, filed on Jun. 30, 2000.--

Signed and Sealed this

Twenty-seventh Day of May, 2008

JON W. DUDAS
*Director of the United States Patent and Trademark Office*